United States Patent
Granger et al.

(10) Patent No.: US 10,683,289 B2
(45) Date of Patent: Jun. 16, 2020

(54) APOPTOSIS SIGNAL-REGULATING KINASE 1 INHIBITORS AND METHODS OF USE THEREOF

(71) Applicant: ENANTA PHARMACEUTICALS, INC., Watertown, MA (US)

(72) Inventors: Brett Granger, Sudbury, MA (US); Guoqiang Wang, Belmont, MA (US); Ruichao Shen, Belmont, MA (US); Jing He, Somerville, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 16/400,498

(22) Filed: May 1, 2019

(65) Prior Publication Data
US 2019/0337935 A1 Nov. 7, 2019

Related U.S. Application Data

(60) Provisional application No. 62/665,902, filed on May 2, 2018.

(51) Int. Cl.
*C07D 417/14* (2006.01)
*A61K 31/4164* (2006.01)
*A61K 31/4196* (2006.01)
*A61K 31/4439* (2006.01)

(52) U.S. Cl.
CPC .................. *C07D 417/14* (2013.01)

(58) Field of Classification Search
None
See application file for complete search history.

(56) References Cited

U.S. PATENT DOCUMENTS

| | | |
|---|---|---|
| 6,534,651 B2 | 3/2003 | Jagtap et al. |
| 8,378,108 B2 | 2/2013 | Corkey et al. |
| 8,653,075 B2 | 2/2014 | Grundl et al. |
| 9,067,933 B2 | 6/2015 | Corkey et al. |
| 9,254,284 B2 | 2/2016 | Notte |
| 2005/0113450 A1 | 5/2005 | Thorarensen et al. |
| 2009/0318425 A1 | 12/2009 | Chang et al. |
| 2010/0029619 A1 | 2/2010 | Uchikawa et al. |
| 2011/0009410 A1 | 1/2011 | Corkey et al. |
| 2012/0004267 A1 | 1/2012 | Corkey et al. |
| 2013/0203731 A1 | 8/2013 | Chang et al. |
| 2013/0210810 A1 | 8/2013 | Singh et al. |
| 2014/0018370 A1 | 1/2014 | Corkey et al. |
| 2014/0249135 A1 | 9/2014 | Burger et al. |
| 2014/0329850 A1 | 11/2014 | Chang |
| 2015/0005280 A1 | 1/2015 | Sasmal et al. |
| 2017/0210748 A1 | 7/2017 | Witty et al. |
| 2018/0327388 A1 | 11/2018 | Wang et al. |
| 2018/0362501 A1 | 12/2018 | Wang et al. |
| 2018/0362502 A1 | 12/2018 | Granger et al. |
| 2018/0362503 A1 | 12/2018 | Granger et al. |
| 2019/0062310 A1 | 2/2019 | Wang et al. |

FOREIGN PATENT DOCUMENTS

| | | |
|---|---|---|
| CN | 107793400 A | 3/2018 |
| WO | 2004018428 A1 | 3/2004 |
| WO | 2005009470 A1 | 2/2005 |
| WO | 2005103288 A1 | 11/2005 |
| WO | 2007000339 A1 | 1/2007 |
| WO | 2008082579 A1 | 7/2008 |
| WO | 2009011850 A2 | 1/2009 |

(Continued)

OTHER PUBLICATIONS

Kawarazaki, et al., "Apoptosis signal-regulating kinase 1 as a therapeutic target", Expert Opinion on Therapeutic Targets, 18(6), 2014, 651-664.
Starosyla, S. et al., "ASK1 Pharmacophore Model Derived from Diverse Classes of Inhibitors", Bioorganic & Medicinal Chemistry Letters, 24, 2014, 4418-4423.
Pubmed Compound Summary for CID 53276841, '2-Methyl-1,1,3-trioxo-N-pyridin-2-yl-1,2-benzothiazole-6-carboxamide', U.S. National library of Medicine, Aug. 1, 2011 (Aug. 1, 2011), p. 1-7; p. 2 (https://lpubchem.ncbi.nlm.nih.gov/compound/53276841).
Gibson, et al., "Structure-based drug design of novel ASK1 inhibitors using an integrated lead optimization strategy", Bioorganic & Medicinal Chemistry Letters, 2017, 1-5.

(Continued)

*Primary Examiner* — Zinna Northington Davis
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts and esters thereof:

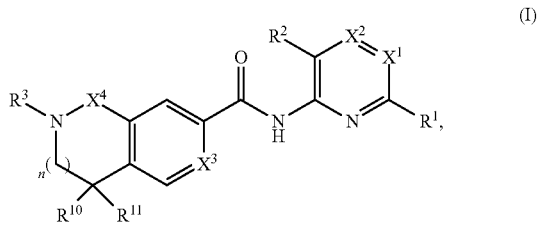

which inhibit the Apoptosis signal-regulating kinase 1 (ASK-1), which associated with autoimmune disorders, neurodegenerative disorders, inflammatory diseases, chronic kidney disease, cardiovascular disease. The present invention further relates to pharmaceutical compositions comprising the aforementioned compounds for administration to a subject suffering from ASK-1 related disease. The invention also relates to methods of treating an ASK-1 related disease in a subject by administering a pharmaceutical composition comprising the compounds of the present invention. The present invention specifically relates to methods of treating ASK-1 associated with hepatic steatosis, including non-alcoholic fatty liver disease (NAFLD) and non-alcoholic steatohepatitis disease (NASH).

19 Claims, No Drawings

(56) References Cited

FOREIGN PATENT DOCUMENTS

| WO | 2009027283 | A1 | 3/2009 |
|---|---|---|---|
| WO | 2009123986 | A1 | 10/2009 |
| WO | 2010008843 | A1 | 1/2010 |
| WO | 2011008709 | A1 | 1/2011 |
| WO | 2011041293 | A1 | 4/2011 |
| WO | 2011097079 | A1 | 8/2011 |
| WO | 2012003387 | A1 | 1/2012 |
| WO | 2012011548 | A1 | 1/2012 |
| WO | 2012080735 | A1 | 6/2012 |
| WO | 2013112741 | A1 | 8/2013 |
| WO | 2014100541 | A1 | 6/2014 |
| WO | 2014106019 | A2 | 7/2014 |
| WO | 2014137728 | A1 | 9/2014 |
| WO | 2015095059 | A1 | 6/2015 |
| WO | 2016049069 | A1 | 3/2016 |
| WO | 2016049070 | A1 | 3/2016 |
| WO | 2016105453 | A1 | 6/2016 |
| WO | 2016106384 | A1 | 6/2016 |
| WO | 2018090869 | A1 | 5/2018 |
| WO | 2018133856 | A1 | 7/2018 |
| WO | 2018133866 | A1 | 7/2018 |
| WO | 2018148204 | A1 | 8/2018 |
| WO | 2018149284 | A1 | 8/2018 |
| WO | 2018151830 | A1 | 8/2018 |
| WO | 2018157857 | A1 | 9/2018 |
| WO | 2018169742 | A1 | 9/2018 |
| WO | 2018218051 | A1 | 11/2018 |

OTHER PUBLICATIONS

Lanier, Marion et al., "Structure-Based Design of ASK1 Inhibitors as Potential Agents for Heart Failure", ACS Medicinal Chemistry Letters 2017, vol. 8, 2017, 316-320.
Loomba, et al., "The ASK1 Inhibitor Selonsertib in Patients with Nonalcoholic Steatohepatitis: A Randomized, Phase 2 Trial", Hepatology 67(2), 2018, 549-559.
Lovering, et al., "Rational approach to highly potent and selective apoptosis signal regulating kinase 1 (ASK1) inhibitors", European Journal of Medicinal Chemistry, 145, 2018, 606-621.
Monastyrsky, et al., "Discovery of 2-arylquinazoline derivatives as a new class of ASK1 inhibitors", Bioorganic & Medicinal Chemistry Letters, 28, 2018, 400-404.
Patani, George A. et al., "Bioisosterism: A Rational Approach in Drug Design", Chem. Rev. 1996, 96, 1996, 3147-3176.
Sheridan, Robert P., "The Most Common Chemical Replacements in Drug-Like Compounds", J. Chem. Info. Comput. Sci. 2002, vol. 42, 2002, 103-108.
Terao, et al., "Design and biological evaluation of imidazo[1,2-a]pyridines as novel and potent ASK1 inhibitors", Bioorganic & Medicinal Chemistry Letters, 22, 2012, 7326-7329.
Volynets, et al., "Identification of 3H-Naphtho[1,2,3-de]quinoline-2,7-diones as Inhibitors of Apoptosis Signal-Regulating Kinase 1 (ASK1)", Journal of Medicinal Chemistry, 54, 2011, 2680-2686.
Volynets, et al., "Rational design of apoptosis signal-regulating kinase 1 inhibitors: Discovering novel structural scaffold", European Journal of Medicinal Chemistry 61, 2013, 104-115.
Wermuth, C. G., "Molecular Variations Based on Isosteric Replacements", in "The Practice of Medicinal Chemistry", Academic Press Limited, 1996, 203-237.

APOPTOSIS SIGNAL-REGULATING KINASE 1 INHIBITORS AND METHODS OF USE THEREOF

RELATED APPLICATIONS

This application claims the benefit of U.S. Provisional Application No. 62/665,902, filed on May 2, 2018. The entire teachings of the above application are incorporated herein by reference.

TECHNICAL FIELD

The present invention relates generally to compounds and pharmaceutical compositions useful as ASK-1 inhibitors. Specifically, the present invention relates to compounds useful as inhibitors of ASK-1 and methods for their preparation and use.

BACKGROUND OF THE INVENTION

Apoptosis signal-regulating kinase 1 (ASK-1) is a member of the mitogen-activated protein kinase kinase kinase (MAPKKK, MAP3K) family, which when activated phosphorylates downstream MAP kinase kinases (MAPKK, MAP2K), which in turn activate MAP kinases (MAPK). MAPKs elicit a response by phosphorylating cellular substrates, thus regulating the activity of transcription factors that ultimately control gene expression. Specifically ASK-1, also known as MAPKKK5, phosphorylates MAPKK4/MAPKK7 or MAPKK3/MAPKK6, which subsequently phosphorylates and activates the c-Jun N-terminal protein kinase (NK) and p38 MAPKs, respectively (H. Ichijo, et al., *Cell Comm. Signal* 2009, 7, 1-10; K. Takeda, et al., *Annu. Rev. Pharmacol. Toxicol.* 2008, 48, 199-225; H. Nagai, et al., *J. Biochem. Mol. Biol.* 2007, 40, 1-6). Activation of the JNK and p38 pathways triggers a downstream stress response such as apoptosis, inflammation, or differentiation (H. Ichijo, et al., *Science* 1997, 275, 90-94; K. Takeda, et al., *J. Biol. Chem.* 2000, 275, 9805-9813; K. Tobiume, et al., *EMBO Rep.* 2001, 2, 222-228; K. Sayama et al., *J. Biol. Chem.* 2001, 276, 999-1004).

The activity of ASK-1 is regulated by thioredoxin (Trx), which binds to the N-terminal end of ASK-1 (M. Saitoh, et al., *EMBO J.* 1998, 17, 2596-2606). ASK-1 is activated succeeding autophosphorylation at Thr838 in response to environmental stimuli including oxidative stress, lipopolysaccharides (LPS), reactive oxygen species (ROS), endoplasmic reticulum (ER) stress, an increase in cellular calcium ion concentrations, Fas ligand, and various cytokines such as tumor necrosis factor (TNF) (H. Nishitoh, et al., *Genes Dev.* 2002, 16, 1345-1355; K. Takeda, et al., *EMBO Rep.* 2004, 5, 161-166; A. Matsuzawa, et al., *Nat. Immunol.* 2005, 6, 587-592).

ASK-1 has been associated with autoimmune disorders, neurodegenerative disorders, inflammatory diseases, chronic kidney disease, cardiovascular disease, metabolic disorders, and acute and chronic liver diseases (R. Hayakawa, et al., *Proc. Jpn. Acad., Ser. B* 2012, 88, 434-453).

More specifically, ASK-1 has been associated with hepatic steatosis, including non-alcoholic fatty liver disease (NAFLD) and non-alcoholic steatohepatitis (NASH). In a mouse model, high fat diets have caused induction of hepatic steatosis, ultimately causing fat accumulation and fatty acid oxidation. This led to the generation of ROS which caused hepatocyte dysfunction and death (S. K. Mantena, et al., *Free Radic. Biol. Med.* 2008, 44, 1259-1272; S. K. Mantena, et al., *Biochem. J.* 2009, 417, 183-193). Moreover, TNF was shown to be critical for apoptosis of hepatocytes through the ASK-1-JNK pathway, and TNF deficient mice showed reduced hepatic steatosis and fibrosis (W. Zhang, et al., *Biochem. Biophys. Res. Commun.* 2010, 391, 1731-1736).

Small molecule compounds which act as ASK-1 inhibitors have been disclosed in the following publications: WO 2008/016131, WO 2009/027283, WO 2009/0318425, WO 2009/123986, US 2009/0318425, WO 2011/041293, WO 2011/097079, US 2011/0009410, G. P. Volynets, et al., *J. Med. Chem.* 2011, 54, 2680-2686, WO 2012/003387, WO 2012/011548, WO 2012/080735, Y. Terao, et al., *Bioorg. Med. Chem. Lett.* 2012, 22, 7326-7329, WO 2013/112741, G. P. Volynets, et al., *Eur. J. Med. Chem.* 2013, 16, 104-115, US 2014/0018370, WO 2014/100541, WO 2015/095059, WO 2016/049069, WO 2016/049070, WO 2018/090869, WO 2018/133865, WO 2018/133866, WO 2018/148204, WO 2018/149284, WO 2018/151830, WO/2018/157856, WO 2018/157857, WO 2018/160406, WO 2018/169742, WO 2018/183122, WO 2018/187506, WO 2018/209354, WO 2018/218042, WO 2018/218044, WO 2018/218051, WO 2018/233553, US 2019/0062310, WO 2019/070742, WO 2019/050794, WO 2019/051265, and WO 2019/034096.

There is a need for the development of ASK-1 inhibitors for the treatment and prevention of disease.

SUMMARY OF THE INVENTION

The present invention provides compounds which inhibit ASK-1 as well as methods of using these compounds to treat disease.

In one aspect, the invention provides compounds represented by Formula I, and pharmaceutically acceptable salts and esters thereof:

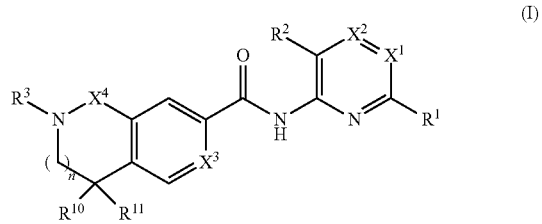

wherein $R^1$ is selected from

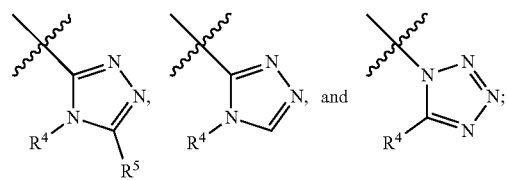

$X^1$ and $X^2$ are each independently $C(R^8)$ or N;

$X^3$ is $C(R^9)$ or N;

$R^9$ is selected from the group consisting of hydrogen, optionally substituted $-C_1$-$C_8$ alkyl, optionally substituted $-C_1$-$C_8$ alkoxy and halogen;

$X^4$ is S, S(O), or $SO_2$;

R⁴ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8-membered heterocycloalkyl;
9) Substituted or unsubstituted heteroaryl; and
10) Substituted or unsubstituted heteroarylalkyl;

$R^2$, $R^5$ and $R^8$ are each independently selected from the group consisting of:
1) Hydrogen;
2) Halogen;
3) —$NO_2$;
4) Cyano;
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;
8) Substituted or unsubstituted —$C_3$-$C_8$ cycloalkyl;
9) Substituted or unsubstituted aryl;
10) Substituted or unsubstituted arylalkyl;
11) Substituted or unsubstituted 3- to 8-membered heterocycloalkyl;
12) Substituted or unsubstituted heteroaryl;
13) Substituted or unsubstituted heteroarylalkyl;
14) —$N(R^6)(R^7)$;
15) —$S(O)_2N(R^6)(R^7)$;
16) —$N(R^6)C(O) R^7$; and
17) —$N(R^6)S(O)_2R^6$;

wherein $R^6$ and $R^7$ are independently selected from the group consisting of hydrogen, —$C_1$-$C_8$ alkyl, —$C_1$-$C_8$ alkenyl, —$C_1$-$C_8$ alkynyl, —$C_3$-$C_8$ cycloalkyl, aryl, heterocycloalkyl, heteroaryl, and heteroarylalkyl, each of which is optionally substituted with 1-3 substituents independently selected from halo, alkyl, alkylamino, dialkylamino, alkylC(O)NH—, arylC(O)NH—, heteroarylC(O)NH—, —CN, alkoxy, —$CF_3$, aryl, and heteroaryl; alternatively, $R^6$ and $R^7$ are taken together with the nitrogen atom to which they are attached to form an optionally substituted heterocyclic;

$R^3$ is selected from the group consisting of:
1) Substituted or unsubstituted —$C_1$-$C_8$ alkyl;
2) Substituted or unsubstituted —$C_2$-$C_8$ alkenyl;
3) Substituted or unsubstituted —$C_2$-$C_8$ alkynyl;
4) Substituted or unsubstituted —$C_3$-$C_8$ cycloalkyl;
5) Substituted or unsubstituted aryl;
6) Substituted or unsubstituted arylalkyl;
7) Substituted or unsubstituted 3- to 8-membered heterocycloalkyl;
8) Substituted or unsubstituted heteroaryl;
9) Substituted or unsubstituted heteroarylalkyl;
10) —$C(O)R^6$;
11) —$C(O)OR^6$;
12) —$C(O)N(R^6)(R')$;
13) —$SO_2R^6$; and
14) Hydrogen;
wherein $R^6$ and $R^7$ are as previously defined;

$R^{10}$ and $R^{11}$ are each independently selected from the group consisting of hydrogen, halogen, and optionally substituted —$C_1$-$C_8$ alkyl; alternatively $R^{10}$ and $R^{11}$ are taken together with the carbon atom to which they are attached to form an optionally substituted cycloalkyl, cycloalkenyl or heterocyclic; and n is 0, 1 or 2; preferably n is 0 or 1.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an ASK-1 mediated disease or condition. The method comprises administering a therapeutically effective amount of a compound of Formula (I) or a pharmaceutically acceptable salt thereof. The present invention also provides the use of a compound of Formula (I), or a pharmaceutically acceptable salt thereof, in the manufacture of a medicament for the prevention or treatment of an ASK-1 mediated disease or condition. Such diseases include autoimmune disorders, neurodegenerative disorders, inflammatory diseases, chronic kidney disease, cardiovascular disease, metabolic disorders, and acute and chronic liver diseases.

DETAILED DESCRIPTION OF THE INVENTION

A first embodiment of the invention is a compound represented by Formula I as described above, or a pharmaceutically acceptable salt or ester thereof.

In certain embodiments of the compounds of Formula I $R^4$ is selected from the groups below:

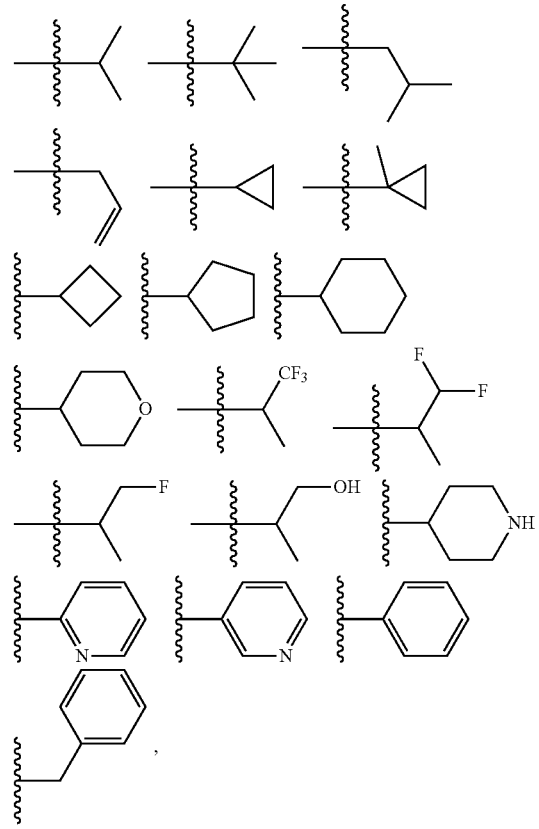

wherein each of these groups is optionally substituted. Preferably, R is selected from

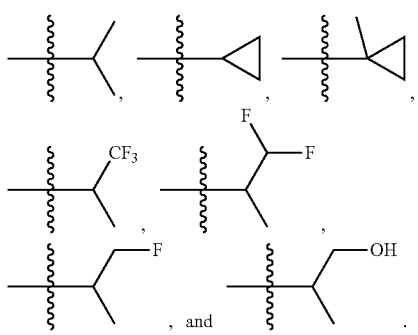

In certain embodiments of the compounds of Formula I R² is hydrogen or halogen.

In certain embodiments of the compounds of Formula I R⁵ is hydrogen.

In certain embodiments of the compounds of Formula I, R² is hydrogen, R⁵ is hydrogen, and n is 0 or 1.

In certain embodiments of the compounds of Formula I, R³ is not hydrogen.

In certain embodiments of the compounds of Formula I, R³ is selected from the groups below:

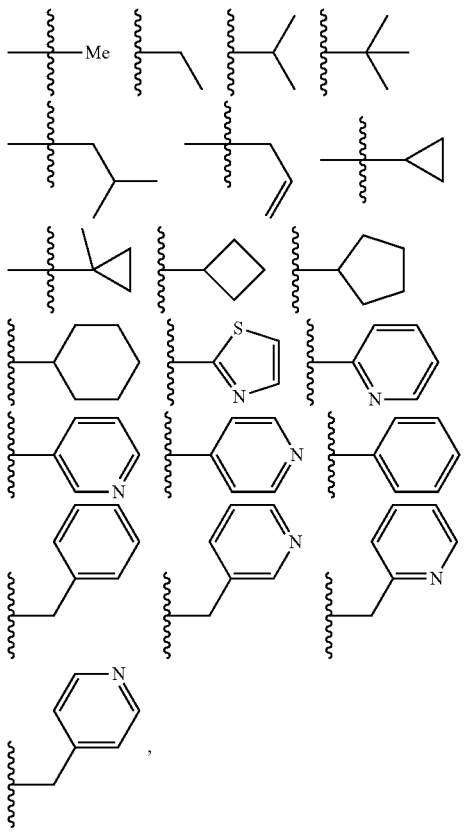

wherein each of these groups is optionally substituted.

In certain embodiments of the compounds of Formula I, X³ is selected from C—H, C—F, C—OMe, and N.

In certain embodiments of the compounds of Formula I, X⁴ is SO₂.

In certain embodiments of the compounds of Formula I, X³ is C(R⁹), where R⁹ is halogen or C₁-C₄-alkoxy, preferably fluoro or methoxy.

In certain embodiments of the compounds of Formula I, at least one of X¹ and X² is C(R⁸). Preferably, each R⁸ is hydrogen.

In certain embodiments, the compound of Formula I is represented by Formula Ia-1 or Formula Ia-2, or a pharmaceutically acceptable salt or ester thereof:

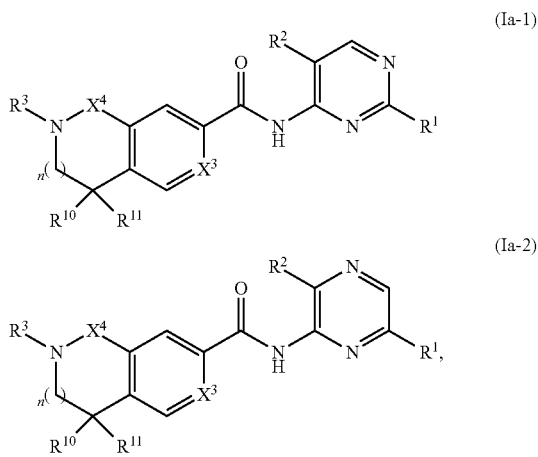

wherein R¹, R², R³, R¹⁰, R¹¹, X³, X⁴ and n are as previously defined. In certain embodiments, the compound of Formula I is represented by Formula Ib, or a pharmaceutically acceptable salt or ester thereof:

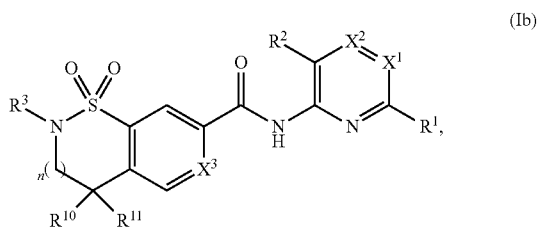

wherein R¹, R², R³, R¹⁰, R¹¹, X¹, X², X³, and n are as previously defined.

In certain embodiments, the compound of Formula I is represented by Formula Ib-1 or Formula Ib-2, or a pharmaceutically acceptable salt or ester thereof:

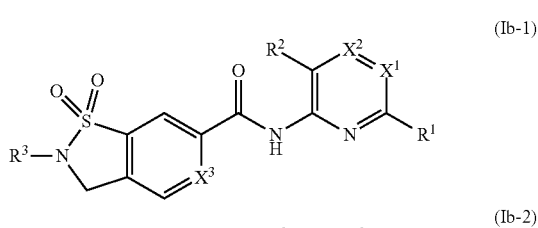

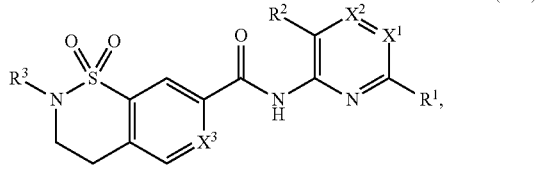

wherein R¹, R², R³, R¹⁰, R¹¹, X¹, X², and X³ are as previously defined.

In certain embodiments, the invention provides compounds represented by Formula II and pharmaceutically acceptable salts and esters thereof:

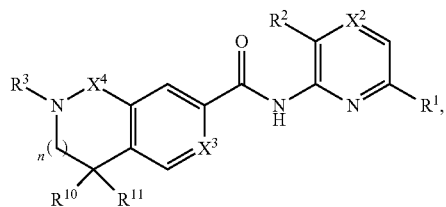

(II)

wherein $R^1$, $R^2$, $R^3$, $R^{10}$, $R^{11}$, $X^2$, $X^3$, $X^4$ and n are as previously defined.

In certain embodiments, the invention provides compounds represented by Formula III and pharmaceutically acceptable salts and esters thereof:

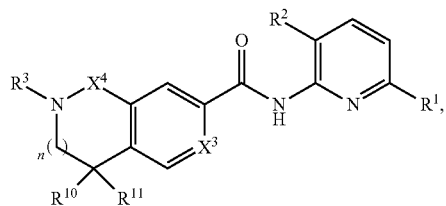

(III)

wherein $R^1$, $R^2$, $R^3$, $R^{10}$, $R^{11}$, $X^3$, $X^4$ and n are as previously defined.

In certain embodiments, the invention provides compounds represented by Formula IV and pharmaceutically acceptable salts and esters thereof:

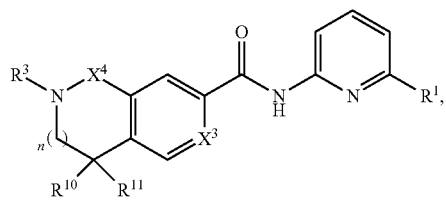

(IV)

wherein $R^1$, $R^3$, $R^{10}$, $R^{11}$, $X^3$, $X^4$ and n are as previously defined.

In certain embodiments, the invention provides compounds represented by Formula V and pharmaceutically acceptable salts and esters thereof:

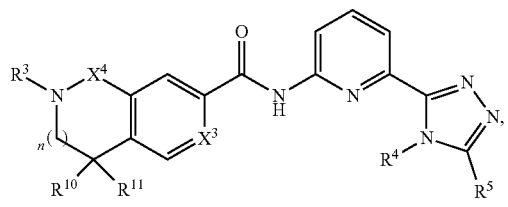

(V)

wherein $R^3$, $R^4$, $R^5$, $R^{10}$, $R^{11}$, $X^3$, $X^4$ and n are as previously defined.

In certain embodiments, the invention provides compounds represented by Formula VI and pharmaceutically acceptable salts and esters thereof:

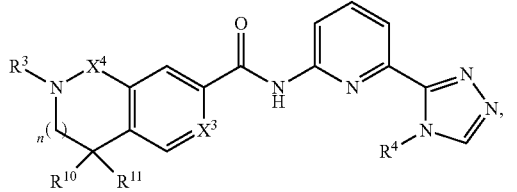

(VI)

wherein $R^3$, $R^4$, $R^{10}$, $R^{11}$, $X^3$, $X^4$ and n are as previously defined.

In certain embodiments, the invention provides compounds represented by Formula VII and pharmaceutically acceptable salts and esters thereof:

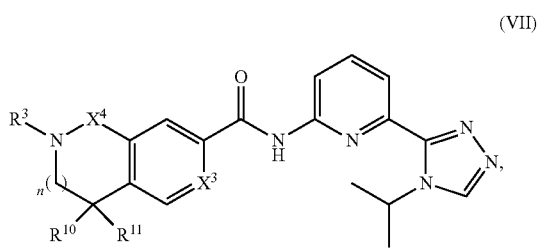

(VII)

wherein $R^3$, $R^{10}$, $R^{11}$, $X^3$, $X^4$ and n are as previously defined.

In certain embodiments, the invention provides compounds represented by Formula VIII and pharmaceutically acceptable salts and esters thereof:

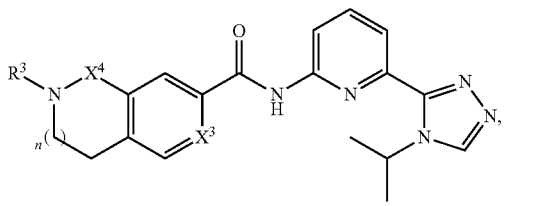

(VIII)

wherein $R^3$, $X^3$, $X^4$ and n are as previously defined.

In certain embodiments, the invention provides compounds represented by Formula IX and pharmaceutically acceptable salts and esters thereof:

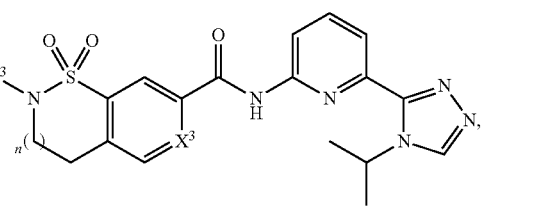

(IX)

wherein $R^3$, $X^3$, and n are as previously defined.

Representative compounds of the invention include, but are not limited to, the following compounds (compound 1 to compound 136 in Table 1) according to Formula IX, and pharmaceutically acceptable salts and esters thereof, wherein $R^3$, $X^3$, and n are delineated for each compound in Table 1.

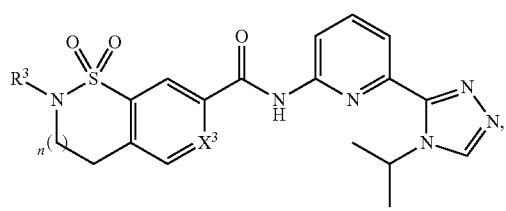

(IX)

TABLE 1

| compound | $R^3$ | $X^3$ | n |
|---|---|---|---|
| 1 | H | C—H | 0 |
| 2 | Methyl | C—H | 0 |
| 3 | Ethyl | C—H | 0 |
| 4 | Propyl | C—H | 0 |
| 5 | Allyl | C—H | 0 |
| 6 | i-Propyl | C—H | 0 |
| 7 | cyclopropyl | C—H | 0 |
| 8 | i-Butyl | C—H | 0 |
| 9 | sec-Butyl | C—H | 0 |
| 10 | t-Butyl | C—H | 0 |
| 11 | cyclobutyl | C—H | 0 |
| 12 | -CH2CH2-OMe | C—H | 0 |
| 13 | -CH2CH2CH2-OH | C—H | 0 |
| 14 | -CH2CH2-CF3 | C—H | 0 |
| 15 | cyclopentyl | C—H | 0 |
| 16 | cyclohexyl | C—H | 0 |
| 17 | -Ph | C—H | 0 |
| 18 | H | C—F | 0 |
| 19 | Methyl | C—F | 0 |
| 20 | Ethyl | C—F | 0 |
| 21 | Propyl | C—F | 0 |
| 22 | Allyl | C—F | 0 |
| 23 | i-Propyl | C—F | 0 |
| 24 | cyclopropyl | C—F | 0 |
| 25 | i-Butyl | C—F | 0 |
| 26 | sec-Butyl | C—F | 0 |
| 27 | t-Butyl | C—F | 0 |
| 28 | cyclobutyl | C—F | 0 |
| 29 | -CH2CH2-OMe | C—F | 0 |
| 30 | -CH2CH2CH2-OH | C—F | 0 |
| 31 | -CH2CH2-CF3 | C—F | 0 |
| 32 | cyclopentyl | C—F | 0 |
| 33 | cyclohexyl | C—F | 0 |
| 34 | -Ph | C—F | 0 |
| 35 | H | C—OMe | 0 |
| 36 | Methyl | C—OMe | 0 |
| 37 | Ethyl | C—OMe | 0 |
| 38 | Propyl | C—OMe | 0 |
| 39 | Allyl | C—OMe | 0 |
| 40 | i-Propyl | C—OMe | 0 |
| 41 | cyclopropyl | C—OMe | 0 |
| 42 | i-Butyl | C—OMe | 0 |
| 43 | sec-Butyl | C—OMe | 0 |
| 44 | t-Butyl | C—OMe | 0 |
| 45 | cyclobutyl | C—OMe | 0 |

TABLE 1-continued

| compound | R³ | X³ | n |
|---|---|---|---|
| 46 | -CH2CH2-OMe | C—OMe | 0 |
| 47 | -CH2CH2-OH | C—OMe | 0 |
| 48 | -CH2CH2CH2-CF3 | C—OMe | 0 |
| 49 | -cyclopentyl | C—OMe | 0 |
| 50 | -cyclohexyl | C—OMe | 0 |
| 51 | -Ph | C—OMe | 0 |
| 52 | H | N | 0 |
| 53 | Methyl | N | 0 |
| 54 | Ethyl | N | 0 |
| 55 | Propyl | N | 0 |
| 56 | Allyl | N | 0 |
| 57 | i-Propyl | N | 0 |
| 58 | -cyclopropyl | N | 0 |
| 59 | i-Butyl | N | 0 |
| 60 | sec-Butyl | N | 0 |
| 61 | t-Butyl | N | 0 |
| 62 | -cyclobutyl | N | 0 |
| 63 | -CH2CH2-OMe | N | 0 |
| 64 | -CH2CH2-OH | N | 0 |
| 65 | -CH2CH2CH2-CF3 | N | 0 |
| 66 | -cyclopentyl | N | 0 |
| 67 | -cyclohexyl | N | 0 |
| 68 | -Ph | N | 0 |
| 69 | H | C—H | 1 |
| 70 | Methyl | C—H | 1 |
| 71 | Ethyl | C—H | 1 |
| 72 | Propyl | C—H | 1 |
| 73 | Allyl | C—H | 1 |
| 74 | i-Propyl | C—H | 1 |
| 75 | -cyclopropyl | C—H | 1 |
| 76 | i-Butyl | C—H | 1 |
| 77 | sec-Butyl | C—H | 1 |
| 78 | t-Butyl | C—H | 1 |
| 79 | -cyclobutyl | C—H | 1 |
| 80 | -CH2CH2-OMe | C—H | 1 |
| 81 | -CH2CH2-OH | C—H | 1 |
| 82 | -CH2CH2CH2-CF3 | C—H | 1 |
| 83 | -cyclopentyl | C—H | 1 |
| 84 | -cyclohexyl | C—H | 1 |
| 85 | -Ph | C—H | 1 |
| 86 | H | C—F | 1 |
| 87 | Methyl | C—F | 1 |
| 88 | Ethyl | C—F | 1 |
| 89 | Propyl | C—F | 1 |
| 90 | Allyl | C—F | 1 |
| 91 | i-Propyl | C—F | 1 |
| 92 | -cyclopropyl | C—F | 1 |

TABLE 1-continued

| compound | R³ | X³ | n |
|---|---|---|---|
| 93 | i-Butyl | C—F | 1 |
| 94 | sec-Butyl | C—F | 1 |
| 95 | t-Butyl | C—F | 1 |
| 96 | cyclobutyl | C—F | 1 |
| 97 | -CH₂CH₂OMe | C—F | 1 |
| 98 | -CH₂CH₂OH | C—F | 1 |
| 99 | -CH₂CH₂CF₃ | C—F | 1 |
| 100 | cyclopentyl | C—F | 1 |
| 101 | cyclohexyl | C—F | 1 |
| 102 | Ph | C—F | 1 |
| 103 | H | C—OMe | 1 |
| 104 | Methyl | C—OMe | 1 |
| 105 | Ethyl | C—OMe | 1 |
| 106 | Propyl | C—OMe | 1 |
| 107 | Allyl | C—OMe | 1 |
| 108 | i-Propyl | C—OMe | 1 |
| 109 | cyclopropyl | C—OMe | 1 |
| 110 | i-Butyl | C—OMe | 1 |
| 111 | sec-Butyl | C—OMe | 1 |
| 112 | t-Butyl | C—OMe | 1 |
| 113 | cyclobutyl | C—OMe | 1 |
| 114 | -CH₂CH₂OMe | C—OMe | 1 |
| 115 | -CH₂CH₂OH | C—OMe | 1 |
| 116 | -CH₂CH₂CF₃ | C—OMe | 1 |
| 117 | cyclopentyl | C—OMe | 1 |
| 118 | cyclohexyl | C—OMe | 1 |
| 119 | Ph | C—OMe | 1 |
| 120 | H | N | 1 |
| 121 | Methyl | N | 1 |
| 122 | Ethyl | N | 1 |
| 123 | Propyl | N | 1 |
| 124 | Allyl | N | 1 |
| 125 | i-Propyl | N | 1 |
| 126 | cyclopropyl | N | 1 |
| 127 | i-Butyl | N | 1 |
| 128 | sec-Butyl | N | 1 |
| 129 | t-Butyl | N | 1 |
| 130 | cyclobutyl | N | 1 |
| 131 | -CH₂CH₂OMe | N | 1 |
| 132 | -CH₂CH₂OH | N | 1 |
| 133 | -CH₂CH₂CF₃ | N | 1 |
| 134 | cyclopentyl | N | 1 |
| 135 | cyclohexyl | N | 1 |
| 136 | Ph | N | 1 |

In certain embodiments, the invention provides compounds represented by Formula X and pharmaceutically acceptable salts and esters thereof:

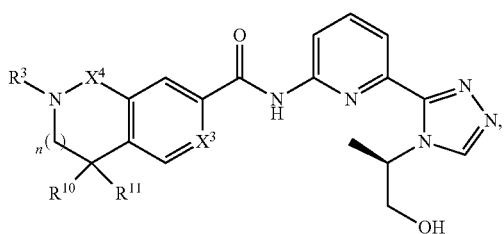

(X)

wherein $R^3$, $R^{10}$, $R^{11}$, $X^3$, $X^4$ and n are as previously defined.

In certain embodiments, the invention provides compounds represented by Formula XI and pharmaceutically acceptable salts and esters thereof:

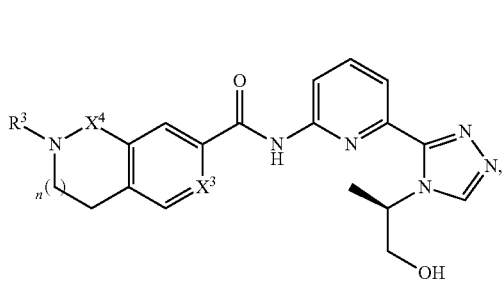

(XI)

wherein $R^3$, $X^3$, $X^4$ and n are as previously defined.

In certain embodiments, the invention provides compounds represented by Formula XII and pharmaceutically acceptable salts and esters thereof:

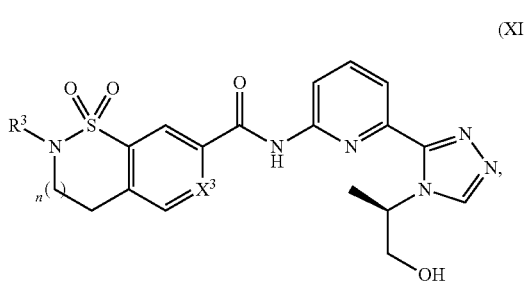

(XII)

wherein $R^3$, $X^3$, and n are as previously defined.

Representative compounds of the invention include, but are not limited to, the following compounds (compound 137 to compound 272 in Table 2) according to Formula XII, and pharmaceutically acceptable salts and esters thereof, wherein $R^3$, $X^3$, and n are delineated for each compound in Table 2.

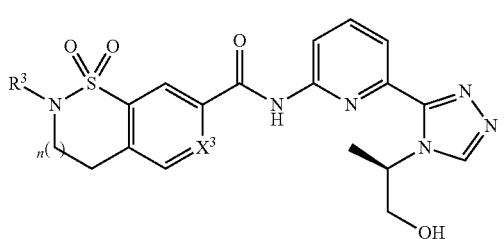

(XII)

TABLE 2

| compound | $R^3$ | $X^3$ | n |
|---|---|---|---|
| 137 | H | C—H | 0 |
| 138 | Methyl | C—H | 0 |
| 139 | Ethyl | C—H | 0 |
| 140 | Propyl | C—H | 0 |
| 141 | Allyl | C—H | 0 |
| 142 | i-Propyl | C—H | 0 |
| 143 | cyclopropyl | C—H | 0 |
| 144 | i-Butyl | C—H | 0 |
| 145 | sec-Butyl | C—H | 0 |
| 146 | t-Butyl | C—H | 0 |
| 147 | cyclobutyl | C—H | 0 |
| 148 | -CH2CH2OMe | C—H | 0 |
| 149 | -CH2CH2OH | C—H | 0 |
| 150 | -CH2CH2CF3 | C—H | 0 |
| 151 | cyclopentyl | C—H | 0 |
| 152 | cyclohexyl | C—H | 0 |
| 153 | -Ph | C—H | 0 |
| 154 | H | C—F | 0 |
| 155 | Methyl | C—F | 0 |
| 156 | Ethyl | C—F | 0 |
| 157 | Propyl | C—F | 0 |
| 158 | Allyl | C—F | 0 |
| 159 | i-Propyl | C—F | 0 |
| 160 | cyclopropyl | C—F | 0 |
| 161 | i-Butyl | C—F | 0 |
| 162 | sec-Butyl | C—F | 0 |
| 163 | t-Butyl | C—F | 0 |
| 164 | cyclobutyl | C—F | 0 |

TABLE 2-continued

| compound | R³ | X³ | n |
|---|---|---|---|
| 165 | -CH2CH2CH2-OMe | C—F | 0 |
| 166 | -CH2CH2CH2-OH | C—F | 0 |
| 167 | -CH2CH2CH2-CF3 | C—F | 0 |
| 168 | -cyclopentyl | C—F | 0 |
| 169 | -cyclohexyl | C—F | 0 |
| 170 | -Ph | C—F | 0 |
| 171 | H | C—OMe | 0 |
| 172 | Methyl | C—OMe | 0 |
| 173 | Ethyl | C—OMe | 0 |
| 174 | Propyl | C—OMe | 0 |
| 175 | Allyl | C—OMe | 0 |
| 176 | i-Propyl | C—OMe | 0 |
| 177 | -cyclopropyl | C—OMe | 0 |
| 178 | i-Butyl | C—OMe | 0 |
| 179 | sec-Butyl | C—OMe | 0 |
| 180 | t-Butyl | C—OMe | 0 |
| 181 | -cyclobutyl | C—OMe | 0 |
| 182 | -CH2CH2CH2-OMe | C—OMe | 0 |
| 183 | -CH2CH2CH2-OH | C—OMe | 0 |
| 184 | -CH2CH2CH2-CF3 | C—OMe | 0 |
| 185 | -cyclopentyl | C—OMe | 0 |
| 186 | -cyclohexyl | C—OMe | 0 |
| 187 | -Ph | C—OMe | 0 |
| 188 | H | N | 0 |
| 189 | Methyl | N | 0 |
| 190 | Ethyl | N | 0 |
| 191 | Propyl | N | 0 |
| 192 | Allyl | N | 0 |
| 193 | i-Propyl | N | 0 |
| 194 | -cyclopropyl | N | 0 |
| 195 | i-Butyl | N | 0 |
| 196 | sec-Butyl | N | 0 |
| 197 | t-Butyl | N | 0 |
| 198 | -cyclobutyl | N | 0 |
| 199 | -CH2CH2CH2-OMe | N | 0 |
| 200 | -CH2CH2CH2-OH | N | 0 |
| 201 | -CH2CH2CH2-CF3 | N | 0 |
| 202 | -cyclopentyl | N | 0 |
| 203 | -cyclohexyl | N | 0 |
| 204 | -Ph | N | 0 |
| 205 | H | C—H | 1 |
| 206 | Methyl | C—H | 1 |
| 207 | Ethyl | C—H | 1 |
| 208 | Propyl | C—H | 1 |
| 209 | Allyl | C—H | 1 |
| 210 | i-Propyl | C—H | 1 |
| 211 | -cyclopropyl | C—H | 1 |

TABLE 2-continued

| compound | R³ | X³ | n |
|---|---|---|---|
| 212 | i-Butyl | C—H | 1 |
| 213 | sec-Butyl | C—H | 1 |
| 214 | t-Butyl | C—H | 1 |
| 215 | cyclobutyl | C—H | 1 |
| 216 | -CH₂CH₂-OMe | C—H | 1 |
| 217 | -CH₂CH₂-OH | C—H | 1 |
| 218 | -CH₂CH₂-CF₃ | C—H | 1 |
| 219 | cyclopentyl | C—H | 1 |
| 220 | cyclohexyl | C—H | 1 |
| 221 | Ph | C—H | 1 |
| 222 | H | C—F | 1 |
| 223 | Methyl | C—F | 1 |
| 224 | Ethyl | C—F | 1 |
| 225 | Propyl | C—F | 1 |
| 226 | Allyl | C—F | 1 |
| 227 | i-Propyl | C—F | 1 |
| 228 | cyclopropyl | C—F | 1 |
| 229 | i-Butyl | C—F | 1 |
| 230 | sec-Butyl | C—F | 1 |
| 231 | t-Butyl | C—F | 1 |
| 232 | cyclobutyl | C—F | 1 |
| 233 | -CH₂CH₂-OMe | C—F | 1 |
| 234 | -CH₂CH₂-OH | C—F | 1 |
| 235 | -CH₂CH₂-CF₃ | C—F | 1 |
| 236 | cyclopentyl | C—F | 1 |
| 237 | cyclohexyl | C—F | 1 |
| 238 | Ph | C—OMe | 1 |
| 239 | H | C—OMe | 1 |
| 240 | Methyl | C—OMe | 1 |
| 241 | Ethyl | C—OMe | 1 |
| 242 | Propyl | C—OMe | 1 |
| 243 | Allyl | C—OMe | 1 |
| 244 | i-Propyl | C—OMe | 1 |
| 245 | cyclopropyl | C—OMe | 1 |
| 246 | i-Butyl | C—OMe | 1 |
| 247 | sec-Butyl | C—OMe | 1 |
| 248 | t-Butyl | C—OMe | 1 |
| 249 | cyclobutyl | C—OMe | 1 |
| 250 | -CH₂CH₂-OMe | C—OMe | 1 |
| 251 | -CH₂CH₂-OH | C—OMe | 1 |
| 252 | -CH₂CH₂-CF₃ | C—OMe | 1 |
| 253 | cyclopentyl | C—OMe | 1 |
| 254 | cyclohexyl | C—OMe | 1 |
| 255 | Ph | C—OMe | 1 |
| 256 | H | N | 1 |
| 257 | Methyl | N | 1 |
| 258 | Ethyl | N | 1 |
| 259 | Propyl | N | 1 |
| 260 | Allyl | N | 1 |
| 261 | i-Propyl | N | 1 |

TABLE 2-continued

| compound | R³ | X³ | n |
|---|---|---|---|
| 262 | cyclopropylmethyl | N | 1 |
| 263 | i-Butyl | N | 1 |
| 264 | sec-Butyl | N | 1 |
| 265 | t-Butyl | N | 1 |
| 266 | cyclobutylmethyl | | |
| 267 | -CH₂CH₂OMe | N | 1 |
| 268 | -CH₂CH₂OH | N | 1 |
| 269 | -CH₂CH₂CF₃ | N | 1 |
| 270 | cyclopentylmethyl | N | 1 |
| 271 | cyclohexylmethyl | N | 1 |
| 272 | -CH₂-Ph | N | 1 |

In certain embodiments, the invention provides compounds represented by Formula XIII and pharmaceutically acceptable salts and esters thereof:

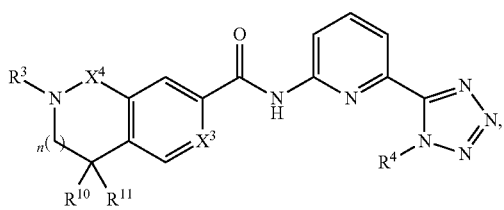

(XIII)

wherein $R^3$, $R^4$, $R^{10}$, $R^{11}$, $X^3$, $X^4$ and n are as previously defined.

In certain embodiments, the invention provides compounds represented by Formula XIV and pharmaceutically acceptable salts and esters thereof:

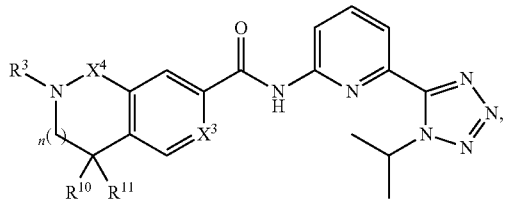

(XIV)

wherein $R^3$, $R^{10}$, $R^{11}$, $X^3$, $X^4$ and n are as previously defined.

In certain embodiments, the invention provides compounds represented by Formula XV and pharmaceutically acceptable salts and esters thereof:

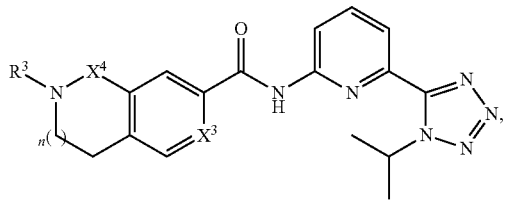

(XV)

wherein $R^3$, $X^3$, $X^4$ and n are as previously defined.

In certain embodiments, the invention provides compounds represented by Formula XVI and pharmaceutically acceptable salts and esters thereof:

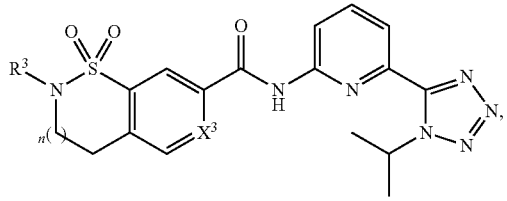

(XVI)

wherein $R^3$, $X^3$, and n are as previously defined.

Representative compounds of the invention include, but are not limited to, the following compounds (compound 273 to compound 408 in Table 3) according to Formula XVI, and pharmaceutically acceptable salts and esters thereof, wherein $R^3$, $X^3$, and n are delineated for each compound in Table 3.

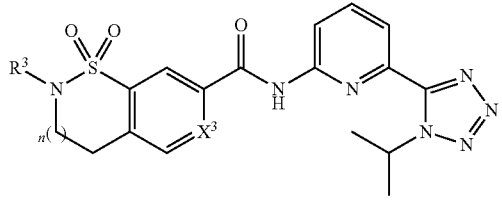

(XVI)

TABLE 3

| compound | R³ | X³ | n |
|---|---|---|---|
| 273 | H | C—H | 0 |
| 274 | Methyl | C—H | 0 |
| 275 | Ethyl | C—H | 0 |
| 276 | Propyl | C—H | 0 |
| 277 | Allyl | C—H | 0 |
| 278 | i-Propyl | C—H | 0 |
| 279 | cyclopropyl | C—H | 0 |
| 280 | i-Butyl | C—H | 0 |
| 281 | sec-Butyl | C—H | 0 |
| 282 | t-Butyl | C—H | 0 |
| 283 | cyclobutyl | C—H | 0 |
| 284 | CH₂CH₂OMe | C—H | 0 |
| 285 | CH₂CH₂OH | C—H | 0 |
| 286 | CH₂CH₂CF₃ | C—H | 0 |
| 287 | cyclopentyl | C—H | 0 |
| 288 | cyclohexyl | C—H | 0 |
| 289 | Ph | C—H | 0 |
| 290 | H | C—F | 0 |
| 291 | Methyl | C—F | 0 |
| 292 | Ethyl | C—F | 0 |
| 293 | Propyl | C—F | 0 |
| 294 | Allyl | C—F | 0 |
| 295 | i-Propyl | C—F | 0 |
| 296 | cyclopropyl | C—F | 0 |
| 297 | i-Butyl | C—F | 0 |
| 298 | sec-Butyl | C—F | 0 |
| 299 | t-Butyl | C—F | 0 |
| 300 | cyclobutyl | C—F | 0 |
| 301 | CH₂CH₂OMe | C—F | 0 |
| 302 | CH₂CH₂OH | C—F | 0 |
| 303 | CH₂CH₂CF₃ | C—F | 0 |
| 304 | cyclopentyl | C—F | 0 |
| 305 | cyclohexyl | C—F | 0 |
| 306 | Ph | C—F | 0 |
| 307 | H | C—OMe | 0 |
| 308 | Methyl | C—OMe | 0 |
| 309 | Ethyl | C—OMe | 0 |
| 310 | Propyl | C—OMe | 0 |
| 311 | Allyl | C—OMe | 0 |
| 312 | i-Propyl | C—OMe | 0 |
| 313 | cyclopropyl | C—OMe | 0 |
| 314 | i-Butyl | C—OMe | 0 |
| 315 | sec-Butyl | C—OMe | 0 |
| 316 | t-Butyl | C—OMe | 0 |
| 317 | cyclobutyl | C—OMe | 0 |
| 318 | CH₂CH₂OMe | C—OMe | 0 |
| 319 | CH₂CH₂OH | C—OMe | 0 |
| 320 | CH₂CH₂CF₃ | C—OMe | 0 |
| 321 | cyclopentyl | C—OMe | 0 |

TABLE 3-continued

| compound | R³ | X³ | n |
|---|---|---|---|
| 322 | cyclohexyl | C—OMe | 0 |
| 323 | CH₂-Ph | C—OMe | 0 |
| 324 | H | N | 0 |
| 325 | Methyl | N | 0 |
| 326 | Ethyl | N | 0 |
| 327 | Propyl | N | 0 |
| 328 | Allyl | N | 0 |
| 329 | i-Propyl | N | 0 |
| 330 | cyclopropyl | N | 0 |
| 331 | i-Butyl | N | 0 |
| 332 | sec-Butyl | N | 0 |
| 333 | t-Butyl | N | 0 |
| 334 | cyclobutyl | N | 0 |
| 335 | CH₂CH₂OMe | N | 0 |
| 336 | CH₂CH₂OH | N | 0 |
| 337 | CH₂CH₂CH₂CF₃ | N | 0 |
| 338 | cyclopentyl | N | 0 |
| 339 | cyclohexyl | N | 0 |
| 340 | CH₂-Ph | N | 0 |
| 341 | H | C—H | 1 |
| 342 | Methyl | C—H | 1 |
| 343 | Ethyl | C—H | 1 |
| 344 | Propyl | C—H | 1 |
| 345 | Allyl | C—H | 1 |
| 346 | i-Propyl | C—H | 1 |
| 347 | cyclopropyl | C—H | 1 |
| 348 | i-Butyl | C—H | 1 |
| 349 | sec-Butyl | C—H | 1 |
| 350 | t-Butyl | C—H | 1 |
| 351 | cyclobutyl | C—H | 1 |
| 352 | CH₂CH₂OMe | C—H | 1 |
| 353 | CH₂CH₂OH | C—H | 1 |
| 354 | CH₂CH₂CH₂CF₃ | C—H | 1 |
| 355 | cyclopentyl | C—H | 1 |
| 356 | cyclohexyl | C—H | 1 |
| 357 | CH₂-Ph | C—H | 1 |
| 358 | H | C—F | 1 |
| 359 | Methyl | C—F | 1 |
| 360 | Ethyl | C—F | 1 |
| 361 | Propyl | C—F | 1 |
| 362 | Allyl | C—F | 1 |
| 363 | i-Propyl | C—F | 1 |
| 364 | cyclopropyl | C—F | 1 |
| 365 | i-Butyl | C—F | 1 |
| 366 | sec-Butyl | C—F | 1 |
| 367 | t-Butyl | C—F | 1 |
| 368 | cyclobutyl | C—F | 1 |
| 369 | CH₂CH₂OMe | C—F | 1 |
| 370 | CH₂CH₂OH | C—F | 1 |
| 371 | CH₂CH₂CH₂CF₃ | C—F | 1 |

TABLE 3-continued

| compound | R³ | X³ | n |
|---|---|---|---|
| 372 | cyclopentyl | C—F | 1 |
| 373 | cyclohexyl | C—F | 1 |
| 374 | —Ph | C—F | 1 |
| 375 | H | C—OMe | 1 |
| 376 | Methyl | C—OMe | 1 |
| 377 | Ethyl | C—OMe | 1 |
| 378 | Propyl | C—OMe | 1 |
| 379 | Allyl | C—OMe | 1 |
| 380 | i-Propyl | C—OMe | 1 |
| 381 | cyclopropyl | C—OMe | 1 |
| 382 | i-Butyl | C—OMe | 1 |
| 383 | sec-Butyl | C—OMe | 1 |
| 384 | t-Butyl | C—OMe | 1 |
| 385 | cyclobutyl | C—OMe | 1 |
| 386 | —CH₂CH₂OMe | C—OMe | 1 |
| 387 | —CH₂CH₂OH | C—OMe | 1 |
| 388 | —CH₂CH₂CF₃ | C—OMe | 1 |
| 389 | cyclopentyl | C—OMe | 1 |
| 390 | cyclohexyl | C—OMe | 1 |
| 391 | —Ph | C—OMe | 1 |
| 392 | H | N | 1 |
| 393 | Methyl | N | 1 |
| 394 | Ethyl | N | 1 |
| 395 | Propyl | N | 1 |
| 396 | Allyl | N | 1 |
| 397 | i-Propyl | N | 1 |
| 398 | cyclopropyl | N | 1 |
| 399 | i-Butyl | N | 1 |
| 400 | sec-Butyl | N | 1 |
| 401 | t-Butyl | N | 1 |
| 402 | cyclobutyl | N | 1 |
| 403 | —CH₂CH₂OMe | N | 1 |
| 404 | —CH₂CH₂OH | N | 1 |
| 405 | —CH₂CH₂CF₃ | N | 1 |
| 406 | cyclopentyl | N | 1 |
| 407 | cyclohexyl | N | 1 |
| 408 | —Ph | N | 1 |

In certain embodiments, the invention provides compounds represented by Formula XVII and pharmaceutically acceptable salts and esters thereof:

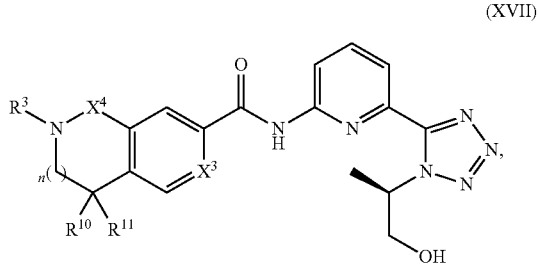

(XVII)

wherein R³, R¹⁰, R¹¹, X³, X⁴ and n are as previously defined.

In certain embodiments, the invention provides compounds represented by Formula XVIII and pharmaceutically acceptable salts and esters thereof:

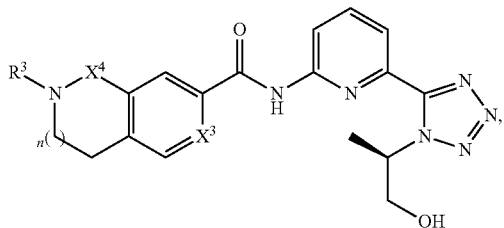

(XVIII)

wherein R³, X³, X⁴ and n are as previously defined.

In certain embodiments, the invention provides compounds represented by Formula XIX and pharmaceutically acceptable salts and esters thereof:

(XIX)

wherein R³, X³, and n are as previously defined.

Representative compounds of the invention include, but are not limited to, the following compounds (compound 409 to compound 544 in Table 4) according to Formula XIX, and pharmaceutically acceptable salts and esters thereof wherein R³, X³, and n are delineated for each compound in Table 4.

(XIX)

TABLE 4

| compound | R³ | X³ | n |
|---|---|---|---|
| 409 | H | C—H | 0 |
| 410 | Methyl | C—H | 0 |
| 411 | Ethyl | C—H | 0 |
| 412 | Propyl | C—H | 0 |
| 413 | Allyl | C—H | 0 |
| 414 | i-Propyl | C—H | 0 |
| 415 | cyclopropyl | C—H | 0 |
| 416 | i-Butyl | C—H | 0 |
| 417 | sec-Butyl | C—H | 0 |
| 418 | t-Butyl | C—H | 0 |
| 419 | cyclobutyl | C—H | 0 |
| 420 | CH₂CH₂OMe | C—H | 0 |
| 421 | CH₂CH₂OH | C—H | 0 |
| 422 | CH₂CH₂CF₃ | C—H | 0 |
| 423 | cyclopentyl | C—H | 0 |
| 424 | cyclohexyl | C—H | 0 |
| 425 | Ph | C—H | 0 |
| 426 | H | C—F | 0 |
| 427 | Methyl | C—F | 0 |
| 428 | Ethyl | C—F | 0 |
| 429 | Propyl | C—F | 0 |
| 430 | Allyl | C—F | 0 |
| 431 | i-Propyl | C—F | 0 |
| 432 | cyclopropyl | C—F | 0 |
| 433 | i-Butyl | C—F | 0 |
| 434 | sec-Butyl | C—F | 0 |
| 435 | t-Butyl | C—F | 0 |
| 436 | cyclobutyl | C—F | 0 |
| 437 | CH₂CH₂OMe | C—F | 0 |
| 438 | CH₂CH₂OH | C—F | 0 |
| 439 | CH₂CH₂CF₃ | C—F | 0 |

TABLE 4-continued

| compound | R³ | X³ | n |
|---|---|---|---|
| 440 | cyclopentyl | C—F | 0 |
| 441 | cyclohexyl | C—F | 0 |
| 442 | —Ph | C—F | 0 |
| 443 | H | C—OMe | 0 |
| 444 | Methyl | C—OMe | 0 |
| 445 | Ethyl | C—OMe | 0 |
| 446 | Propyl | C—OMe | 0 |
| 447 | Allyl | C—OMe | 0 |
| 448 | i-Propyl | C—OMe | 0 |
| 449 | cyclopropyl | C—OMe | 0 |
| 450 | i-Butyl | C—OMe | 0 |
| 451 | sec-Butyl | C—OMe | 0 |
| 452 | t-Butyl | C—OMe | 0 |
| 453 | cyclobutyl | C—OMe | 0 |
| 454 | -CH₂CH₂-OMe | C—OMe | 0 |
| 455 | -CH₂CH₂-OH | C—OMe | 0 |
| 456 | -CH₂CH₂CH₂-CF₃ | C—OMe | 0 |
| 457 | cyclopentyl | C—OMe | 0 |
| 458 | cyclohexyl | C—OMe | 0 |
| 459 | —Ph | C—OMe | 0 |
| 460 | H | N | 0 |
| 461 | Methyl | N | 0 |
| 462 | Ethyl | N | 0 |
| 463 | Propyl | N | 0 |
| 464 | Allyl | N | 0 |
| 465 | i-Propyl | N | 0 |
| 466 | cyclopropyl | N | 0 |
| 467 | i-Butyl | N | 0 |
| 468 | sec-Butyl | N | 0 |
| 469 | t-Butyl | N | 0 |
| 470 | cyclobutyl | N | 0 |
| 471 | -CH₂CH₂-OMe | N | 0 |
| 472 | -CH₂CH₂-OH | N | 0 |
| 473 | -CH₂CH₂CH₂-CF₃ | N | 0 |
| 474 | cyclopentyl | N | 0 |
| 475 | cyclohexyl | N | 0 |
| 476 | —Ph | N | 0 |
| 477 | H | C—H | 1 |
| 478 | Methyl | C—H | 1 |
| 479 | Ethyl | C—H | 1 |
| 480 | Propyl | C—H | 1 |
| 481 | Allyl | C—H | 1 |
| 482 | i-Propyl | C—H | 1 |
| 483 | cyclopropyl | C—H | 1 |
| 484 | i-Butyl | C—H | 1 |
| 485 | sec-Butyl | C—H | 1 |
| 486 | t-Butyl | C—H | 1 |
| 487 | cyclobutyl | C—H | 1 |
| 488 | -CH₂CH₂-OMe | C—H | 1 |
| 489 | -CH₂CH₂-OH | C—H | 1 |

TABLE 4-continued

| compound | R³ | X³ | n |
|---|---|---|---|
| 490 | –CH₂CH₂CF₃ | C—H | 1 |
| 491 | cyclopentyl | C—H | 1 |
| 492 | cyclohexyl | C—H | 1 |
| 493 | –Ph | C—H | 1 |
| 494 | H | C—F | 1 |
| 495 | Methyl | C—F | 1 |
| 496 | Ethyl | C—F | 1 |
| 497 | Propyl | C—F | 1 |
| 498 | Allyl | C—F | 1 |
| 499 | i-Propyl | C—F | 1 |
| 500 | cyclopropyl | C—F | 1 |
| 501 | i-Butyl | C—F | 1 |
| 502 | sec-Butyl | C—F | 1 |
| 503 | t-Butyl | C—F | 1 |
| 504 | cyclobutyl | C—F | 1 |
| 505 | –CH₂CH₂OMe | C—F | 1 |
| 506 | –CH₂CH₂OH | C—F | 1 |
| 507 | –CH₂CH₂CF₃ | C—F | 1 |
| 508 | cyclopentyl | C—F | 1 |
| 509 | cyclohexyl | C—F | 1 |
| 510 | –Ph | C—F | 1 |
| 511 | H | C—OMe | 1 |
| 512 | Methyl | C—OMe | 1 |
| 513 | Ethyl | C—OMe | 1 |
| 514 | Propyl | C—OMe | 1 |
| 515 | Allyl | C—OMe | 1 |
| 516 | i-Propyl | C—OMe | 1 |
| 517 | cyclopropyl | C—OMe | 1 |
| 518 | i-Butyl | C—OMe | 1 |
| 519 | sec-Butyl | C—OMe | 1 |
| 520 | t-Butyl | C—OMe | 1 |
| 521 | cyclobutyl | C—OMe | 1 |
| 522 | –CH₂CH₂OMe | C—OMe | 1 |
| 523 | –CH₂CH₂OH | C—OMe | 1 |
| 524 | –CH₂CH₂CF₃ | C—OMe | 1 |
| 525 | cyclopentyl | C—OMe | 1 |
| 526 | cyclohexyl | C—OMe | 1 |
| 527 | –Ph | C—OMe | 1 |
| 528 | H | N | 1 |
| 529 | Methyl | N | 1 |
| 530 | Ethyl | N | 1 |
| 531 | Propyl | N | 1 |
| 532 | Allyl | N | 1 |
| 533 | i-Propyl | N | 1 |
| 534 | cyclopropyl | N | 1 |
| 535 | i-Butyl | N | 1 |
| 536 | sec-Butyl | N | 1 |
| 537 | t-Butyl | N | 1 |
| 538 | cyclobutyl | N | 1 |
| 539 | –CH₂CH₂OMe | N | 1 |

TABLE 4-continued

| compound | R³ | X³ | n |
|---|---|---|---|
| 540 | —CH₂CH₂OH | N | 1 |
| 541 | —CH₂CH₂CF₃ | N | 1 |
| 542 | cyclopentyl | N | 1 |
| 543 | cyclohexyl | N | 1 |
| 544 | —Ph | N | 1 |

In certain embodiments, the present invention provides a method for the treatment of an ASK-1 mediated disease or condition. The method comprises administering a therapeutically effective amount of a compound of Formula (I) or a pharmaceutically acceptable salt or ester thereof. The present invention also provides the use of a compound of Formula (I) or a pharmaceutically acceptable salt or ester thereof for the preparation of a medicament for the treatment of an ASK-1 mediated disease or condition.

In certain embodiments, the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, reperfusion/ischemia in stroke, cardiac hypertrophy, respiratory diseases, heart attacks, or myocardial ischemia.

In certain embodiments, the metabolic disease is insulin resistance, Type I and Type II diabetes, or obesity.

In certain embodiments, the chronic kidney disease is polycystic kidney disease, pyelonephritis, kidney fibrosis and glomerulonephritis.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl" as used herein, refers to saturated, straight- or branched-chain hydrocarbon radicals. Suitable alkyl groups include "$C_1$-$C_3$ alkyl," "$C_1$-$C_6$ alkyl," "$C_1$-$C_{10}$ alkyl", "$C_2$-$C_4$ alkyl," or "$C_3$-$C_6$ alkyl," which refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. Suitable alkenyl groups include "$C_2$-$C_{10}$ alkenyl," "$C_2$-$C_8$ alkenyl," "$C_2$-$C_4$ alkenyl," or "$C_3$-$C_6$ alkenyl," which refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. Suitable alkynyl groups include "$C_2$-$C_{10}$ alkynyl," "$C_2$-$C_8$ alkynyl," "$C_2$-$C_4$ alkynyl," or "$C_3$-$C_6$ alkynyl," which refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but are not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but are not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted. The term "bicyclic aryl" or "bicyclic heteroaryl" refers to a ring system consisting of two rings wherein at least one ring is aromatic; and the two rings can be fused or covalently attached.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

The term "alkylene" as used herein, refers to a diradical of a branched or unbranched saturated hydrocarbon chain, typically having from 1 to 20 carbon atoms (e.g. 1-10 carbon atoms, or 1, 2, 3, 4, 5, or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —NO$_2$, —CN, —NH$_2$, N$_3$, protected amino, alkoxy, thioalkoxy, oxo, $C_1$-$C_{12}$-alkyl, $C_2$-$C_{12}$-alkenyl, —C$_2$-C$_{12}$-alkynyl-halo-C$_1$-C$_{12}$-alkyl, -halo-C$_2$-C$_{12}$-alkenyl, -halo-C$_2$-C$_{12}$-alkynyl, -halo-C$_3$-C$_{12}$-cycloalkyl, —NH—C$_1$-C$_{12}$-alkyl, —NH—C$_2$-C$_{12}$-alkenyl, —NH—C$_2$-C$_{12}$-alkynyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-heteroaryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH— heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkynyl, —OCONH—C$_3$-C$_{12}$-cycloalkyl, —OCONH-aryl, —OCONH— heteroaryl, —OCONH— heterocycloalkyl, —NHC(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkylalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy, —CN; —OH; NH$_2$; $C_1$-$C_4$-alkylamino; di($C_1$-$C_4$-alkyl) amino; and NO$_2$. It is understood that the aryls, heteroaryls, alkyls, and the like can be further substituted. In some cases, each substituent in a substituted moiety is additionally optionally substituted with one or more groups, each group being independently selected from $C_1$-$C_6$-alkyl, —F, —Cl, —Br, —I, —OH, —NO$_2$, —CN, and —NH$_2$. Preferably, a substituted alkyl group, such as a substituted methyl group, is substituted with one or more halogen atoms, more preferably one or more fluorine or chlorine atoms.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "cyclic" as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "aryloxy" refers to the group aryl-O— wherein the aryl group is as defined above, and includes optionally substituted aryl groups as also defined above. The term "arylthio" refers to the group R—S—, where R is as defined for aryl.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein can contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but are not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2,* (Biotechnology: Pharmaceutical Aspects), edited by V. J. Stella, et al, Springer and AAPSPress, 2007, pp 31-99.

The term "amino" as used herein, refers to the group —$NH_2$.

The term "substituted amino" as used herein, refers to the group —NRR where each R is independently selected from the group consisting of hydrogen, alkyl, cycloalkyl, aryl, heteroaryl and heterocycloalkyl provided that both R groups are not hydrogen, or a group —Y—Z, in which Y is optionally substituted alkylene and Z is alkenyl, cycloalkenyl, or alkynyl.

The term "amino protecting group" as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Oranic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which have been used in the descriptions of the schemes and the examples that follow are:
Alloc for allyloxycarbonyl;
Alloc-Cl for allyl chloroformate;
ASK1 for apoptosis signal-regulating kinase 1;
ATP for adenosine triphosphate;
Boc for tert-butyloxycarbonyl;
BOP—Cl for bis(2-oxo-3-oxazolidinyl)phosphinic chloride;
Cbz for benzyloxycarbonyl;
Cbz-Cl for benzyl chloroformate;
CDI for carbonyldiimidazole;
$(COCl)_2$ for oxalyl chloride;
DBU for 1,8-diazabicycloundec-7-ene;
DCC for N,N-dicyclohexylcarbodiimide;
1,2-DCE for 1,2-dichloroethane;
DCM for dichloromethane;
DIPEA or Hunig's base or i-$Pr_2$NEt for N,N-diisopropylethylamine;
DMAc for N,N-dimethylacetamide;
DMAP for N,N-dimethylaminopyridine;
DMF for N,N-dimethyl formamide;
EDC for 1-(3-diethylaminopropyl)-3-ethylcarbodiimide hydrochloride;
EGTA for ethylene glycol-bis(2-aminoethylether)-N,N,N',N'-tetraacetic acid;
ESI for electrospray ionization;
$Et_3N$ or TEA for triethylamine;
$Et_2O$ for diethylether;
EtOAc for ethyl acetate;
Ghosez's Reagent for 1-chloro-N,N,2-trimethyl-1-propenylamine;
HATU for 1-[bis(dimethylamino)methylene]-1H-1,2,3-triazolo[4,5-b]pyridinium 3-oxide hexafluorophosphate;
HEPES for 4-(2-Hydroxyethyl)piperazine-1-ethanesulfonic acid, N-(2-Hydroxyethyl)piperazine-N'-(2-ethanesulfonic acid);
$IC_{50}$ for half maximal inhibitory concentration;
KOt-Bu for potassium tert-butoxide;
LCMS for liquid chromatography-mass spectrometry;
MeCN for acetonitrile;
MTBE for methyl tert-butyl ether;
m/z for mass-to-charge ratio;
NaOt-Bu for sodium tert-butoxide;
NBS for N-bromosuccinimide;
NMP for 1-methyl-2-pyrrolidinone;
NMR for nuclear magnetic resonance spectroscopy;
OMs or mesylate for methanesulfonate;
OTf or triflate for trifluoromethanesulfonate;
OTs or tosylate for para-toluenesulfonate;
$Pd_2(dba)_3$ for tris(dibenzylideneacetone)dipalladium(0);
P(o-tolyl)$_3$ for tri(o-tolyl)phosphine;
PyAOP for 7-azabenzotriazol-1-yloxy)tripyrrolidinophosphonium hexafluorophosphate;

PyBOP for benzotriazol-1-yl-oxytripyrrolidinophosphonium hexafluorophosphate;

STK3 for serine/threonine-protein kinase 3;

TEA for triethylamine;

THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

For the preparation of compounds of Formula (1-1), wherein $R^4$ is as previously defined, see US 2014/0018370.

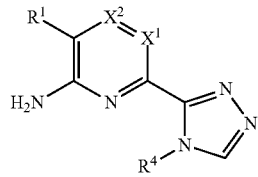

(1-1)

As shown in Scheme 1, compounds of Formula (1-5), wherein $R^4$ is as previously defined, are prepared from a compound of Formula (1-2). Thus, the compound of Formula (1-2) is reacted with a primary amine ($R^4$—$NH_2$) in the presence of a suitable coupling reagent such as, but not limited to, BOP—Cl, CDI, DCC, EDC, HATU, PyAOP or PyBOP in combination with a suitable base such as, but not limited to, $Et_3N$ or DIPEA to afford a compound of Formula (1-3). The reaction solvent can be, but is not limited to, THF, DCM and DMF. The reaction temperature is from −20° C. to 40° C. The compound of Formula (1-3) is reacted with a suitable triflating reagent, such as, but not limited to, $Tf_2O$, in combination with a suitable azide source, such as, but not limited to, $NaN_3$ or $TMSN_3$ to afford a compound of Formula (1-4). The reaction solvent can be, but is not limited to, MeCN. The reaction temperature is from −20° C. to 40° C. The compound of Formula (1-4) is reduced in the presence of hydrogen gas, and a suitable metal catalyst, such as, but not limited to, Pd/C to afford a compound of Formula (1-5). The reaction solvent can be, but is not limited to, MeOH, EtOH, EtOAc, or a combination thereof.

Scheme 1

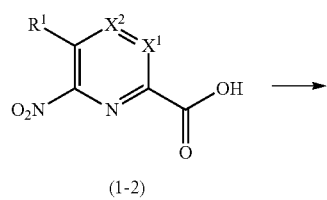

(1-2)

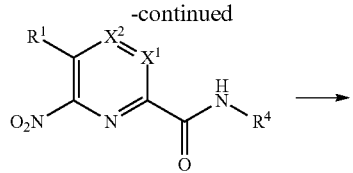

(1-3)

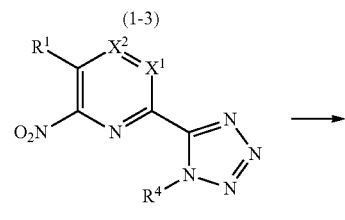

(1-4)

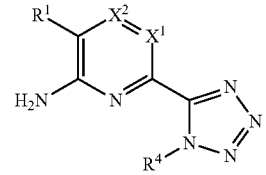

(1-5)

As shown in Scheme 2, novel analogs of the compound of Formula (Ic-1) are prepared from the compound of Formula (2-1), wherein $X^3$ is as previously defined. Thus, the compound of Formula (2-1) is reacted with a primary amine ($R^3$—$NH_2$) to afford a compound of Formula (2-2), wherein $R^3$ is as previously defined, using a suitable base such as, but not limited to, $Et_3N$, DIPEA, DMAP, or pyridine. The reaction solvent can be, but is not limited to, THF or DCM. The reaction temperature is from −20° C. to 40° C. The compound of Formula (2-2) is brominated to afford a compound of Formula (2-3) using a suitable brominating reagent such as, but not limited to, NBS in combination with a free radical initiator reagent such as, but not limited to, AIBN or benzoyl peroxide. The reaction solvent can be, but is not limited to, $CCl_4$. The reaction temperature is from room temperature to 80° C. The compound of Formula (2-3) is reacted with a suitable base such as, but not limited to, NaH to afford a compound of Formula (2-4). The reaction solvent can be, but is not limited to, THF or DMF. The reaction temperature is from −20° C. to 40° C. The compound of Formula (2-4) is reacted with carbon monoxide, ethanol, a suitable base, such as, but not limited to, $Et_3N$, DIPEA, DMAP, or pyridine, a suitable palladium(II) catalyst, such as, but not limited to, $Pd(OAc)_2$ or $PdCl_2$, and a catalytic quantity of a phosphine ligand, such as, but not limited to, $PPh_3$, $Ph_2P(CH_2)_3PPh_2$, or $Ph_2P(CH_2)_4PPh_2$. The reaction solvent can be, but is not limited to, DMF or DMPU. The reaction temperature is from room temperature to 120° C. The compound of Formula (2-5) is hydrolyzed to afford a compound of Formula (2-6) using a suitable hydroxide source such as, but not limited to, NaOH or LiOH. Alternatively, a compound of Formula (2-4) can be reacted with a halogen-metal exchange reagent, such as, but not limited to, i-PrMgCl or n-BuLi in combination with $CO_2$ to afford a compound of Formula (2-6). The reaction solvent can be, but is not limited to, THF. The reaction temperature is from −80° C. to room temperature. The compound of Formula (2-6) is reacted with a suitable chlorinating reagent such as, but not limited to, oxalyl chloride, thionyl chloride, or Ghosez's reagent to afford a compound of Formula (2-7). The reaction solvent can be, but is not limited to, THF or DCM. The reaction temperature is from −20° C. to 40° C. The compound of Formula (2-7) is reacted with a compound of Formula (2-8), wherein $X^1$, $X^2$, $R^1$ and $R^2$ are as previously defined, to afford compounds of Formula (Ic-1) using a suitable base such as, but not limited to, Et$_3$N, DMAP, pyridine, or DIPEA. The reaction solvent can be, but is not limited to, THF, DCM, pyridine and toluene. The reaction temperature is from −20° C. to 40° C. Alternatively, the compound of Formula (2-6) is reacted with a compound of Formula (2-8) to afford compounds of Formula (Ic-1) using a suitable coupling reagent such as, but not limited to, BOP—Cl, CDI, DCC, EDC, HATU, PyAOP or PyBOP in the presence of a suitable base such as, but not limited to, Et$_3$N or DIPEA. The reaction solvent can be, but is not limited to, THF, DCM and DMF. The reaction temperature is from −20° C. to 40° C.

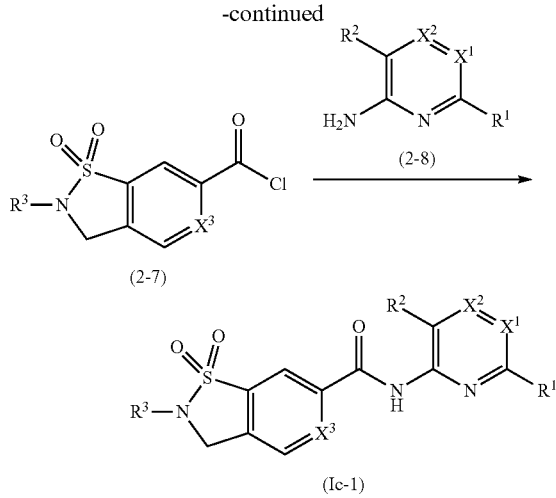

As shown in Scheme 3, the compound of Formula (2-4) can alternatively be prepared from the compound of Formula (3-1), wherein $X^3$ is as previously defined. Thus, the compound of Formula (3-1) is reacted with a suitable combination of oxidants, such as, but not limited to, $H_5IO_6$ and $CrO_3$ to afford a compound of Formula (3-2). The solvent can be, but is not limited to, MeCN. The reaction temperature is from room temperature to 100° C. The compound of Formula (3-2) is alkylated with a suitable alkylating reagent, such as, but not limited to, $R^3$—Cl, $R^3$—Br, $R^3$—I, $R^3$—OTs, and $R^3$—OMs in the presence of a suitable base, such as, but not limited to, NaH to afford a compound of Formula (3-3). The solvent can be, but is not limited to DMF or THF. The reaction temperature is from −20° C. to 180° C. The compound of Formula (3-3) is reacted with a suitable reducing reagent, such as, but not limited to, BH$_3$.DMS, or BH$_3$.THF to afford a compound of Formula (2-4). The reaction solvent can be, but is not limited to THF. The reaction temperature is from −78° C. to 80° C.

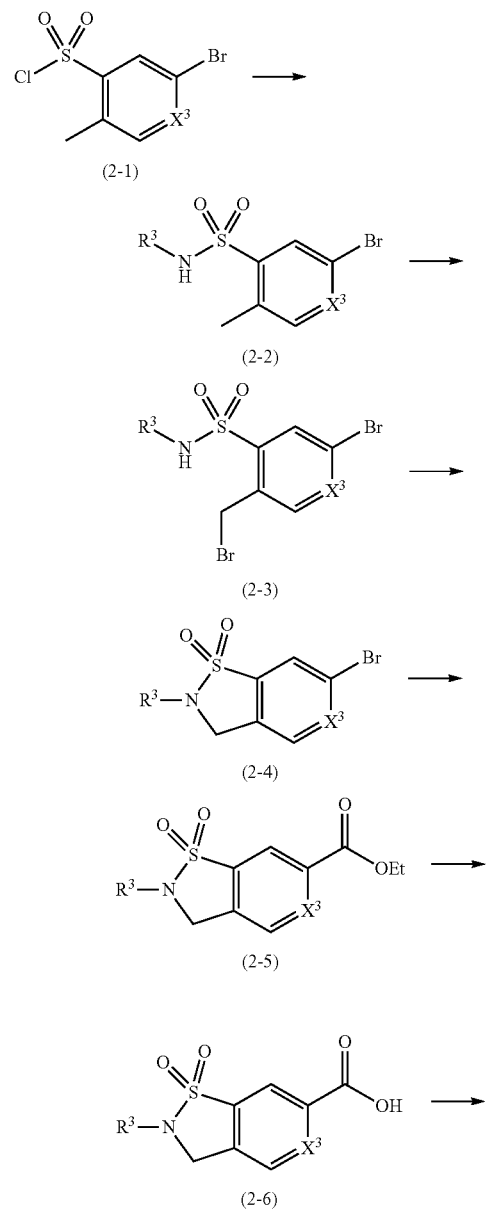

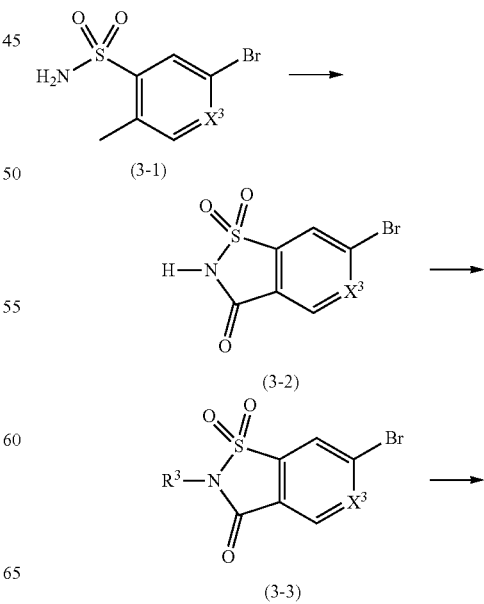

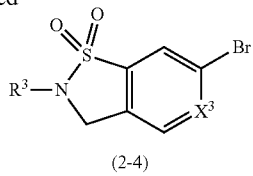

(2-4)

As shown in Scheme 4, novel analogs of the compound of Formula (Ic-2) are prepared from the compound of Formula (2-2), wherein X³ is as previously defined. Thus, the compound of Formula (2-2) is brominated to afford a compound of Formula (4-1) using a suitable brominating reagent such as, but not limited to, NBS in combination with a free radical initiator reagent such as, but not limited to, AIBN or benzoyl peroxide. The reaction solvent can be, but is not limited to, CCl₄. The reaction temperature is from room temperature to 80° C. The compound of Formula (4-1) is hydrolyzed to afford a compound of Formula (4-2) using water in combination with a suitable silver salt, such as, but not limited to, AgNO₃. The reaction solvent can be, but is not limited to, THF. The reaction temperature is from room temperature to 100° C. The compound of Formula (4-2) is reacted with (methoxymethyl)triphenylphosphonium chloride in combination with a suitable base, such as, but not limited to, NaHMDS, LiHMDS, KHMDS, or LDA to afford a compound of Formula (4-3). The reaction solvent can be, but is not limited to, THF. The reaction temperature is from −80° C. to room temperature. The compound of Formula (4-3) is reacted with a strong aqueous acid, such as, but not limited to, HCl$_{(aq)}$ to afford a compound of Formula (4-4). The reaction solvent can be, but is not limited to, THF. The reaction temperature is from room temperature to 80° C. The compound of Formula (4-4) is reduced in the presence of hydrogen gas, and a suitable metal catalyst, such as, but not limited to, PtO₂ to afford a compound of Formula (4-5). The reaction solvent can be, but is not limited to, MeOH, EtOH, EtOAc, or a combination thereof. The compound of Formula (4-5) is reacted with carbon monoxide, ethanol, a suitable base, such as, but not limited to, Et₃N, DIPEA, DMAP, or pyridine, a suitable palladium(II) catalyst, such as, but not limited to, Pd(OAc)₂ or PdCl₂, and a catalytic quantity of a phosphine ligand, such as, but not limited to, PPh₃, Ph₂P(CH₂)₃PPh₂, or Ph₂P(CH₂)₄PPh₂ to afford a compound of Formula (4-6). The reaction solvent can be, but is not limited to, DMF or DMPU. The reaction temperature is from room temperature to 120° C. The compound of Formula (4-6) is hydrolyzed to afford a compound of Formula (4-7) using a suitable hydroxide source such as, but not limited to, NaOH or LiOH. Alternatively, a compound of Formula (4-5) can be reacted with a halogen-metal exchange reagent, such as, but not limited to, i-PrMgCl or n-BuLi in combination with CO₂ to afford a compound of Formula (4-7). The reaction solvent can be, but is not limited to, THF. The reaction temperature is from −80° C. to room temperature. The compound of Formula (4-7) is reacted with a suitable chlorinating reagent such as, but not limited to, oxalyl chloride, thionyl chloride, or Ghosez's reagent to afford a compound of Formula (4-8). The reaction solvent can be, but is not limited to, THF or DCM. The reaction temperature is from −20° C. to 40° C. The compound of Formula (4-8) is reacted with a compound of Formula (2-8), wherein X¹, X², R¹ and R² are as previously defined, to afford compounds of Formula (Ic-2) using a suitable base such as, but not limited to, Et₃N, DMAP, pyridine, or DIPEA. The reaction solvent can be, but is not limited to, THF, DCM, pyridine and toluene. The reaction temperature is from −20° C. to 40° C. Alternatively, the compound of Formula (4-7) is reacted with a compound of Formula (2-8) to afford compounds of Formula (Ic-2) using a suitable coupling reagent such as, but not limited to, BOP—Cl, CDI, DCC, EDC, HATU, PyAOP or PyBOP in the presence of a suitable base such as, but not limited to, Et₃N or DIPEA. The reaction solvent can be, but is not limited to, THF, DCM and DMF. The reaction temperature is from −20° C. to 40° C.

Scheme 4

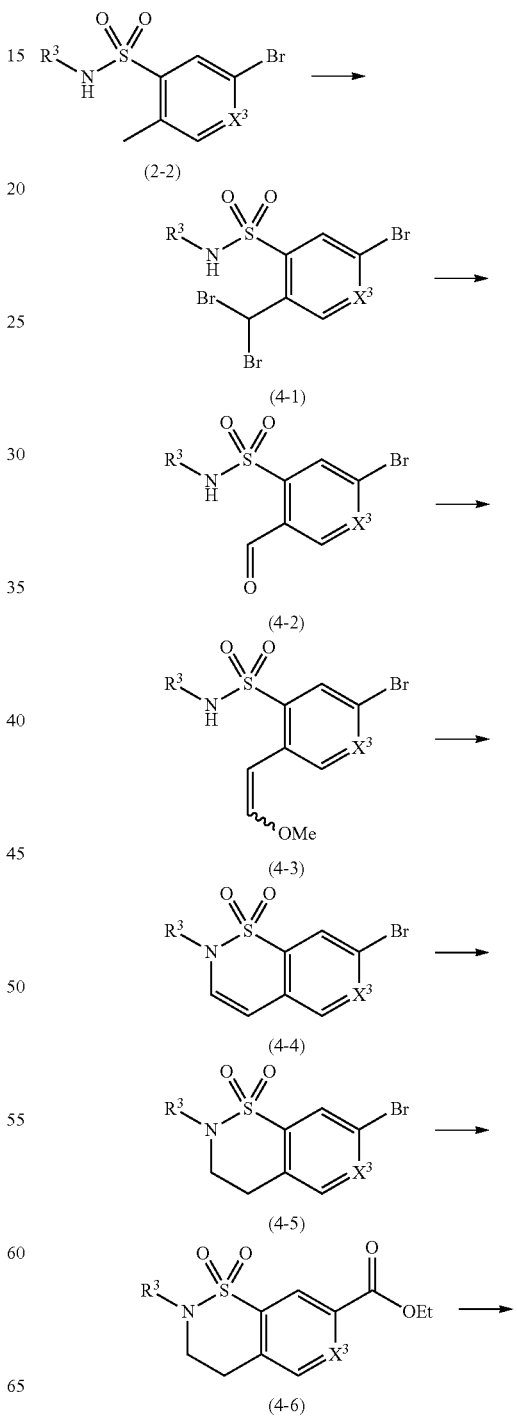

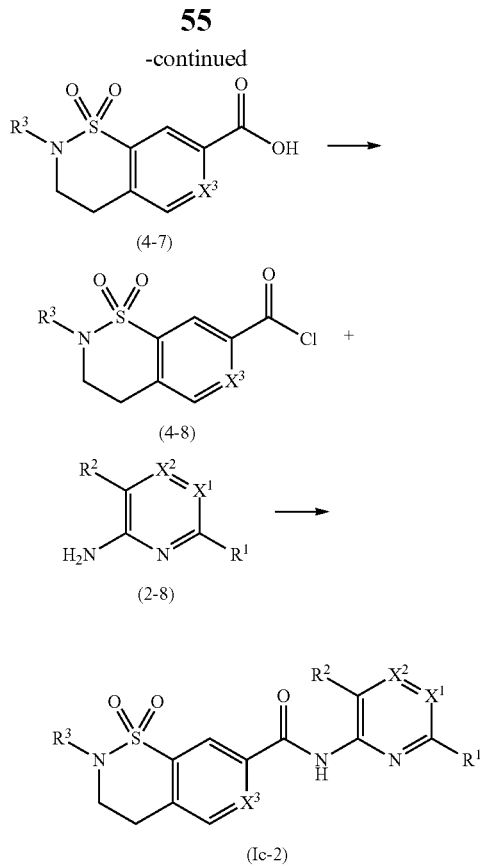

(4-7)

(4-8)

(2-8)

(Ic-2)

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Example 1: 2-(tert-butyl)-5-fluoro-N-(6-(1-isopropyl-1H-tetrazol-5-yl)pyridin-2-yl)-2,3-dihydrobenzo[d]isothiazole-6-carboxamide 1,1-dioxide

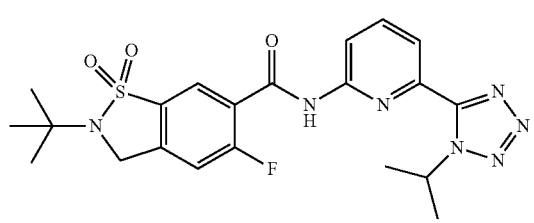 [SMILES: CC(C)n1nnnc1-c1cccc(NC(=O)c2cc3c(cc2F)CN(C(C)(C)C)S3(=O)=O)n1]

1

Step 1-1: Synthesis of N-isopropyl-6-nitropicolinamide

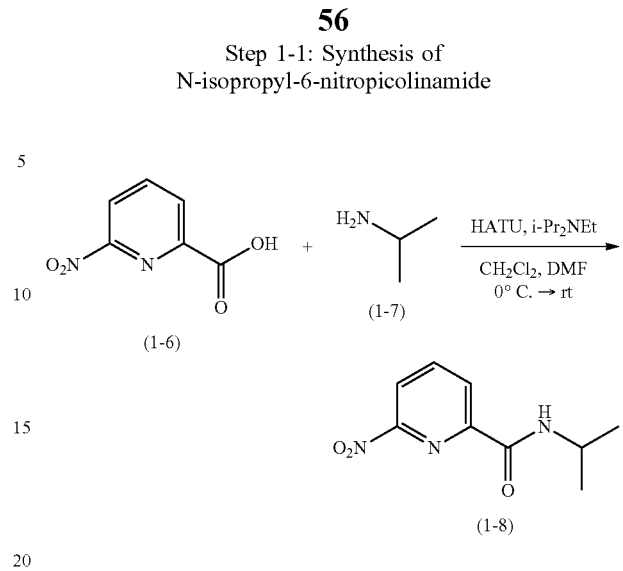

Hunig's base (24.9 mL, 143 mmol, 2.0 eq) was added to a suspension of 6-nitropicolinic acid (1-6) (12.0 g, 71.4 mmol, 1.0 eq) in DCM (198 mL) and DMF (40 mL) at 0° C. Isopropylamine (1-7) (8 mL, 93 mmol, 1.3 eq) was added, followed by HATU (30 g, 79 mmol, 1.1 eq) and the reaction was stirred for 5 hrs at 0° C. The reaction was quenched with brine/water (300 mL) and diluted with DCM (200 mL). The layers were separated and the organic layer was washed with water (200 mL) and brine (200 mL). The organic layer was dried (MgSO$_4$), filtered, and concentrated under reduced pressure. The resultant crude material was purified by column chromatography eluting with hexanes/EtOAc (0% EtOAc→40% EtOAc) to afford pure compound (1-8) (11.5 g, 55.0 mmol, 77%): $^1$H NMR (400 MHz, Chloroform-d) δ 8.58 (dd, J=7.7, 1.0 Hz, 1H), 8.36 (dd, J=8.0, 1.0 Hz, 1H), 8.21 (t, J=7.8 Hz, 1H), 7.71 (br s, 1H), 4.35-r.26 (m, 1H), 1.33 (d, J=6.6 Hz, 6H).

Step 1-2: Synthesis of 2-(1-isopropyl-1H-tetrazol-5-yl)-6-nitropyridine

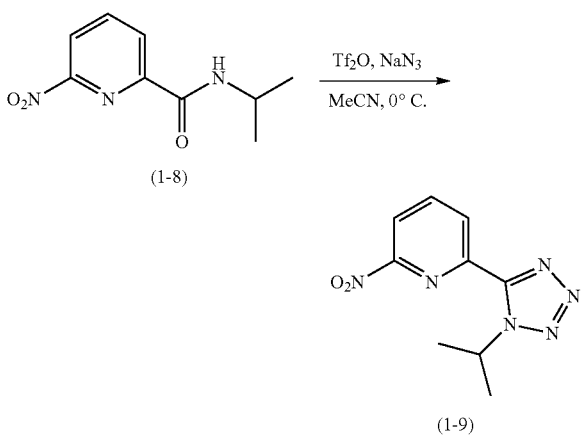

Tf$_2$O (48.7 mL of a 1.0 M solution in DCM, 48.7 mmol, 1.0 eq) was added dropwise over 45 minutes to a mixture of compound (1-8) (10.2 g, 48.7 mmol, 1.0 eq) and NaN$_3$ (3.2 g, 48.7 mmol, 1.0 eq) in CH$_3$CN (108 mL) at 0° C. and the reaction was stirred for 1 hr at 0° C. An additional quantity of NaN$_3$ (0.5 g, 7.31 mmol, 0.15 eq) and Tf$_2$O (7.3 mL, 7.31 mmol, 0.15 eq) was added, and the reaction was stirred a further 30 minutes at 0° C. The reaction was quenched with sat. NaHCO₃ (200 mL) at 0° C., and stirred for 2 hrs at 0° C. The resulting mixture was diluted with H₂O (100 mL) and EtOAc (200 mL). The layers were separated and the aqueous layer was extracted with EtOAc (2×). The combined organic layers were washed with sat. NaHCO₃ and brine, then dried (MgSO₄), filtered, and concentrated under reduced pressure. The resultant crude material was purified by column chromatography eluting with DCM/MeOH to afford pure compound (1-9) (6.84 g, 29.2 mmol, 60%): ¹H NMR (400 MHz, Chloroform-d) δ 8.77 (dd, J=7.8, 0.9 Hz, 1H), 8.41 (dd, J=8.1, 0.9 Hz, 1H), 8.30 (t, J=7.9 Hz, 1H), 5.98 (hept, J=6.7 Hz, 1H), 1.75 (d, J=6.7 Hz, 6H).

Step 1-3: Synthesis of 6-(1-isopropyl-1H-tetrazol-5-yl)pyridin-2-amine

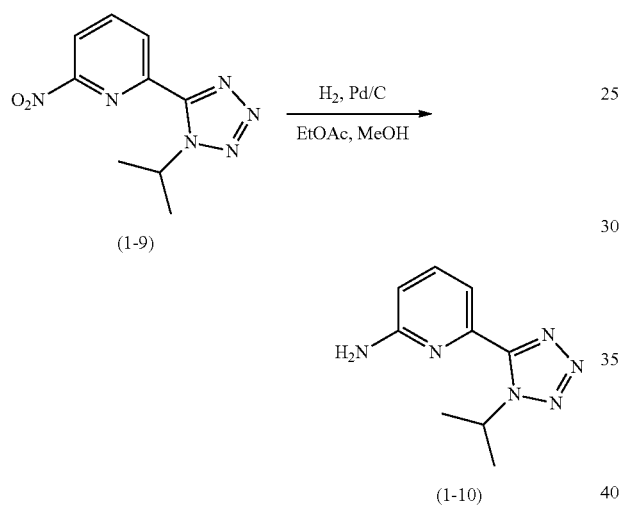

Pd/C (454 mg of a 10% weight % mixture) was added to a solution of compound (1-9) (5.0 g, 21.4 mmol, 1.0 eq) in MeOH (21.4 mL) and EtOAc (21.4 mL). The reaction was evacuated and backfilled with an H₂ balloon (3×) and stirred under an atmosphere of H₂ overnight. The reaction was filtered and concentrated under reduced pressure to afford pure compound (1-10) (4.3 g, 21.1 mmol, 99%): ¹H NMR (400 MHz, Chloroform-d) δ 7.68-7.58 (comp, 2H), 6.64 (dd, J=6.9, 2.2 Hz, 1H), 5.85 (hept, J=6.7 Hz, 1H), 4.61 (br s, 2H), 1.65 (d, J=6.7 Hz, 6H).

Step 1-4: Synthesis of 5-bromo-N-(tert-butyl)-4-fluoro-2-methylbenzenesulfonamide

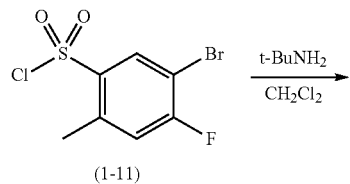

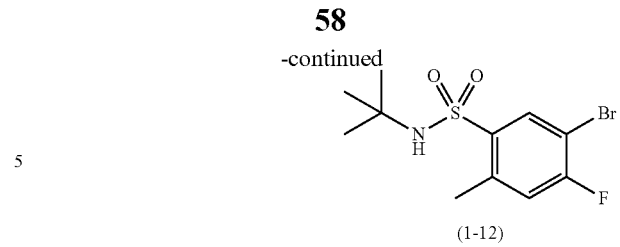

tert-butylamine (1.7 mL, 15.7 mmol, 3.0 eq) was added to a solution of compound (1-11) (1.5 g, 5.2 mmol, 1.0 eq) in DCM (29.0 mL) and the reaction was stirred overnight. The reaction was concentrated under reduced pressure to give a yellow solid that was triturated with H₂O, filtered, and dried under vacuum to afford compound (1-12) (1.6 g, 5.0 mmol, 96%) as a tan solid: ¹H NMR (400 MHz, Chloroform-d) δ 8.24 (d, J=6.9 Hz, 1H), 7.06 (dd, J=8.9, 0.8 Hz, 1H), 4.49 (s, 1H), 2.60 (s, 3H), 1.24 (s, 9H).

Step 1-5: Synthesis of 5-bromo-2-(bromomethyl)-N-(tert-butyl)-4-fluorobenzenesulfonamide and 5-bromo-N-(tert-butyl)-2-(dibromomethyl)-4-fluorobenzenesulfonamide

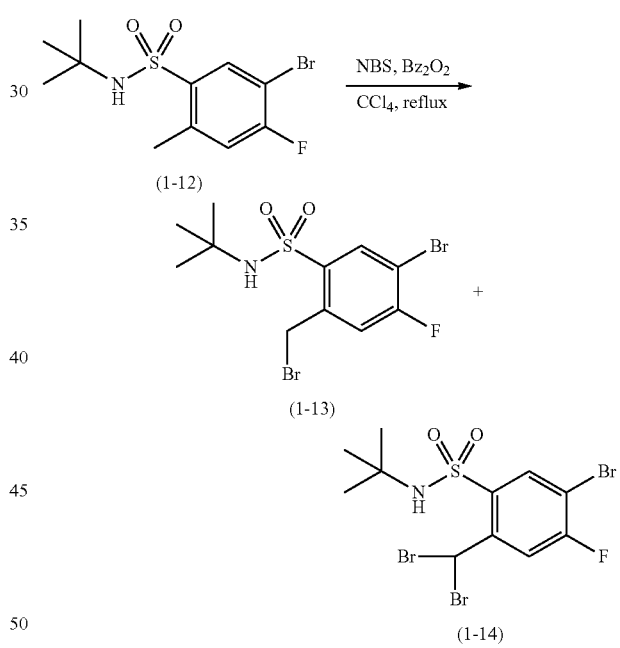

Benzoyl peroxide (0.12 g, 0.50 mmol, 0.10 eq) and NBS (0.89 g, 5.0 mmol, 1.0 eq) were added to a suspension of compound (1-12) (1.6 g, 5.0 mmol, 1.0 eq) in CCl₄ (26 mL) and the reaction was heated at reflux overnight. The reaction was concentrated under reduced pressure. The resultant yellow oil was purified by column chromatography eluting with hexanes/EtOAc (0% EtOAc→10% EtOAc) to afford pure compound (1-13) (1.14 g, 2.83 mmol, 57%) as a colorless solid and pure compound (2-12) (376 mg, 0.78 mmol, 16%) as a colorless gum. Data for compound (1-12): ¹H NMR (400 MHz, Chloroform-d) δ 8.27 (d, J=6.7 Hz, 1H), 7.32 (d, J=8.6 Hz, 1H), 4.87 (s, 2H), 4.75 (s, 1H), 1.29 (s, 9H). Data for compound (1-14): ¹H NMR (400 MHz, Chloroform-d) δ 8.18 (d, J=6.7 Hz, 1H), 7.90 (d, J=9.0 Hz, 1H), 7.53 (d, J=1.6 Hz, 1H), 4.60 (s, 1H), 1.27 (s, 9H).

Step 1-6: Synthesis of 6-bromo-2-(tert-butyl)-5-fluoro-2,3-dihydrobenzo[d]isothiazole 1,1-dioxide

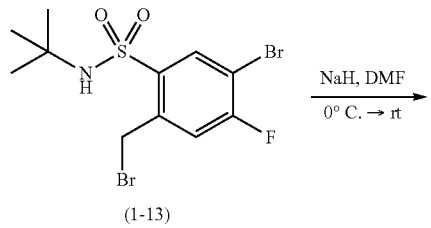

Sodium hydride (103 mg of a 60% dispersion in mineral oil, 2.6 mmol, 1.3 eq) was added to a solution of compound (1-13) (800 mg, 2.0 mmol, 1.0 eq) in DMF (7.4 mL) at 0° C. The reaction was stirred overnight, gradually warming to room temperature. The reaction was quenched with brine and diluted with EtOAc. The layers were separated and the organic layer was washed with brine (2×). The organic layer was dried (MgSO$_4$), filtered, and concentrated under reduced pressure. The resultant white solid was purified by column chromatography eluting with hexanes/EtOAc (0% EtOAc→25% EtOAc) to afford pure compound (1-15) (414 mg, 1.3 mmol, 65%) as a colorless solid: $^1$H NMR (400 MHz, Chloroform-d) δ 7.95 (d, J=6.0 Hz, 1H), 7.13 (d, J=7.6 Hz, 1H), 4.39 (s, 2H), 1.55 (s, 9H); LCMS (ESI) m/z 322.0 (M+1).

Step 1-7: Synthesis of ethyl 2-(tert-butyl)-5-fluoro-2,3-dihydrobenzo[d]isothiazole-6-carboxylate 1,1-dioxide

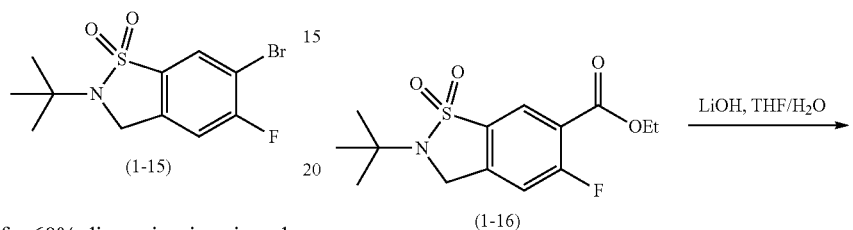

General Procedure for Carbonylation:

A mixture of compound (1-15) (100 mg, 0.31 mmol, 1.0 eq), Pd(OAc)$_2$ (7.0 mg, 0.031 mmol, 0.10 eq), 1,3-bis(diphenylphosphino)propane (26 mg, 0.062 mmol, 0.20 eq), and Et$_3$N (0.13 mL, 0.93 mmol, 3.0 eq) in DMF (0.83 mL) and EtOH (0.41 mL) were stirred under a balloon of CO$_{(g)}$ at 80° C. overnight. The reaction was quenched with H$_2$O and brine, and diluted with EtOAc. The layers were separated and the organic layer was washed with H$_2$O/brine (2×). The organic layer was dried (MgSO$_4$), filtered, and concentrated under reduced pressure. The resultant yellow gum was purified by column chromatography eluting with hexanes/EtOAc (0% EtOAc→30% EtOAc) to afford pure compound (1-16) (55 mg, 0.17 mmol, 56%): $^1$H NMR (400 MHz, Chloroform-d) δ 8.36 (d, J=6.3 Hz, 1H), 7.15 (d, J=9.7 Hz, 1H), 4.47 (s, 2H), 4.42 (q, J=7.1 Hz, 2H), 1.57 (s, 9H), 1.41 (t, J=7.1 Hz, 3H).

Step 1-8: Synthesis of 2-(tert-butyl)-5-fluoro-2,3-dihydrobenzo[d]isothiazole-6-carboxylic Acid 1,1-dioxide

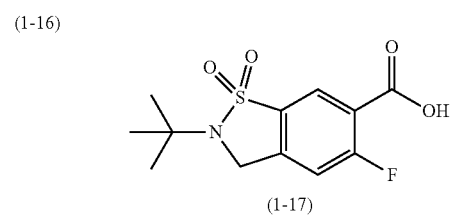

General Procedure for Ester Hydrolysis:

LiOH (0.8 mL of a 1.0 M solution in H$_2$O, 0.8 mmol, 2.0 eq) was added to a solution of compound (1-16) (126 mg, 0.4 mmol, 1.0 eq) in THF (1.1 mL) and the reaction was stirred for 2 hrs. The reaction was made acidic with 1.0 M HCl and diluted with EtOAc. The layers were separated, and the aqueous layer extracted with EtOAc (2×). The combined organic layers were dried (MgSO$_4$), filtered, and concentrated to give pure compound (1-17) (111 mg, 0.39 mmol, 97%) as a colorless solid: $^1$H NMR (400 MHz, DMSO-d$_6$) δ 13.76 (s, 1H), 8.13 (d, J=6.3 Hz, 1H), 7.58 (d, J=10.4 Hz, 1H), 4.61 (s, 2H), 1.46 (s, 9H); LCMS (ESI) m/z 286.1 (M−1).

Step 1-9: Synthesis of 2-(tert-butyl)-5-fluoro-N-(6-(1-isopropyl-1H-tetrazol-5-yl)pyridin-2-yl)-2,3-dihydrobenzo[d]isothiazole-6-carboxamide 1,1-dioxide

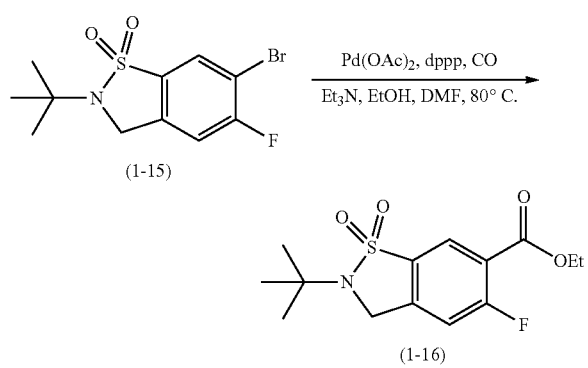

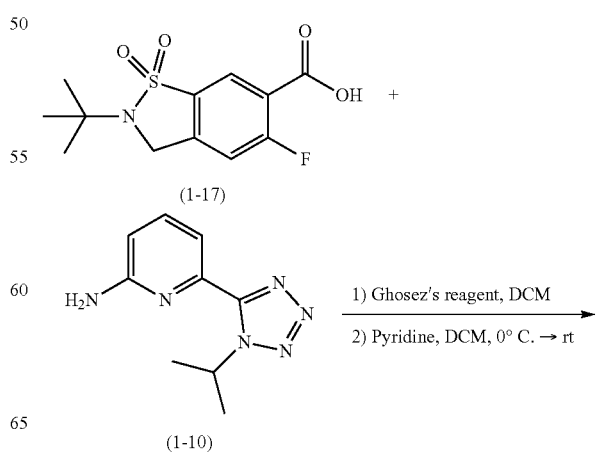

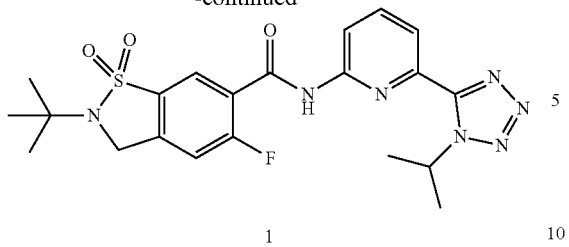

1

General Procedure for Amide Formation with Ghosez's Reagent:

Ghosez's reagent (51 μL, 0.39 mmol, 2.1 eq) was added dropwise to a solution of compound (1-17) (55 mg, 0.19 mmol, 1.1 eq) in DCM (0.41 mL) and the reaction was stirred for 1 hr at room temperature. The reaction was concentrated under reduced pressure and dried under vacuum. The resultant residue was dissolved in DCM (0.41 mL) and cooled to 0° C. Compound (1-10) (37 mg, 0.18 mmol, 1.0 eq) and pyridine (59 μL, 0.73 mmol, 4.0 eq) were added and the reaction was stirred overnight, gradually warming to room temperature. The reaction was concentrated under reduced pressure. The resultant orange gum was purified by column chromatography eluting with hexanes/EtOAc (0% EtOAc→60% EtOAc) to afford pure compound 1 (53 mg, 0.11 mmol, 61%) as a colorless solid: $^1$H NMR (400 MHz, DMSO-$d_6$) δ 11.29 (s, 1H), 8.31 (dd, J=8.4, 0.9 Hz, 1H), 8.19 (d, J=6.0 Hz, 1H), 8.15 (dd, J=8.4, 7.6 Hz, 1H), 8.02 (dd, J=7.6, 0.9 Hz, 1H), 7.64 (d, J=9.6 Hz, 1H), 5.97 (hept, J=6.6 Hz, 1H), 4.63 (s, 2H), 1.55 (d, J=6.6 Hz, 6H), 1.48 (s, 9H); LCMS (ESI) m/z 474.2 (M+1).

Examples 2 and 3: (R)-2-(tert-butyl)-5-fluoro-N-(6-(1-(1-hydroxypropan-2-yl)-1H-tetrazol-5-yl)pyridin-2-yl)-2,3-dihydrobenzo[d]isothiazole-6-carboxamide 1,1-dioxide and (R)-2-(tert-butyl)-N-(6-(1-(1-hydroxypropan-2-yl)-1H-tetrazol-5-yl)pyridin-2-yl)-5-methoxy-2,3-dihydrobenzo[d]isothiazole-6-carboxamide 1,1-dioxide

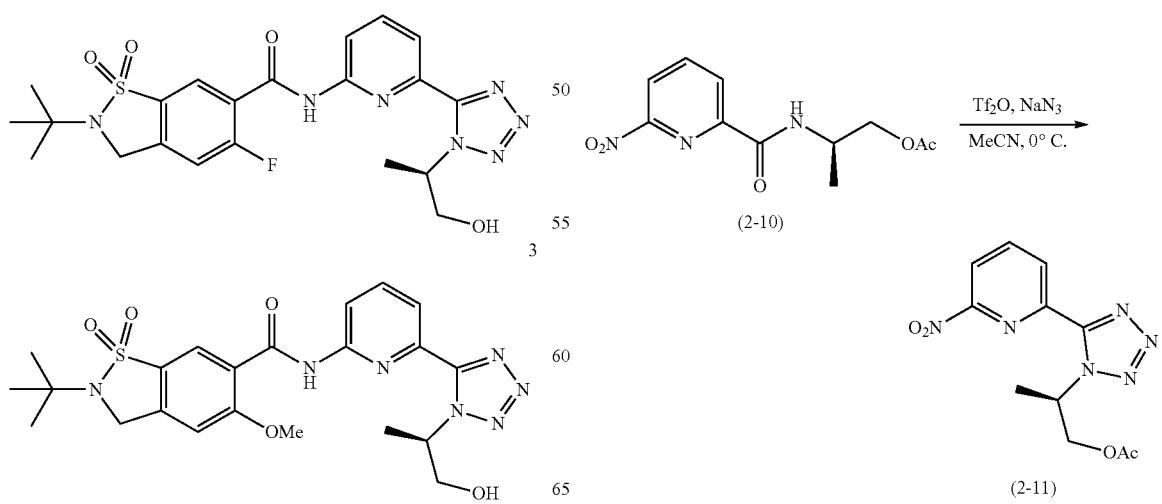

Step 2-1: Synthesis of (R)-2-(6-nitropicolinamido)propyl acetate

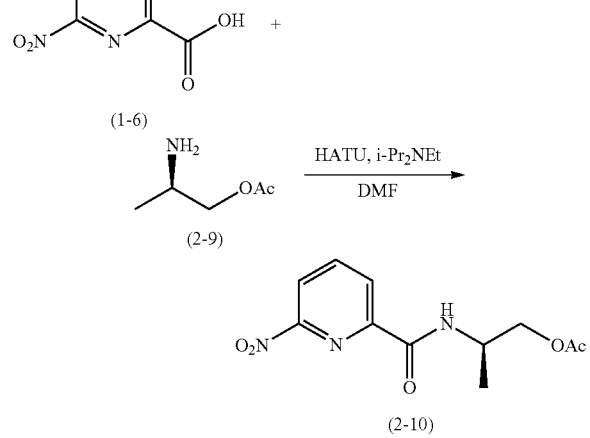

Hunig's base (3.1 mL, 5.3 mmol, 1.5 eq), a solution of amine (2-9) (1.1 g, 4.6 mmol, 1.3 eq) in DMF (5.0 mL), and HATU (2.0 g, 5.3 mmol, 1.5 eq) was added to a solution of 6-nitropicolinic acid (1-6) (592 mg, 3.5 mmol, 1.0 eq) in DMF (6.7 mL) and the reaction was stirred overnight. The reaction was quenched with H$_2$O and diluted with EtOAc. The layers were separated and the aqueous layer was extracted with EtOAc (2×). The combined organic layers were washed with water, brine (2×), dried (MgSO$_4$), filtered, and concentrated under reduced pressure. The resultant yellow gum was purified by column chromatography eluting with hexanes/EtOAc (0% EtOAc→40% EtOAc) to afford pure compound (2-10) (770 mg, 2.9 mmol, 82%) as a yellow gum: $^1$H NMR (400 MHz, Chloroform-d) δ 8.57 (dd, J=7.7, 1.0 Hz, 1H), 8.39 (dd, J=8.1, 1.0 Hz, 1H), 8.23 (t, J=7.9 Hz, 1H), 7.92 (d, J=8.6 Hz, 1H), 4.57-4.43 (m, 1H), 4.27-4.15 (m, 2H), 2.11 (s, 3H), 1.36 (d, J=6.8 Hz, 3H).

Step 2-2: Synthesis of (R)-2-(5-(6-nitropyridin-2-yl)-1H-tetrazol-1-yl)propyl acetate Tf₂O (4.3 mL of a 1.0 M solution in DCM, 4.3 mmol, 1.5 eq) was added dropwise to a mixture of compound (2-10) (765 mg, 2.9 mmol, 1.0 eq) and NaN₃ (298 mg, 4.6 mmol, 1.6 eq) in CH₃CN (19.0 mL) at 0° C. The reaction was stirred for 30 min at 0° C., then at room temperature for 1 h. The reaction was quenched with sat. NaHCO₃ and diluted with EtOAc. The layers were separated, and the organic layer was washed with brine, dried (MgSO₄), filtered, and concentrated under reduced pressure. The resulting yellow gum was purified by column chromatography eluting with hexanes/EtOAc (0% EtOAc→60% EtOAc) to afford pure compound (2-11) (699 mg, 2.4 mmol, 84%) as a pale yellow solid: ¹H NMR (500 MHz, Chloroform-d) δ 8.79 (dd, J=7.8, 0.9 Hz, 1H), 8.43 (dd, J=8.1, 1.0 Hz, 1H), 8.32 (t, J=7.9 Hz, 1H), 6.20-6.13 (m, 1H), 4.64 (dd, J=11.8, 4.6 Hz, 1H), 4.59 (dd, J=11.7, 7.5 Hz, 1H), 1.88 (d, J=1.0 Hz, 3H), 1.82 (dd, J=6.9, 1.1 Hz, 3H).

Step 2-3: Synthesis of (R)-2-(5-(6-aminopyridin-2-yl)-1H-tetrazol-1-yl)propyl acetate

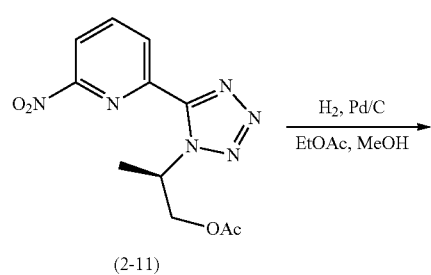

Pd/C (140 mg of a 10% weight % mixture) was added to a solution of compound (2-11) (699 mg, 2.4 mmol, 1.0 eq) in MeOH (18.4 mL) and EtOAc (18.4 mL). The reaction was evacuated and backfilled with an H₂ balloon (3×) and stirred under an atmosphere of H₂ overnight. The reaction was filtered through CELITE® and concentrated under reduced pressure. The residue was taken up in DCM and filtered through CELITE®, rinsing with DCM. The filtrated was concentrated under reduced pressure to afford pure compound (2-12) (575 mg, 2.2 mmol, 92%) as a colorless solid: ¹H NMR (500 MHz, Chloroform-d) δ 7.68-7.57 (m, 2H), 6.66 (d, J=8.4 Hz, 1H), 6.27-6.18 (m, 1H), 4.67 (dd, J=11.4, 4.3 Hz, 1H), 4.30 (dd, J=11.4, 9.4 Hz, 1H), 1.84 (s, 3H), 1.70 (d, J=6.9 Hz, 3H).

Step 2-4: Synthesis of (R)-2-(5-(6-(2-(tert-butyl)-5-fluoro-1,1-dioxido-2,3-dihydrobenzo[d]isothiazole-6-carboxamido)pyridin-2-yl)-1H-tetrazol-1-yl)propyl acetate Compound (2-13) was prepared from compounds (1-17) and (2-12) according to the general procedure for amide formation with Ghosez's reagent and purified by column chromatography eluting with hexanes/EtOAc (0% EtOAc→60% EtOAc) to afford pure compound (2-16) (84 mg, 0.16 mmol, 87%) as a colorless amorphous solid: ¹H NMR (400 MHz, DMSO-d₆) δ 11.24 (s, 1H), 8.30 (dd, J=8.3, 0.9 Hz, 1H), 8.20 (d, J=6.0 Hz, 1H), 8.19-8.14 (m, 1H), 8.04 (dd, J=7.6, 0.9 Hz, 1H), 7.65 (d, J=9.6 Hz, 1H), 6.29-6.17 (m, 1H), 4.63 (s, 2H), 4.48 (dd, J=11.8, 3.8 Hz, 1H), 4.31 (dd, J=11.8, 8.0 Hz, 1H), 1.73 (s, 3H), 1.64 (d, J=6.9 Hz, 3H), 1.48 (s, 9H); LCMS (ESI) m/z 532.2 (M+1).

Step 2-5: Synthesis of (R)-2-(tert-butyl)-5-fluoro-N-(6-(1-(1-hydroxypropan-2-yl)-1H-tetrazol-5-yl)pyridin-2-yl)-2,3-dihydrobenzo[d]isothiazole-6-carboxamide 1,1-dioxide and (R)-2-(tert-butyl)-N-(6-(1-(1-hydroxypropan-2-yl)-1H-tetrazol-5-yl)pyridin-2-yl)-5-methoxy-2,3-dihydrobenzo[d]isothiazole-6-carboxamide 1,1-dioxide -continued

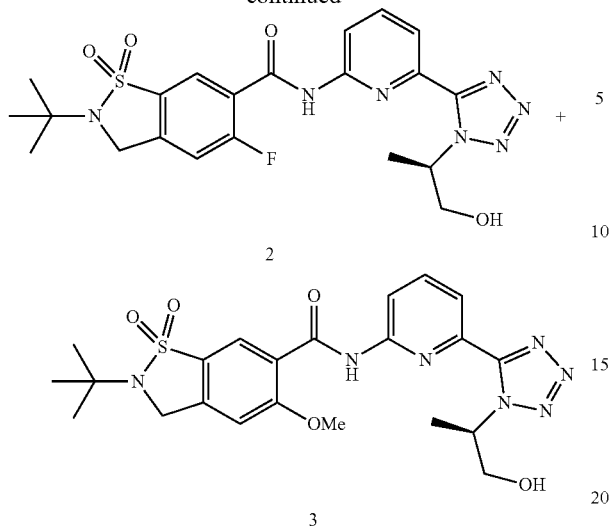

Potassium carbonate (59 mg, 0.42 mmol, 5.0 eq) was added to a solution of compound (2-13) (45 mg, 0.085 mmol, 1.0 eq) in MeOH (0.34 mL) and the reaction was stirred for 0.5 hr. The reaction was quenched with H$_2$O and diluted with DCM. The layers were separated and the aqueous layer was extracted with DCM (2×). The combined organic layers were dried (MgSO$_4$), filtered, and concentrated under reduced pressure. The resultant colorless gum was purified by column chromatography eluting with hexanes/EtOAc (5% EtOAc→100% EtOAc) to afford pure compound 2 (12.3 mg, 0.025 mmol, 30%) as a colorless amorphous solid and pure compound 3 (11.0 mg, 0.022 mmol, 26%) as a colorless amorphous solid. Data for compound 2: $^1$H NMR (400 MHz, DMSO-d$_6$) δ 11.30 (s, 1H), 8.31 (dd, J=8.4, 0.9 Hz, 1H), 8.19 (d, J=6.0 Hz, 1H), 8.14 (dd, J=8.4, 7.6 Hz, 1H), 7.98 (dd, J=7.6, 0.9 Hz, 1H), 7.64 (d, J=9.6 Hz, 1H), 5.92-5.81 (m, 1H), 4.91 (t, J=5.5 Hz, 1H), 4.63 (s, 2H), 3.80-3.68 (m, 2H), 1.54 (d, J=6.8 Hz, 3H), 1.48 (s, 9H); LCMS (ESI) m/z 490.17 (M+1). Data for compound 2: $^1$H NMR (400 MHz, DMSO-d$_6$) δ 10.90 (s, 1H), 8.37 (d, J=8.3 Hz, 1H), 8.13 (t, J=8.0 Hz, 1H), 8.02 (s, 1H), 7.97 (dd, J=7.6, 0.9 Hz, 1H), 7.39 (s, 1H), 5.93-5.79 (m, 1H), 4.95 (t, J=5.6 Hz, 1H), 4.58 (s, 2H), 3.99 (s, 3H), 3.86-3.69 (m, 2H), 1.56 (d, J=6.8 Hz, 3H), 1.48 (s, 9H); LCMS (ESI) m/z 502.2 (M+1).

Example 4: 2-(tert-butyl)-6-fluoro-N-(6-(1-isopropyl-1H-tetrazol-5-yl)pyridin-2-yl)-3,4-dihydro-2H-benzo[e][1,2]thiazine-7-carboxamide 1,1-dioxide

4

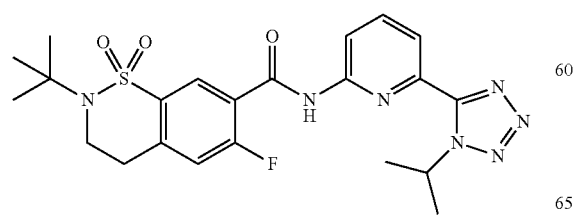

Step 4-1: Synthesis of 5-bromo-N-(tert-butyl)-4-fluoro-2-formylbenzenesulfonamide

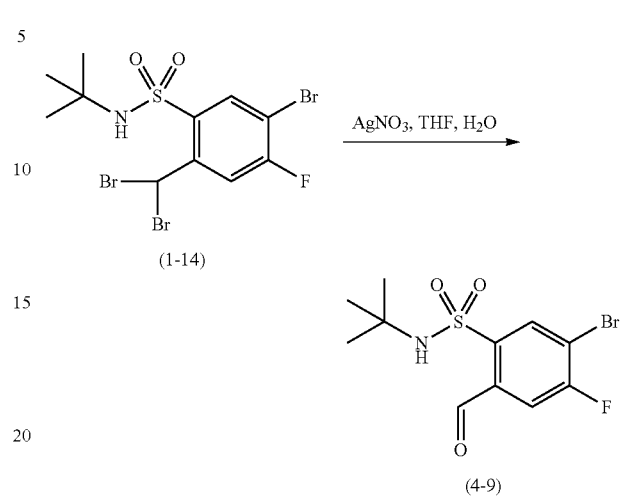

Silver nitrate (377 mg, 2.22 mmol, 3.0 eq) was added to a suspension of compound (1-14) (357 mg, 0.74 mmol, 1.0 eq) in a mixture of THF (2.8 mL) and H$_2$O (0.9 mL) and the reaction was heated at 80° C. overnight. The reaction was quenched with H$_2$O and diluted with EtOAc. The layers were separated and the aqueous layer was extracted with EtOAc (2×). The combined organic layers were dried (MgSO$_4$), filtered, and concentrated under reduced pressure. The resultant yellow solid was purified by column chromatography eluting with hexanes/EtOAc (0% EtOAc→25% EtOAc) to afford compound (4-9) as a white solid: $^1$H NMR (400 MHz, Chloroform-d) δ 10.42 (d, J=1.6 Hz, 1H), 8.37 (d, J=6.2 Hz, 1H), 7.70 (d, J=8.0 Hz, 1H), 5.20 (s, 1H), 1.26 (s, 9H); LCMS (ESI) m/z 336.0 (M−1).

Step 4-2: Synthesis of (Z)-5-bromo-N-(tert-butyl)-4-fluoro-2-(2-methoxyvinyl)benzenesulfonamide and (E)-5-bromo-N-(tert-butyl)-4-fluoro-2-(2-methoxyvinyl)benzenesulfonamide

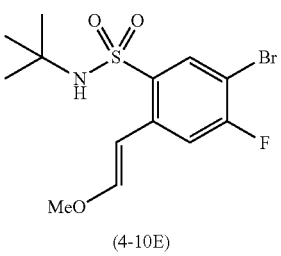

(4-10E)

NaHMDS (0.28 mL of a 1.0 M solution in THF, 0.28 mmol, 1.1 eq) was added dropwise to a suspension of (methoxymethyl)triphenylphosphonium chloride (95 mg, 0.28 mmol, 1.1 eq) in THF (0.13 mL) at 0° C. and the reaction was stirred for 30 min at 0° C. The reaction was cooled to −78° C. and a solution of compound (4-9) (85 mg, 0.25 mmol, 1.0 eq) in THF (0.13 mL) was added dropwise. The cold bath was removed, and the reaction stirred at room temperature overnight. The reaction was quenched with H$_2$O and diluted with DCM. The layers were separated and the aqueous layer was extracted with DCM (2×). The combined organic layers were dried (MgSO$_4$), filtered, and concentrated under reduced pressure. The resultant yellow oil was purified by column chromatography eluting with hexanes/EtOAc (0% EtOAc→30% EtOAc) to afford pure compound (4-10Z) (10.4 mg, 0.028 mmol, 11%) as a white solid and pure compound (4-10E) (45 mg, 0.12 mmol, 49%) as a white solid. Data for compound (4-10Z): $^1$H NMR (400 MHz, Chloroform-d) δ 8.22 (d, J=7.1 Hz, 1H), 7.85 (d, J=10.4 Hz, 1H), 6.39 (d, J=7.2 Hz, 1H), 5.89 (dd, J=7.2, 1.2 Hz, 1H), 4.51 (s, 1H), 3.84 (s, 3H), 1.18 (s, 9H). Data for compound (4-10E): $^1$H NMR (400 MHz, Chloroform-d) δ 8.23 (d, J=7.1 Hz, 1H), 7.13 (d, J=9.5 Hz, 1H), 7.00 (d, J=12.8 Hz, 1H), 6.43 (dd, J=12.8, 1.0 Hz, 1H), 4.41 (s, 1H), 3.75 (s, 3H), 1.18 (s, 9H).

Step 4-3: Synthesis of 7-bromo-2-(tert-butyl)-6-fluoro-2H-benzo[e][1,2]thiazine 1,1-dioxide

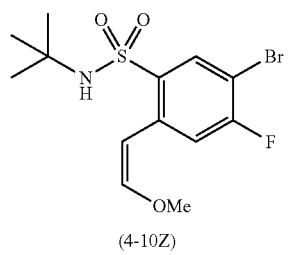

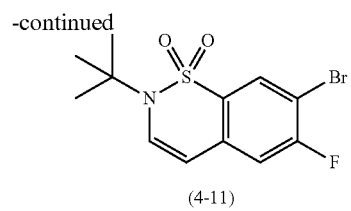

(4-11)

Hydrochloric acid (0.15 mL of a 6.0 M solution in H$_2$O) was added to a suspension of (4-10Z) (10.4 mg, 0.028 mmol) and (4-10E) (45 mg, 0.12 mmol) in THF (0.23 mL) and the reaction was stirred at 50° C. for 1 h. The reaction was quenched with H$_2$O and diluted with DCM. The layers were separated and the aqueous layer was extracted with DCM (2×). The combined organic layers were dried (MgSO$_4$), filtered, and concentrated under reduced pressure to afford pure compound (4-11) (47 mg, 0.14 mmol, 93%) as a colorless solid: $^1$H NMR (400 MHz, Chloroform-d) δ 8.09 (dd, J=6.5, 0.6 Hz, 1H), 7.08 (d, J=8.8 Hz, 1H), 6.89 (dd, J=8.3, 0.6 Hz, 1H), 6.21 (d, J=8.2 Hz, 1H), 1.63 (s, 9H).

Step 4-4: Synthesis of 7-bromo-2-(tert-butyl)-6-fluoro-3,4-dihydro-2H-benzo[e][1,2]thiazine 1,1-dioxide and 5-bromo-N-(tert-butyl)-2-ethyl-4-fluorobenzenesulfonamide

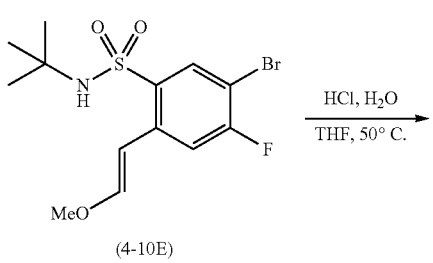

Pt$_2$O (32 mg, 0.14 mmol, 1.0 eq) was added to a solution of compound (4-11) (47 mg, 0.14 mmol, 1.0 eq) in EtOAc (1.4 mL). The reaction was evacuated and backfilled with an H$_2$ balloon (3×) and stirred under an atmosphere of H$_2$ for 6 days. The reaction was filtered and concentrated under reduced pressure. The resultant yellow gum was purified by column chromatography eluting with hexanes/EtOAc (0% EtOAc→30% EtOAc) to afford pure compound (4-12) (17.1 mg, 0.051 mmol, 36%) as a colorless solid and pure compound (4-13) (11.7 mg, 0.035 mmol, 25%) as a colorless solid. Data for compound (4-12): $^1$H NMR (400 MHz, Chloroform-d) δ 8.05 (d, J=6.7 Hz, 1H), 6.96 (d, J=8.7 Hz, 1H), 3.99 (t, J=6.3 Hz, 2H), 2.91 (t, J=6.2 Hz, 2H), 1.46 (s, 9H). Data for compound (4-13): $^1$H NMR (400 MHz, Chloroform-d) δ 8.25 (d, J=7.0 Hz, 1H), 7.12 (d, J=9.4 Hz, 1H), 4.38 (s, 1H), 3.01 (q, J=7.5 Hz, 2H), 1.31 (t, J=7.5 Hz, 3H), 1.25 (s, 9H).

Step 4-5: Synthesis of ethyl 2-(tert-butyl)-6-fluoro-3,4-dihydro-2H-benzo[e][1,2]thiazine-7-carboxylate 1,1-dioxide

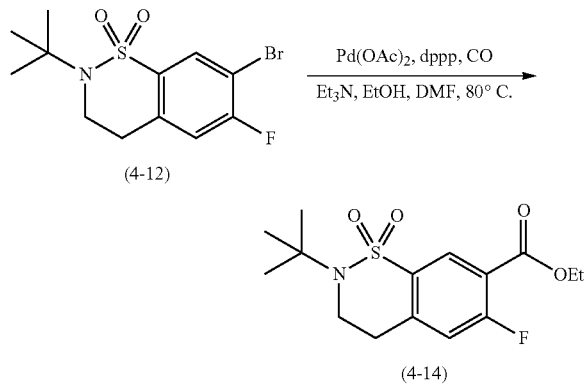

Compound (4-14) was prepared from compound (4-12) according to the general procedure for carbonylation and purified by column chromatography eluting with hexanes/EtOAc (0% EtOAc→30% EtOAc) to afford pure compound (4-14) (5.9 mg, 0.018 mmol, 35%) as a colorless solid: $^1$H NMR (400 MHz, Chloroform-d) δ 8.44 (d, J=7.0 Hz, 1H), 6.99 (d, J=10.7 Hz, 1H), 4.39 (q, J=7.1 Hz, 2H), 4.00 (t, J=6.2 Hz, 2H), 2.99 (t, J=6.2 Hz, 2H), 1.46 (s, 9H), 1.40 (t, J=7.1 Hz, 3H).

Step 4-6: Synthesis of 2-(tert-butyl)-6-fluoro-3,4-dihydro-2H-benzo[e][1,2]thiazine-7-carboxylic acid 1,1-dioxide

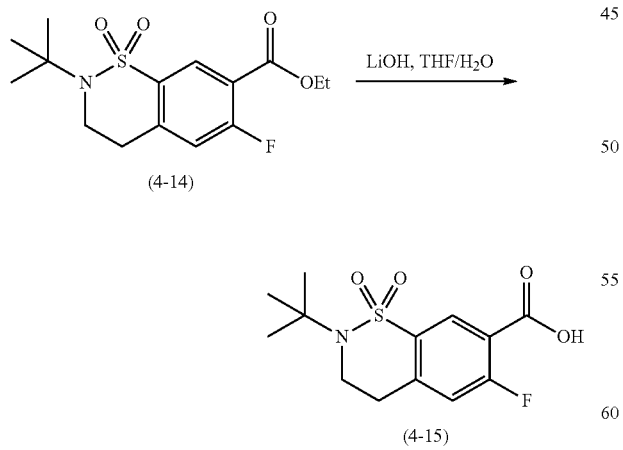

Compound (4-15) was prepared from compound (4-14) according to the general procedure for ester hydrolysis to afford compound (4-15) (5.4 mg, 0.39 mmol, 100%) which was used directly without purification.

Step 4-7: Synthesis of 2-(tert-butyl)-6-fluoro-N-(6-(1-isopropyl-1H-tetrazol-5-yl)pyridin-2-yl)-3,4-dihydro-2H-benzo[e][1,2]thiazine-7-carboxamide 1,1-dioxide

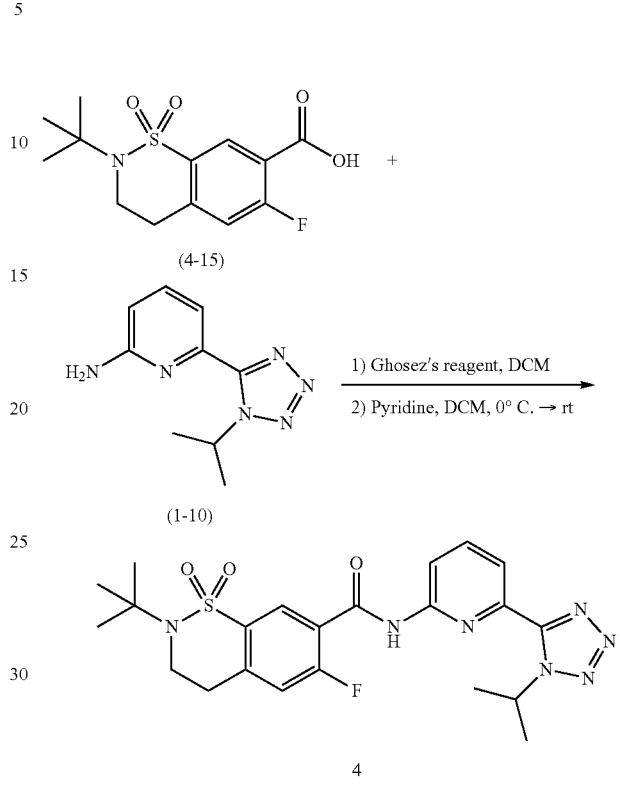

Example 4 was prepared from compounds (4-15) and (1-10) according to the general procedure for amide formation with Ghosez's reagent and purified by column chromatography eluting with hexanes/EtOAc (0% EtOAc→60% EtOAc) to afford pure compound 4 (4.1 mg, 0.008 mmol, 49%) as a colorless amorphous solid: $^1$H NMR (400 MHz, DMSO-$d_6$) δ 11.19 (s, 1H), 8.29 (dd, J=8.4, 0.9 Hz, 1H), 8.15 (t, J=8.0 Hz, 1H), 8.07-7.99 (comp, 2H), 7.46 (d, J=10.7 Hz, 1H), 5.98 (p, J=6.6 Hz, 1H), 3.96 (t, J=6.2 Hz, 2H), 3.07 (t, J=6.2 Hz, 2H), 1.55 (d, J=6.6 Hz, 6H), 1.39 (s, 9H); LCMS (ESI) m/z 488.2 (M+1).

Example 5: 2-(tert-butyl)-N-(6-(1-isopropyl-1H-tetrazol-5-yl)pyridin-2-yl)-6-methoxy-3,4-dihydro-2H-benzo[e][1,2]thiazine-7-carboxamide 1,1-dioxide

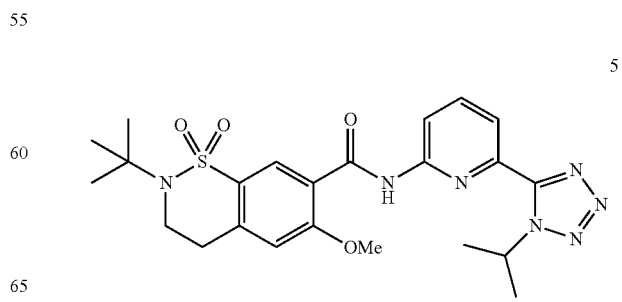

Step 5-1: Synthesis of 2-(tert-butyl)-N-(6-(1-isopropyl-1H-tetrazol-5-yl)pyridin-2-yl)-6-methoxy-3,4-dihydro-2H-benzo[e][1,2]thiazine-7-carboxamide 1,1-dioxide

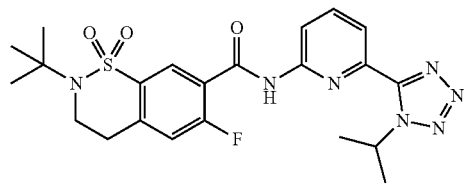 [SMILES: CC(C)n1nnnc1-c1cccc(NC(=O)c2cc3c(cc2F)CCN(C(C)(C)C)S3(=O)=O)n1]

4

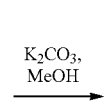

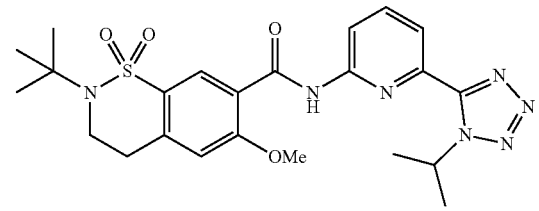 [SMILES: COc1cc2c(cc1C(=O)Nc1cccc(-c3nnnn3C(C)C)n1)S(=O)(=O)N(C(C)(C)C)CC2]

5

General Procedure for Fluoride Displacement:

K$_2$CO$_3$ (4.25 mg, 0.031 mmol) was added to a solution of Example 4 (1.5 mg, 3.08 μmol) in MeOH (0.2 mL) and the reaction was stirred over the weekend. The reaction was quenched with H$_2$O and diluted with CH$_2$Cl$_2$. The layers were separated and the aqueous was layer extracted with CH$_2$Cl$_2$ (2×). The combined organic layers were dried (MgSO$_4$), filtered, and concentrated under reduced pressure to afford pure compound 5 (1.3 mg, 2.60 μmol, 85% yield) as a colorless solid: $^1$H NMR (500 MHz, Chloroform-d) δ 10.19 (s, 1H), 8.80 (s, 1H), 8.57 (dd, J=8.2, 1.0 Hz, 1H), 8.03 (dd, J=7.6, 1.1 Hz, 1H), 7.97 (t, J=7.9 Hz, 1H), 6.85 (s, 1H), 5.72 (hept, J=6.7 Hz, 1H), 4.10 (s, 3H), 4.02 (t, J=6.2 Hz, 2H), 3.03 (t, J=6.2 Hz, 2H), 1.74 (d, J=6.7 Hz, 6H), 1.48 (s, 9H); LCMS (ESI) m/z 500.2 (M+1).

Example 6: 2-(tert-butyl)-N-(6-(1-isopropyl-1H-tetrazol-5-yl)pyridin-2-yl)-5-methoxy-2,3-dihydrobenzo[d]isothiazole-6-carboxamide 1,1-dioxide

6

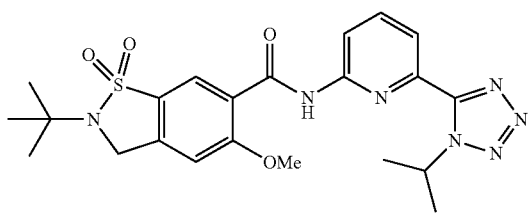

Step 6-1: Synthesis of 2-(tert-butyl)-N-(6-(1-isopropyl-1H-tetrazol-5-yl)pyridin-2-yl)-5-methoxy-2,3-dihydrobenzo[d]isothiazole-6-carboxamide 1,1-dioxide

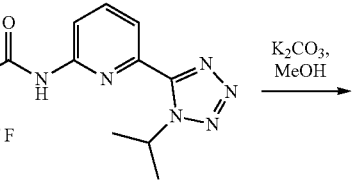

1

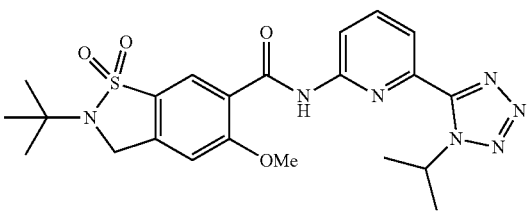 [SMILES: COc1cc2c(cc1C(=O)Nc1cccc(-c3nnnn3C(C)C)n1)S(=O)(=O)N(C(C)(C)C)C2]

6

Example 6 was prepared according to the general procedure for fluoride displacement to afford pure compound 6 (18.8 mg, 0.039 mmol, 76% yield) as a colorless solid: $^1$H NMR (400 MHz, DMSO-d$_6$) δ 10.90 (s, 1H), 8.37 (d, J=8.4 Hz, 1H), 8.14 (t, J=8.0 Hz, 1H), 8.02 (s, 1H), 7.99 (dd, J=7.6, 0.9 Hz, 1H), 7.39 (s, 1H), 5.98-5.90 (m, 1H), 4.58 (s, 2H), 3.98 (s, 3H), 1.58 (d, J=6.6 Hz, 6H), 1.48 (s, 9H); LCMS (ESI) m/z 486.2 (M+1).

Example 7: 5-fluoro-2-isopropyl-N-(6-(4-isopropyl-4H-1,2,4-triazol-3-yl)pyridin-2-yl)-2,3-dihydrobenzo[d]isothiazole-6-carboxamide 1,1-dioxide

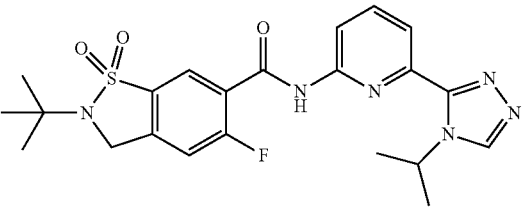

7

Step 7-1: Synthesis of 6-bromo-5-fluorobenzo[d]isothiazol-3(2H)-one 1,1-dioxide

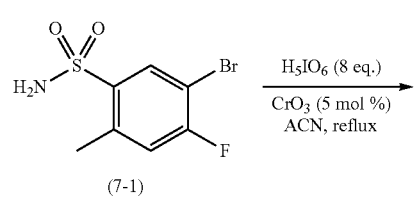

(7-1)

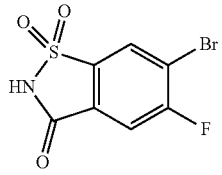

(7-2)

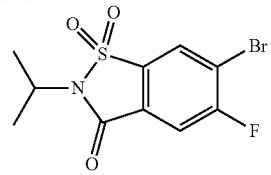

(7-4)

A mixture of periodic acid (34.0 g, 149 mmol), chromium trioxide (93 mg, 0.932 mmol), and 5-bromo-4-fluoro-2-methylbenzenesulfonamide (5.0 g, 18.65 mmol) in $CH_3CN$ (188 mL) was heated at reflux for 1.5 h. The reaction was cooled to rt. 2-propanol (18.8 mL) was added dropwise. The reaction was returned to reflux for 10 min. The reaction was cooled to rt. The reaction was filtered to remove solids, and rinsed with acetone (2×). The filtrate was concentrated and triturated with 2M $H_2SO_4$ and the resultant solid was filtered to give compound (7-1) (4.4 g, 15.71 mmol, 84% yield) as a yellow solid: $^1$H NMR (400 MHz, DMSO-$d_6$) δ 8.64 (d, J=5.7 Hz, 1H), 7.88 (d, J=7.5 Hz, 1H).

Step 7-2: Synthesis of sodium 6-bromo-5-fluoro-3-oxo-3H-benzo[d]isothiazol-2-ide 1,1-dioxide

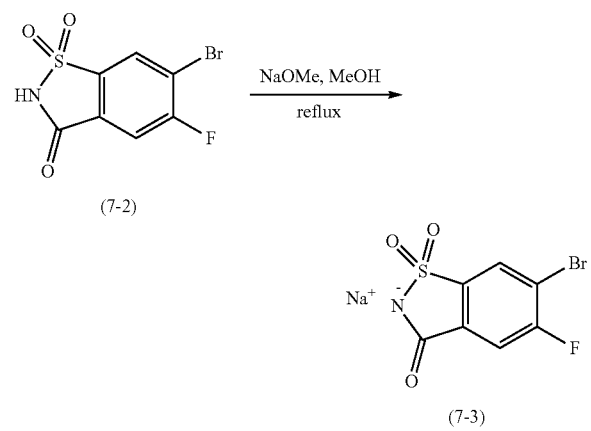

Sodium methoxide (0.752 g, 13.9 mmol) was added to a solution of compound (7-2) (3.9 g, 13.9 mmol) in dry MeOH (82.0 mL) and the reaction was heated at 60° C. for 1 h. The reaction was concentrated to afford compound (7-3) (4.0 g, 13.24 mmol, 95% yield) as a tan solid: $^1$H NMR (400 MHz, DMSO-$d_6$) δ 8.10 (d, J=5.7 Hz, 1H), 7.47 (d, J=7.7 Hz, 1H).

Step 7-3: Synthesis of 6-bromo-5-fluoro-2-isopropylbenzo[d]isothiazol-3(2H)-one 1,1-dioxide

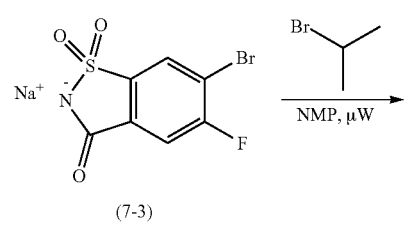

General Procedure for Saccharin Derivative Alkylation:

A mixture of compound (7-3) (1.2 g, 3.97 mmol) and 2-bromopropane (1.87 mL, 19.86 mmol) in NMP (7.95 mL) were heated at 120° C. in the microwave for 2 h. The reaction was quenched with $H_2O$, made acidic with 2M HCl, and diluted with $CH_2Cl_2$. The layers were separated and aqueous layer was extracted with $CH_2Cl_2$ (2×). The combined organic layers were washed with brine/water (2×), dried (MgSO$_4$), filtered, and concentrated under reduced pressure The resultant yellow oil was purified by column chromatography eluting with hexanes/EtOAc (0% EtOAc→15% EtOAc) to afford compound (7-4) (481 mg, 1.493 mmol, 37.6% yield) as a colorless solid: $^1$H NMR (400 MHz, Chloroform-d) δ 8.10 (d, J=5.4 Hz, 1H), 7.71 (d, J=6.7 Hz, 1H), 4.50 (hept, J=6.9 Hz, 1H), 1.61 (d, J=6.9 Hz, 6H).

Step 7-4: Synthesis of 6-bromo-5-fluoro-2-isopropyl-2,3-dihydrobenzo[d]isothiazole 1,1-dioxide

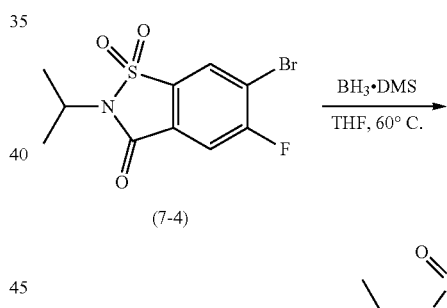

General Procedure for Saccharin Derivative Reduction:

$BH_3$·DMS (0.70 mL, 7.37 mmol) was added to a solution of compound (7-4) (475 mg, 1.47 mmol) in THF (9.22 mL) and the reaction was heated at 60° C. overnight. The reaction was cooled to rt and carefully quenched with 2M HCl and diluted with EtOAc. The layers were separated and the aqueous layer was extracted with EtOAc (2×). The combined organic layers were dried (MgSO$_4$), filtered, and concentrated under reduced pressure. The resultant colorless solid was purified by column chromatography eluting with hexanes/EtOAc (0% EtOAc→30% EtOAc) to afford compound (7-5) (374 mg, 1.214 mmol, 82% yield) as a colorless solid: $^1$H NMR (400 MHz, Chloroform-d) δ 7.99 (d, J=6.0 Hz, 1H), 7.16 (dd, J=7.6, 0.9 Hz, 1H), 4.32 (s, 2H), 4.08 (hept, J=6.7 Hz, 1H), 1.38 (d, J=6.6 Hz, 6H).

Step 7-5: Synthesis of ethyl 5-fluoro-2-isopropyl-2,3-dihydrobenzo[d]isothiazole-6-carboxylate 1,1-dioxide and ethyl 5-ethoxy-2-isopropyl-2,3-dihydrobenzo[d]isothiazole-6-carboxylate 1,1-dioxide

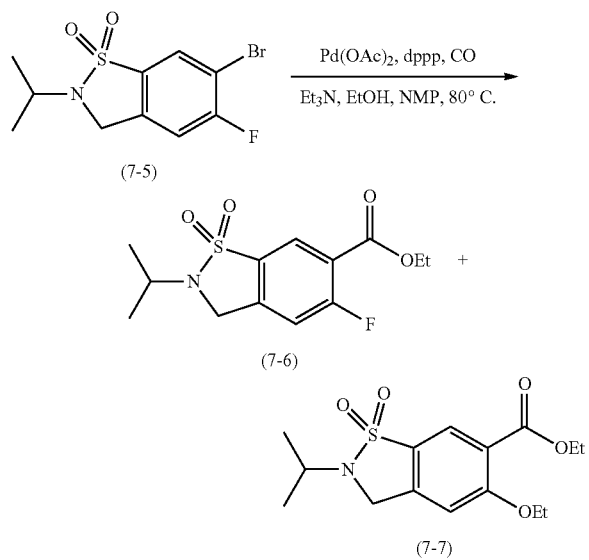

A mixture of compound (7-5) (150 mg, 0.487 mmol), Pd(OAc)$_2$ (10.9 mg, 0.049 mmol), dppp (40.2 mg, 0.097 mmol), and Et$_3$N (0.204 mL, 1.460 mmol) in NMP (1.3 mL)/EtOH (0.65 mL) were stirred under a balloon of CO at 80° C. over the weekend. The reaction was quenched with H$_2$O/brine and diluted with EtOAc. The layers were separated and the organic layer washed with water/brine (2×). The organic layer was dried (MgSO$_4$), filtered, and concentrated under reduced pressure. The resultant brown gum was purified by column chromatography eluting with hexanes/EtOAc (0% EtOAc→25% EtOAc) to afford recovered compound (7-5) (52 mg, 0.169 mmol, 34.7% yield) and an inseparable mixture of compounds (7-6) and (7-7) (81 mg). This material was brought forward as a mixture.

Step 7-6: Synthesis of 5-fluoro-2-isopropyl-2,3-dihydrobenzo[d]isothiazole-6-carboxylic Acid 1,1-dioxide and 5-ethoxy-2-isopropyl-2,3-dihydrobenzo[d]isothiazole-6-carboxylic Acid 1,1-dioxide

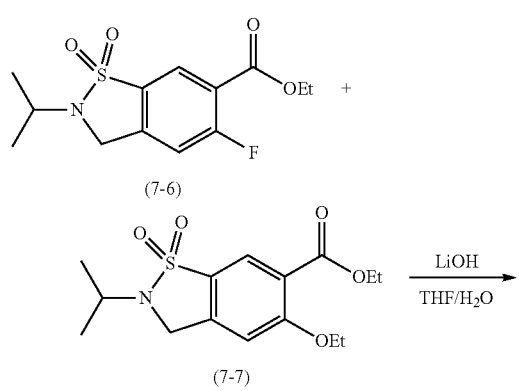

LiOH (0.81 mL, 0.81 mmol of a 1M aqueous solution) was added to a solution of 81 mg of a mixture of compounds (7-6) and (7-7) in THF (0.77 mL) and the reaction was stirred overnight. The reaction was acidified with 1M HCl and concentrated under reduced pressure. The resultant residue was purified by reverse phase HPLC eluting with CH$_3$CN/H$_2$O (35% CH$_3$CN→95% CH$_3$CN over 20 minutes) to afford pure compound (7-8) (15.8 mg, 0.058 mmol) as a white solid: $^1$H NMR (500 MHz, Chloroform-d) δ 8.49 (d, J=6.3 Hz, 1H), 7.24 (d, J=10.2 Hz, 1H), 4.42 (s, 2H), 4.12 (hept, J=6.6 Hz, 1H), 1.40 (d, J=6.7 Hz, 6H); LCMS (ESI) m/z 272.0 (M−1).

Step 7-7: Synthesis of 5-fluoro-2-isopropyl-N-(6-(4-isopropyl-4H-1,2,4-triazol-3-yl)pyridin-2-yl)-2,3-dihydrobenzo[d]isothiazole-6-carboxamide 1,1-dioxide 6-(4-isopropyl-4H-1,2,4-triazol-3-yl)pyridin-2-amine compound (7-9) was prepared according to the method disclosed in WO 2016106384, the entire contents of which are incorporated herein by reference.

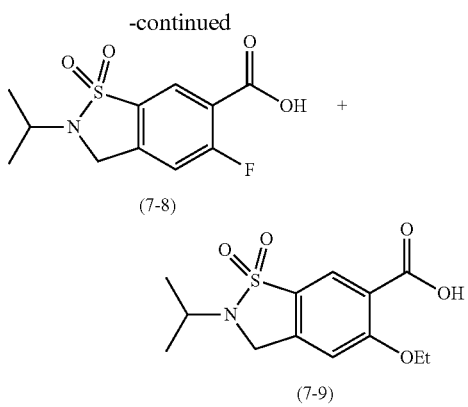

Example 7 was prepared from compounds (7-8) and (7-9) according to the general procedure for amide formation with Ghosez's reagent and purified by column chromatography eluting with CH₂Cl₂/MeOH (0% MeOH→5% MeOH) to afford pure compound 7 (8.5 mg, 0.02 mmol, 67%) as a colorless solid: ¹H NMR (400 MHz, Chloroform-d) δ 8.98 (d, J=13.7 Hz, 1H), 8.63 (d, J=6.7 Hz, 1H), 8.46-8.38 (comp, 2H), 8.08 (d, J=7.6 Hz, 1H), 7.94 (t, J=8.0 Hz, 1H), 7.28 (d, J=11.2 Hz, 1H), 5.49 (hept, J=6.8 Hz, 1H), 4.43 (s, 2H), 4.12 (hept, J=6.6 Hz, 1H), 1.59 (d, J=6.7 Hz, 6H), 1.40 (d, J=6.6 Hz, 6H); LCMS (ESI) m/z 459.2 (M+1).

Example 8: 2-isopropyl-N-(6-(4-isopropyl-4H-1,2,4-triazol-3-yl)pyridin-2-yl)-5-methoxy-2,3-dihydrobenzo[d]isothiazole-6-carboxamide 1,1-dioxide

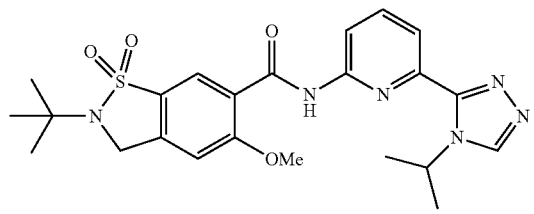

8

Step 8-1: Synthesis of 2-isopropyl-N-(6-(4-isopropyl-4H-1,2,4-triazol-3-yl)pyridin-2-yl)-5-methoxy-2,3-dihydrobenzo[d]isothiazole-6-carboxamide 1,1-dioxide

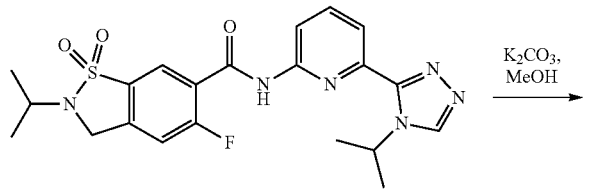

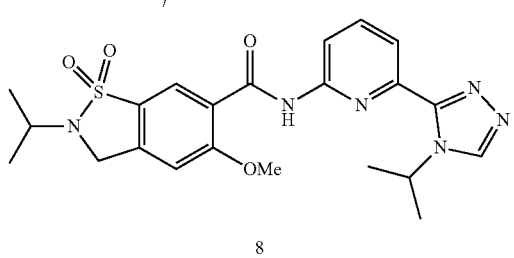

8

Example 8 was prepared from compound 7 according to the general procedure for fluoride displacement to afford pure compound 8 (5.6 mg, 0.012 mmol, 91% yield) as a colorless solid: ¹H NMR (500 MHz, Chloroform-d) δ 10.10 (s, 1H), 8.73 (s, 1H), 8.45 (d, J=8.2 Hz, 1H), 8.37 (s, 1H), 8.01 (d, J=7.5 Hz, 1H), 7.91 (t, J=8.0 Hz, 1H), 7.04 (s, 1H), 5.49 (hept, J=6.7 Hz, 1H), 4.40 (s, 2H), 4.17-4.04 (comp, 4H), 1.62 (d, J=6.8 Hz, 6H), 1.39 (d, J=6.6 Hz, 6H); LCMS (ESI) m/z 471.2 (M+1).

Example 9: (R)-5-fluoro-N-(6-(1-(1-hydroxypropan-2-yl)-1H-tetrazol-5-yl)pyridin-2-yl)-2-isopropyl-2,3-dihydrobenzo[d]isothiazole-6-carboxamide 1,1-dioxide

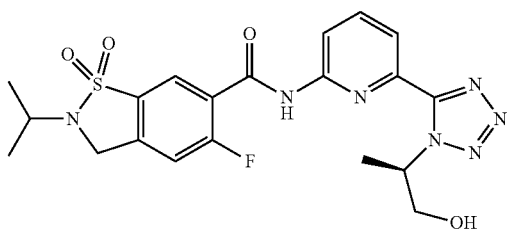 [SMILES: CC(C)N1Cc2cc(F)c(C(=O)Nc3cccc(-c4nnnn4[C@H](C)CO)n3)cc2S1(=O)=O]

9

Step 9-1: Synthesis of (R)-2-(5-(6-aminopyridin-2-yl)-1H-tetrazol-1-yl)propan-1-ol

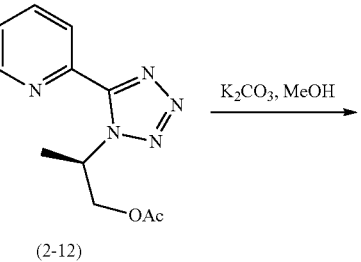

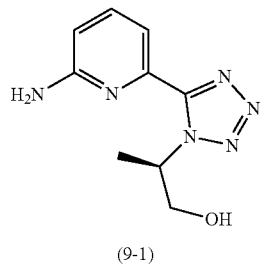

(9-1)

K₂CO₃ (2.63 g, 19.06 mmol) was added to a solution of compound (2-12) (1 g, 3.81 mmol) in MeOH (15.25 mL) and the reaction was stirred at rt for 4.5 hrs. The reaction was concentrated under reduced pressure to remove MeOH. DCM was added, and the reaction concentrated under reduced pressure. The reaction was partitioned between EtOAc and H₂O. Solid NaCl was added to saturate aqueous layer, and the aqueous layer was extracted with EtOAc (3×), or until no UV more compound (9-1) remained in the aqueous layer. The combined organic layers were dried (MgSO₄), filtered, and concentrated under reduced pressure to afford compound (9-1) (840 mg, 3.81 mmol, 100% yield) as a yellow gum: ¹H NMR (400 MHz, DMSO-d₆) δ 7.59 (dd, J=8.4, 7.3 Hz, 1H), 7.27 (dd, J=7.3, 0.8 Hz, 1H), 6.62 (dd, J=8.4, 0.8 Hz, 1H), 6.36 (s, 2H), 5.84-5.71 (m, 1H), 4.96 (t, J=5.6 Hz, 1H), 3.80 (ddd, J=11.1, 8.1, 5.9 Hz, 1H), 3.71 (dt, J=11.0, 5.3 Hz, 1H), 1.52 (d, J=6.8 Hz, 3H).

Step 9-2: Synthesis of (R)-6-(1-(1-((tert-butyldimethylsilyl)oxy)propan-2-yl)-1H-tetrazol-5-yl)pyridin-2-amine

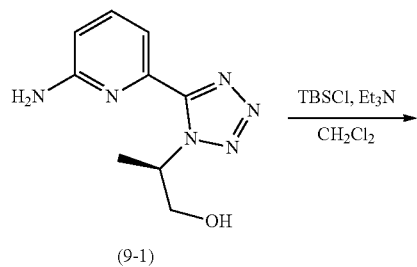

(9-1)

TBSCl, Et₃N
———————→
CH₂Cl₂

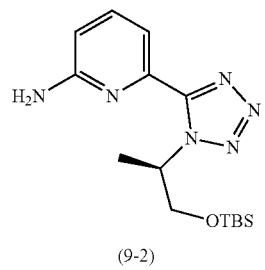

(9-2)

TBSCl (8.6 g, 56.8 mmol) was added to a solution of compound (9-1) (5.0 g, 22.7 mmol) and Et₃N (6.9 g, 9.5 mL, 68.1 mmol) in CH₂Cl₂ (76 mL) at 0° C. The cold bath was removed and the reaction was stirred at rt overnight. The reaction was quenched with sat. NaHCO₃ and diluted with CH₂Cl₂. The layers were separated and the organic layer was washed with H₂O and brine. The organic layer was dried (MgSO₄), filtered, and concentrated under reduced pressure. The resultant brown solid was purified by column chromatography eluting with hexanes/EtOAc (0% EtOAc→40% EtOAc) to afford compound (9-2) (7.12 g, 21.3 mmol, 94% yield) as a brown solid: ¹H NMR (400 MHz, Chloroform-d) δ 7.69-7.57 (comp, 2H), 6.68 (d, J=8.1 Hz, 1H), 5.92-5.74 (m, 1H), 3.99 (dd, J=10.2, 8.3 Hz, 1H), 3.89 (dd, J=10.2, 5.3 Hz, 1H), 1.68 (d, J=6.8 Hz, 3H), 0.71 (s, 9H), −0.09 (s, 3H), −0.13 (s, 3H).

Step 9-3: Synthesis of (R)-5-fluoro-N-(6-(1-(1-hydroxypropan-2-yl)-1H-tetrazol-5-yl)pyridin-2-yl)-2-isopropyl-2,3-dihydrobenzo[d]isothiazole-6-carboxamide 1,1-dioxide

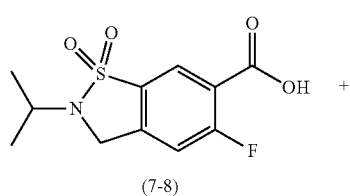

(7-8)

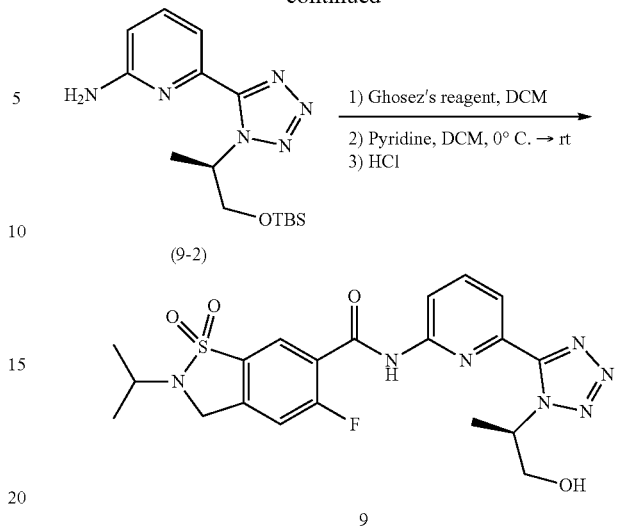

General Procedure for Amide Formation with Ghosez's Reagent Followed by TBS Protection:

Ghosez's Reagent (7.72 μl, 0.058 mmol) was added dropwise to a solution of compound (7-8) (7.9 mg, 0.029 mmol) in DCM (240 μl) and the reaction was stirred for 1 h at rt. The reaction was concentrated under reduced pressure and dried under vacuum. The resultant residue was dissolved in DCM (240 μl) and cooled to 0° C. Compound (9-2) (9.21 mg, 0.028 mmol) and pyridine (8.91 μl, 0.110 mmol) were added, and the reaction stirred overnight, gradually warming to rt. Concentrated HCl (57.4 μl, 0.688 mmol) was added and the reaction was stirred for 6 hrs at rt. The reaction was carefully quenched with sat. NaHCO₃ and diluted with CH₂Cl₂. The layers were separated and the aqueous layer was extracted with CH₂Cl₂ (2×). The combined organic layers were dried (MgSO₄), filtered, and concentrated under reduced pressure. The resultant yellow gum was purified by column chromatography eluting with CH₂Cl₂/MeOH (0% MeOH→5% MeOH) to afford compound 9 (7.8 mg, 0.016 mmol, 59.6% yield) as a colorless residue: ¹H NMR (500 MHz, Chloroform-d) δ 9.14 (d, J=12.9 Hz, 1H), 8.58 (d, J=6.6 Hz, 1H), 8.45 (dd, J=8.4, 0.9 Hz, 1H), 8.09 (dd, J=7.6, 1.1 Hz, 1H), 8.01 (t, J=8.0 Hz, 1H), 7.28 (d, J=10.9 Hz, 1H), 5.77-5.66 (m, 1H), 4.43 (s, 2H), 4.21-4.02 (comp, 3H), 1.67 (d, J=6.9 Hz, 3H), 1.40 (d, J=6.6 Hz, 6H); LCMS (ESI) m/z 476.2 (M+1).

Example 10: (R)—N-(6-(1-(1-hydroxypropan-2-yl)-1H-tetrazol-5-yl)pyridin-2-yl)-2-isopropyl-5-methoxy-2,3-dihydrobenzo[d]isothiazole-6-carboxamide 1,1-dioxide

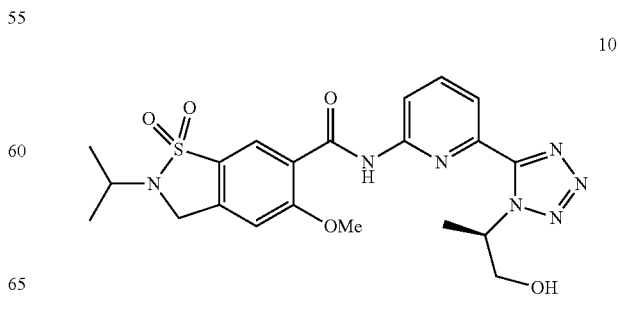

10

Step 10-1: Synthesis of (R)—N-(6-(1-(1-hydroxy-propan-2-yl)-1H-tetrazol-5-yl)pyridin-2-yl)-2-isopropyl-5-methoxy-2,3-dihydrobenzo[d]isothiazole-6-carboxamide 1,1-dioxide

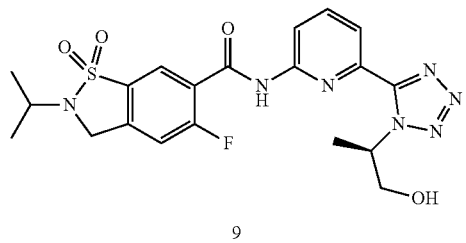

9

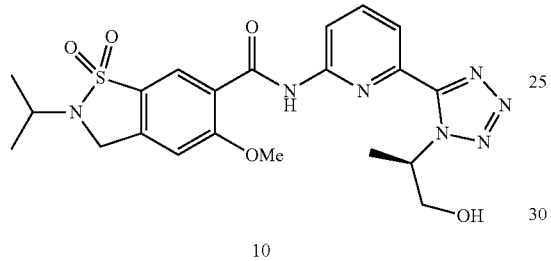

10

Example 10 was prepared from compound 9 according to the general procedure for fluoride displacement to afford pure compound 10 (4.8 mg, 0.010 mmol, 78% yield) as a colorless residue: ¹H NMR (400 MHz, Chloroform-d) δ 10.36 (s, 1H), 8.72 (s, 1H), 8.54 (dd, J=6.5, 2.9 Hz, 1H), 8.03-7.95 (comp, 2H), 7.05 (s, 1H), 5.66-5.54 (m, 1H), 4.40 (s, 2H), 4.19 (s, 3H), 4.15-4.02 (comp, 3H), 1.71 (d, J=6.8 Hz, 3H), 1.39 (d, J=6.6 Hz, 6H); LCMS (ESI) m/z 488.2 (M+1).

Example 11: (R)-5-ethoxy-N-(6-(1-(1-hydroxypropan-2-yl)-1H-tetrazol-5-yl)pyridin-2-yl)-2-isopropyl-2,3-dihydrobenzo[d]isothiazole-6-carboxamide 1,1-dioxide

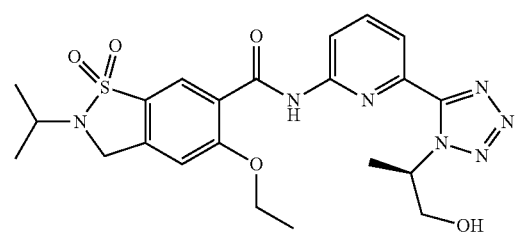 [SMILES: CCOc1cc2c(cc1C(=O)Nc1cccc(-c3nnnn3[C@H](C)CO)n1)S(=O)(=O)N(C(C)C)C2]

11

Step 11-1: Synthesis of (R)-5-ethoxy-N-(6-(1-(1-hydroxypropan-2-yl)-1H-tetrazol-5-yl)pyridin-2-yl)-2-isopropyl-2,3-dihydrobenzo[d]isothiazole-6-carboxamide 1,1-dioxide

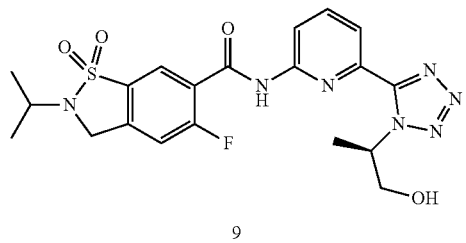

9

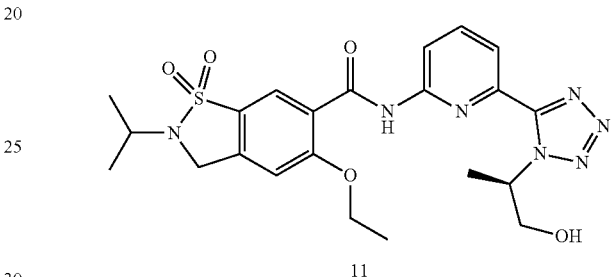

11

Example 11 was prepared from compound 9 according to the general procedure for fluoride displacement, using EtOH as the nucleophile, and using 8.0 equivalents of K₂CO₃ to afford pure compound 11 (19.9 mg, 0.04 mmol, 94% yield) as a yellow solid: ¹H NMR (400 MHz, Chloroform-d) δ 10.30 (s, 1H), 8.76 (s, 1H), 8.50 (dd, J=8.4, 1.0 Hz, 1H), 8.07 (dd, J=7.7, 1.0 Hz, 1H), 7.99 (t, J=8.0 Hz, 1H), 7.03 (s, 1H), 5.81-5.76 (m, 1H), 4.46-4.38 (comp, 4H), 4.14-4.06 (m, 2H), 3.06-3.00 (m, 1H), 1.68-1.64 (comp, 6H), 1.40 (d, J=6.6 Hz, 6H); LCMS (ESI) m/z 502.2 (M+1).

Example 12: (R)—N-(6-(1-(1-hydroxypropan-2-yl)-1H-tetrazol-5-yl)pyridin-2-yl)-2-isopropyl-5-(2,2,2-trifluoroethoxy)-2,3-dihydrobenzo[d]isothiazole-6-carboxamide 1,1-dioxide

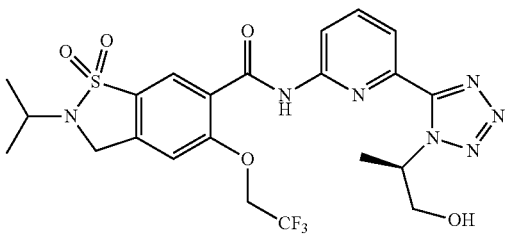

12

Step 12-1: Synthesis of (R)—N-(6-(1-(1-hydroxy-propan-2-yl)-1H-tetrazol-5-yl)pyridin-2-yl)-2-isopropyl-5-(2,2,2-trifluoroethoxy)-2,3-dihydrobenzo[d]isothiazole-6-carboxamide 1,1-dioxide Step 13-1: Synthesis of (R)—N-(6-(1-(1-hydroxy-propan-2-yl)-1H-tetrazol-5-yl)pyridin-2-yl)-5-isopropoxy-2-isopropyl-2,3-dihydrobenzo[d]isothiazole-6-carboxamide 1,1-dioxide

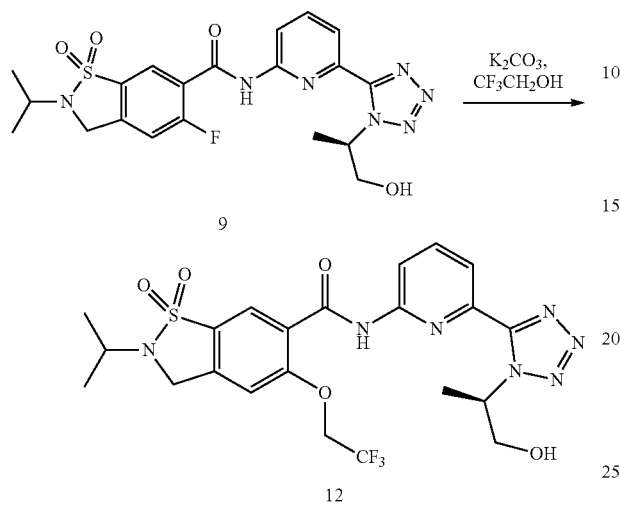

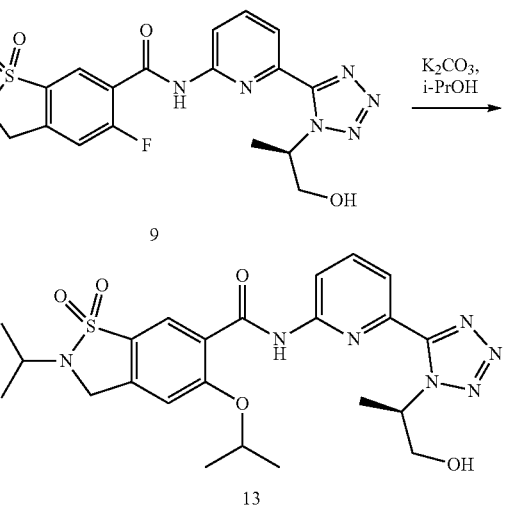

Example 12 was prepared from compound 9 according to the general procedure for fluoride displacement, using CF$_3$CH$_2$OH as the nucleophile, and using 8.0 equivalents of K$_2$CO$_3$, and was purified by column chromatography eluting with CH$_2$Cl$_2$/MeOH (0% MeOH→5% MeOH) to afford pure compound 12 (9.3 mg, 0.017 mmol, 40% yield) as a colorless amorphous solid: $^1$H NMR (400 MHz, Chloroform-d) δ 9.67 (s, 1H), 8.72 (s, 1H), 8.45 (dd, J=8.4, 1.0 Hz, 1H), 8.11 (dd, J=7.7, 1.0 Hz, 1H), 7.99 (t, J=8.0 Hz, 1H), 7.04 (s, 1H), 5.86-5.75 (m, 1H), 4.88-4.68 (m, 2H), 4.42 (s, 2H), 4.20-4.04 (comp, 3H), 3.11 (t, J=6.1 Hz, 1H), 1.64 (d, J=6.9 Hz, 3H), 1.40 (d, J=6.7 Hz, 6H); LCMS (ESI) m/z 556.2 (M+1).

Example 13 was prepared from compound 9 according to the general procedure for fluoride displacement, using i-PrOH as the nucleophile, and using 8.0 equivalents of K$_2$CO$_3$, and was purified by column chromatography eluting with CH$_2$Cl$_2$/MeOH (0% MeOH→5% MeOH) to afford pure compound 13 (4.2 mg, 0.008 mmol, 19% yield) as a colorless amorphous solid: $^1$H NMR (400 MHz, Chloroform-d) δ 10.30 (s, 1H), 8.75 (s, 1H), 8.49 (dd, J=8.3, 1.0 Hz, 1H), 8.08 (dd, J=7.7, 1.0 Hz, 1H), 7.99 (t, J=8.0 Hz, 1H), 7.03 (s, 1H), 5.91-5.77 (m, 1H), 4.91 (p, J=5.9 Hz, 1H), 4.41 (s, 2H), 4.17-4.02 (comp, 3H), 2.77 (dd, J=7.3, 5.1 Hz, 1H), 1.65 (d, J=6.9 Hz, 3H), 1.57 (dd, J=6.1, 2.3 Hz, 6H), 1.40 (d, J=6.6 Hz, 6H); LCMS (ESI) m/z 516.2 (M+1).

Example 13: (R)—N-(6-(1-(1-hydroxypropan-2-yl)-1H-tetrazol-5-yl)pyridin-2-yl)-5-isopropoxy-2-isopropyl-2,3-dihydrobenzo[d]isothiazole-6-carboxamide 1,1-dioxide Example 14: (R)-5-(dimethylamino)-N-(6-(1-(1-hydroxypropan-2-yl)-1H-tetrazol-5-yl)pyridin-2-yl)-2-isopropyl-2,3-dihydrobenzo[d]isothiazole-6-carboxamide 1,1-dioxide

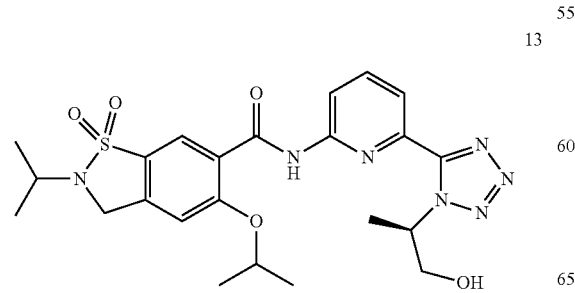

Step 14-1: Synthesis of (R)-5-(dimethylamino)-N-(6-(1-(1-hydroxypropan-2-yl)-1H-tetrazol-5-yl)pyridin-2-yl)-2-isopropyl-2,3-dihydrobenzo[d]isothiazole-6-carboxamide 1,1-dioxide

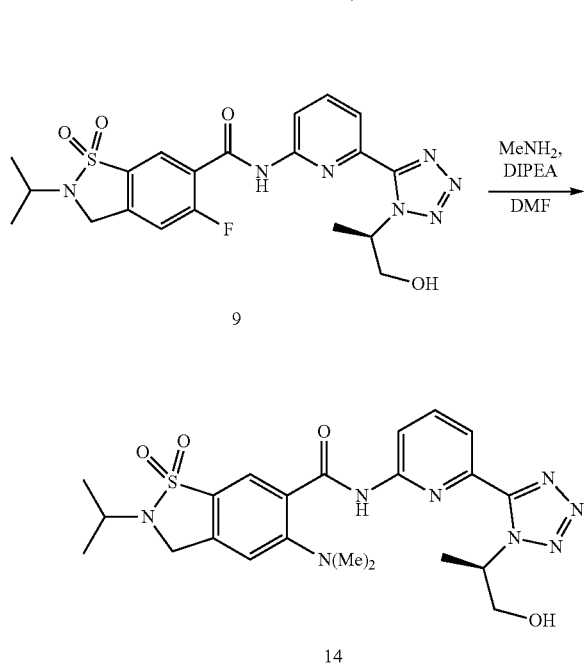

A mixture of compound 9 (20 mg, 0.042 mmol), DIPEA (0.184 mL, 1.052 mmol), and dimethylamine hydrochloride (68.6 mg, 0.841 mmol) in DMF (0.421 mL) were stirred at rt over the weekend. The reaction was quenched with $H_2O$ and diluted with $CH_2Cl_2$. The layers were separated and the aqueous layer was extracted with $CH_2Cl_2$ (2×). The combined organic layers were dried ($MgSO_4$), filtered, and concentrated under reduced pressure. The resultant yellow solid was purified by column chromatography eluting with $CH_2Cl_2$/MeOH (0% MeOH→5% MeOH) to afford compound 14 (16.5 mg, 0.033 mmol, 78% yield) as a yellow amorphous solid: $^1H$ NMR (400 MHz, Chloroform-d) δ 11.79 (s, 1H), 8.62 (s, 1H), 8.56 (dd, J=8.0, 1.4 Hz, 1H), 8.05 (dd, J=7.6, 1.4 Hz, 1H), 8.01 (t, J=7.8 Hz, 1H), 7.27 (s, 1H), 5.66 (dt, J=13.0, 6.8 Hz, 1H), 4.41 (s, 2H), 4.17-4.07 (comp, 3H), 3.57-3.51 (m, 1H), 2.92 (s, 6H), 1.70 (d, J=6.8 Hz, 3H), 1.40 (d, J=6.7 Hz, 6H); LCMS (ESI) m/z 501.2 (M+1).

Example 15: 5-fluoro-N-(6-(4-isopropyl-4H-1,2,4-triazol-3-yl)pyridin-2-yl)-2-methyl-2,3-dihydrobenzo[d]isothiazole-6-carboxamide 1,1-dioxide

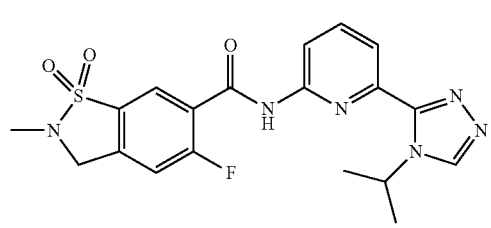

Step 15-1: Synthesis of 6-bromo-5-fluoro-2-methyl-benzo[d]isothiazol-3 (2H)-one 1,1-dioxide

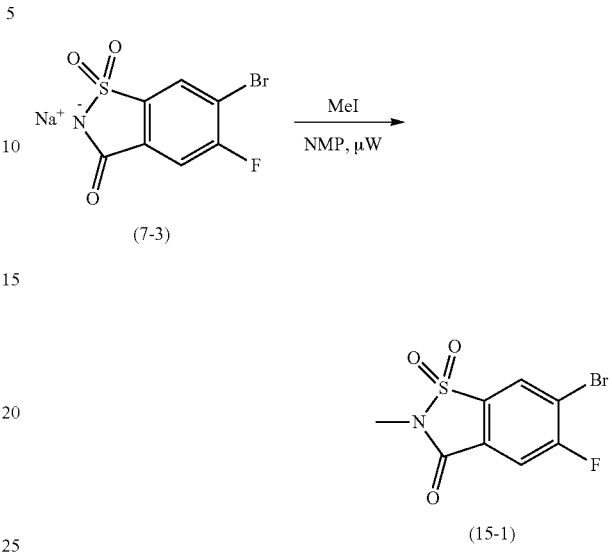

Compound (15-1) was prepared from compound (7-3) according to the general procedure for saccharin derivative alkylation, using MeI as the alkylating agent, and was purified by column chromatography eluting with hexanes/EtOAc (0% EtOAc→20% EtOAc) to afford compound (15-1) (315 mg, 1.07 mmol, 54% yield) as a pale yellow solid: $^1H$ NMR (400 MHz, Chloroform-d) δ 8.16 (d, J=5.4 Hz, 1H), 7.76 (d, J=6.7 Hz, 1H), 3.27 (s, 3H).

Step 15-2: Synthesis of 6-bromo-5-fluoro-2-methyl-2,3-dihydrobenzo[d]isothiazole 1,1-dioxide

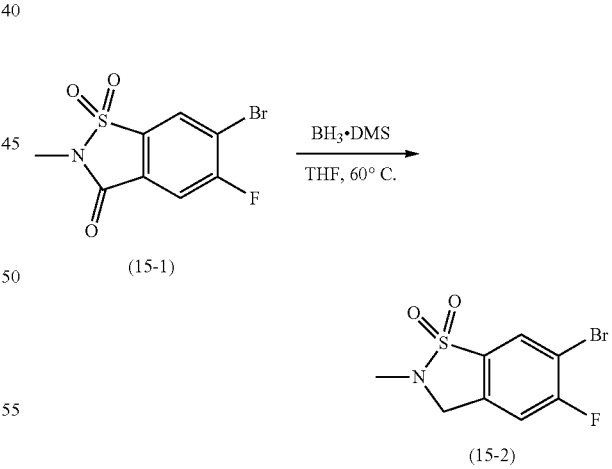

Compound (15-2) was prepared from compound (15-1) according to the general procedure for saccharin derivative reduction, and was purified by column chromatography eluting with hexanes/EtOAc (0% EtOAc→40% EtOAc) to afford compound (15-2) (209 mg, 0.75 mmol, 71% yield) as a white solid: $^1H$ NMR (400 MHz, Chloroform-d) δ 8.02 (d, J=6.0 Hz, 1H), 7.15 (dt, J=7.5, 0.9 Hz, 1H), 4.29 (s, 2H), 2.95 (s, 3H).

Step 15-3: Synthesis of ethyl 5-fluoro-2-methyl-2,3-dihydrobenzo[d]isothiazole-6-carboxylate 1,1-dioxide

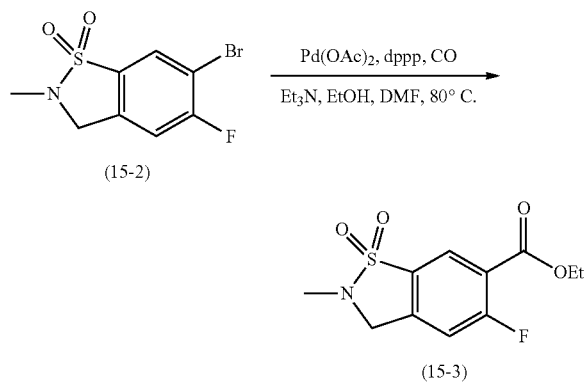

Compound (15-3) was prepared from compound (15-2) according to the general procedure for carbonylation, and was purified by column chromatography eluting with hexanes/EtOAc (0% EtOAc→50% EtOAc) to afford compound (15-3) (82.6 mg, 0.30 mmol, 41% yield) as a pale yellow solid: $^1$H NMR (500 MHz, Chloroform-d) δ 8.43 (d, J=6.3 Hz, 1H), 7.18 (d, J=9.6 Hz, 1H), 4.42 (q, J=7.1 Hz, 2H), 4.36 (s, 2H), 2.97 (s, 3H), 1.41 (t, J=7.2 Hz, 3H).

Step 15-4: Synthesis of 5-fluoro-2-methyl-2,3-dihydrobenzo[d]isothiazole-6-carboxylic acid 1,1-dioxide

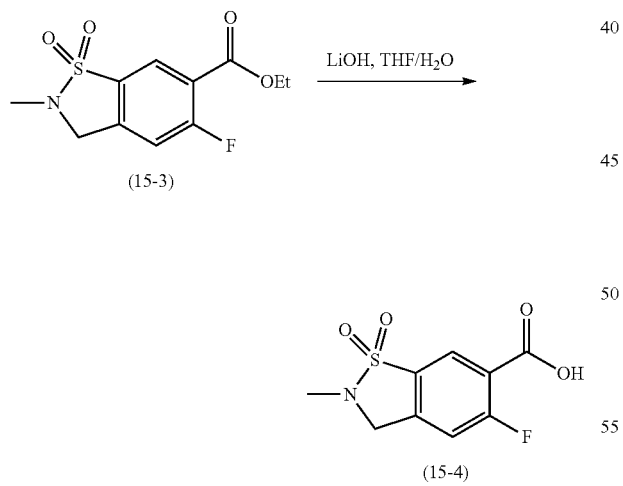

Compound (15-4) was prepared from compound (15-3) according to the general procedure for ester hydrolysis, and was purified by HPLC eluting with CH$_3$CN/H$_2$O (35% CH$_3$CN→95% CH$_3$CN over 20 minutes) to afford compound (15-4) (44.6 mg, 0.18 mmol, 60% yield) as a fluffy white solid: $^1$H NMR (400 MHz, DMSO-d$_6$) δ 13.79 (s, 1H), 8.24 (d, J=6.3 Hz, 1H), 7.65 (d, J=10.5 Hz, 1H), 4.47 (s, 2H), 2.83 (s, 3H).

Step 15-5: Synthesis of 5-fluoro-N-(6-(4-isopropyl-4H-1,2,4-triazol-3-yl)pyridin-2-yl)-2-methyl-2,3-dihydrobenzo[d]isothiazole-6-carboxamide 1,1-dioxide

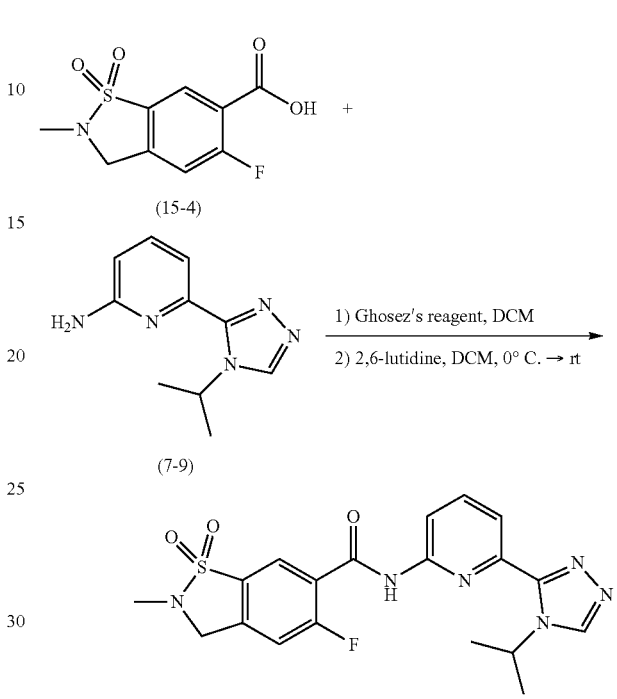

Example 15 was prepared from compounds (15-4) and (7-9) according to the general procedure for amide formation with Ghosez's reagent, using 2,6-luditine as the base instead of pyridine, and was purified by column chromatography eluting with CH$_2$Cl$_2$/MeOH (0% MeOH→8% MeOH) to afford pure compound 15 (10.4 mg, 0.024 mmol, 29%) as a clear gum: $^1$H NMR (400 MHz, Chloroform-d) δ 8.96 (d, J=13.7 Hz, 1H), 8.67 (d, J=6.7 Hz, 1H), 8.46-8.38 (comp, 2H), 8.09 (dd, J=7.7, 0.8 Hz, 1H), 7.95 (t, J=8.0 Hz, 1H), 7.27 (d, J=11.1 Hz, 1H), 5.48 (hept, J=6.8 Hz, 1H), 4.40 (s, 2H), 2.98 (s, 3H), 1.59 (d, J=6.7 Hz, 6H); LCMS (ESI) m/z 431.2 (M+1).

Example 16: N-(6-(4-isopropyl-4H-1,2,4-triazol-3-yl)pyridin-2-yl)-5-methoxy-2-methyl-2,3-dihydrobenzo[d]isothiazole-6-carboxamide 1,1-dioxide

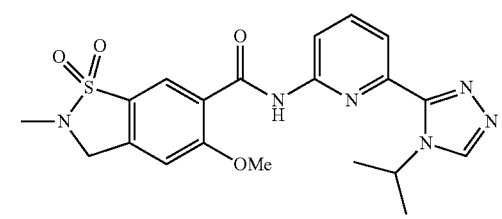

Step 16-1: Synthesis of N-(6-(4-isopropyl-4H-1,2,4-triazol-3-yl)pyridin-2-yl)-5-methoxy-2-methyl-2,3-dihydrobenzo[d]isothiazole-6-carboxamide 1,1-dioxide Step 17-1: Synthesis of (R)-5-fluoro-N-(6-(1-(1-hydroxypropan-2-yl)-1H-tetrazol-5-yl)pyridin-2-yl)-2-methyl-2,3-dihydrobenzo[d]isothiazole-6-carboxamide 1,1-dioxide

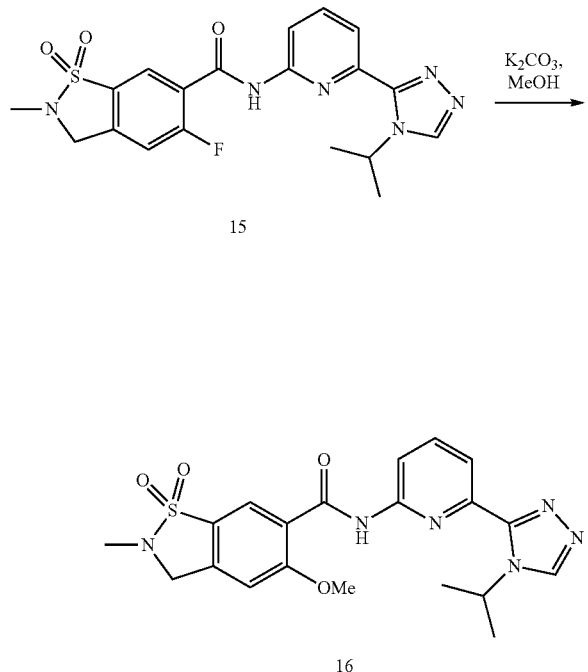

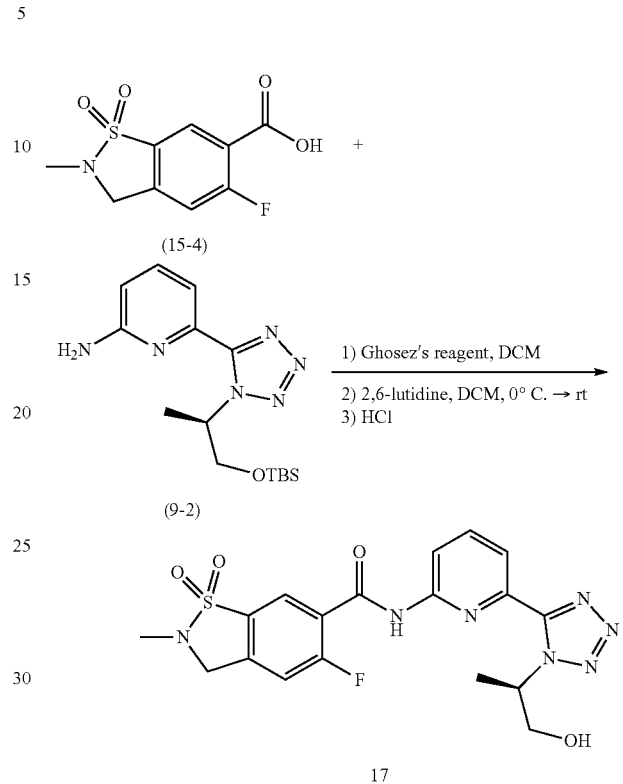

Example 16 was prepared from compound 15 according to the general procedure for fluoride displacement to afford pure compound 16 (5.0 mg, 0.011 mmol, 94% yield) as a colorless solid: $^1$H NMR (500 MHz, Chloroform-d) δ 10.09 (s, 1H), 8.78 (s, 1H), 8.47 (dd, J=8.2, 1.0 Hz, 1H), 8.38 (s, 1H), 8.02 (dd, J=7.7, 1.0 Hz, 1H), 7.92 (t, J=8.0 Hz, 1H), 7.02 (s, 1H), 5.49 (hept, J=6.5 Hz, 1H), 4.37 (s, 2H), 4.14 (s, 3H), 2.97 (s, 3H), 1.62 (d, J=6.8 Hz, 6H); LCMS (ESI) m/z 443.2 (M+1).

Example 17 was prepared from compounds (15-4) and (9-2) according to the general procedure for amide formation with Ghosez's reagent followed by TBS deprotection, using 2,6-luditine as the base instead of pyridine, and was purified by column chromatography eluting with CH$_2$Cl$_2$/MeOH (0% MeOH→8% MeOH) to afford pure compound 17 (10.5 mg, 0.023 mmol, 28%) as a clear gum: $^1$H NMR (400 MHz, Chloroform-d) δ 9.08 (d, J=13.2 Hz, 1H), 8.62 (d, J=6.6 Hz, 1H), 8.46 (dd, J=8.3, 0.9 Hz, 1H), 8.10 (dd, J=7.6, 1.0 Hz, 1H), 8.02 (t, J=8.0 Hz, 1H), 7.27 (d, J=11.7 Hz, 1H), 5.75-5.67 (m, 1H), 4.40 (s, 2H), 4.17 (dd, J=11.8, 7.9 Hz, 1H), 4.09 (dd, J=11.8, 4.2 Hz, 1H), 2.98 (s, 3H), 1.68 (d, J=6.8 Hz, 3H); LCMS (ESI) m/z 448.1 (M+1).

Example 17: (R)-5-fluoro-N-(6-(1-(1-hydroxypropan-2-yl)-1H-tetrazol-5-yl)pyridin-2-yl)-2-methyl-2,3-dihydrobenzo[d]isothiazole-6-carboxamide 1,1-dioxide Example 18: (R)—N-(6-(1-(1-hydroxypropan-2-yl)-1H-tetrazol-5-yl)pyridin-2-yl)-5-methoxy-2-methyl-2,3-dihydrobenzo[d]isothiazole-6-carboxamide 1,1-dioxide

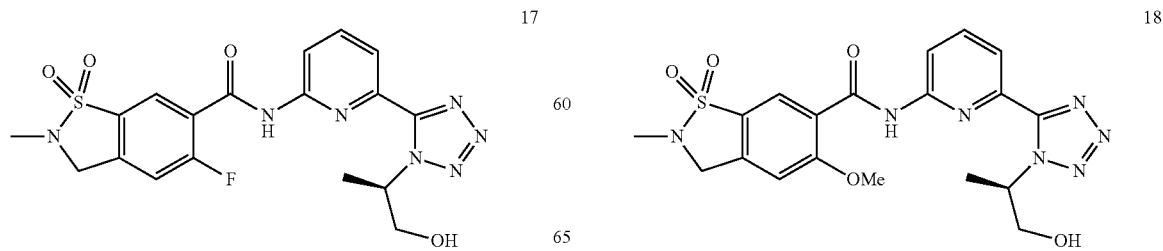

Step 18-1: Synthesis of (R)—N-(6-(1-(1-hydroxy-propan-2-yl)-1H-tetrazol-5-yl)pyridin-2-yl)-5-methoxy-2-methyl-2,3-dihydrobenzo[d]isothiazole-6-carboxamide 1,1-dioxide

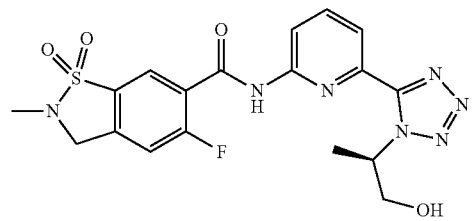

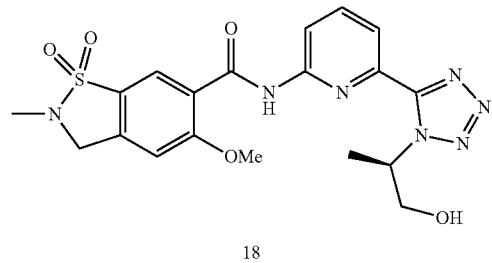

Example 18 was prepared from compound 17 according to the general procedure for fluoride displacement to afford pure compound 18 (4.7 mg, 0.010 mmol, 86% yield) as a colorless solid: $^1$H NMR (400 MHz, DMSO-d$_6$) δ 10.93 (s, 1H), 8.37 (d, J=8.4 Hz, 1H), 8.16-8.10 (comp, 2H), 7.97 (dd, J=7.6, 0.9 Hz, 1H), 7.46 (s, 1H), 5.93-5.80 (m, 1H), 4.95 (s, 1H), 4.45 (s, 2H), 3.99 (s, 3H), 3.83-3.69 (comp, 2H), 2.83 (s, 3H), 1.56 (d, J=6.8 Hz, 3H); LCMS (ESI) m/z 460.2 (M+1).

Example 19: 5-fluoro-N-(6-(4-isopropyl-4H-1,2,4-triazol-3-yl)pyridin-2-yl)-2-(2-methoxyethyl)-2,3-dihydrobenzo[d]isothiazole-6-carboxamide 1,1-dioxide

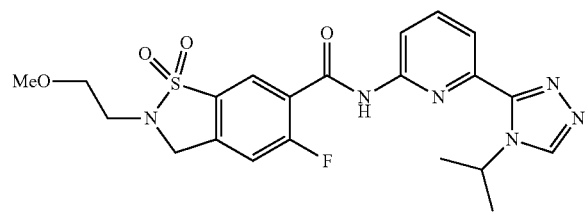

Step 19-1: Synthesis of 6-bromo-5-fluoro-2-(2-methoxyethyl)benzo[d]isothiazol-3 (2H)-one 1,1-dioxide

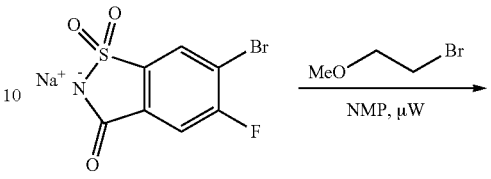

(7-3)

Compound (19-1) was prepared from compound (7-3) according to the general procedure for saccharin derivative alkylation, using 1-bromo-2-methoxyethane as the alkylating agent, and was purified by column chromatography eluting with hexanes/EtOAc (0% EtOAc→20% EtOAc) to afford compound (19-1) (311 mg, 0.92 mmol, 46% yield) as a tan solid: $^1$H NMR (400 MHz, Chloroform-d) δ 8.15 (d, J=5.4 Hz, 1H), 7.75 (d, J=6.7 Hz, 1H), 3.97 (t, J=5.9 Hz, 2H), 3.73 (t, J=5.9 Hz, 2H), 3.40 (s, 3H).

Step 19-2: Synthesis of 6-bromo-5-fluoro-2-(2-methoxyethyl)-2,3-dihydrobenzo[d]isothiazole 1,1-dioxide

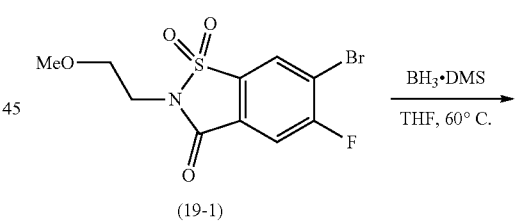

Compound (19-2) was prepared from compound (19-1) according to the general procedure for saccharin derivative reduction, and was purified by column chromatography eluting with hexanes/EtOAc (0% EtOAc→45% EtOAc) to afford compound (19-2) (228 mg, 0.70 mmol, 77% yield) as a white solid: $^1$H NMR (400 MHz, Chloroform-d) δ 8.01 (d, J=6.0 Hz, 1H), 7.14 (dt, J=7.6, 0.9 Hz, 1H), 4.48 (s, 2H), 3.70 (dd, J=5.3, 4.5 Hz, 2H), 3.48 (dd, J=5.3, 4.5 Hz, 2H) 3.39 (d, J=0.6 Hz, 3H)

Step 19-3: Synthesis of ethyl 5-fluoro-2-(2-methoxyethyl)-2,3-dihydrobenzo[d]isothiazole-6-carboxylate 1,1-dioxide

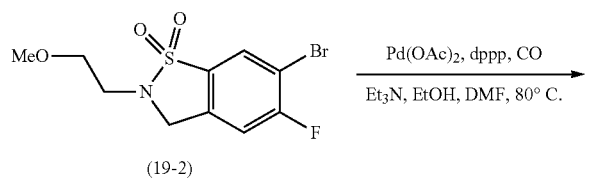

Compound (19-3) was prepared from compound (19-2) according to the general procedure for carbonylation, and was purified by column chromatography eluting with hexanes/EtOAc (0% EtOAc→50% EtOAc) to afford compound (19-3) (88.2 mg, 0.28 mmol, 40% yield) as a colorless oil: $^1$H NMR (500 MHz, Chloroform-d) δ 8.42 (d, J=6.2 Hz, 1H), 7.17 (d, J=9.7 Hz, 1H), 4.56 (s, 2H), 4.42 (q, J=7.1 Hz, 2H), 3.71 (t, J=5.0 Hz, 2H), 3.50 (t, J=5.0 Hz, 2H), 3.40 (s, 3H), 1.41 (t, J=7.1 Hz, 3H).

Step 19-4: Synthesis of 5-fluoro-2-(2-methoxyethyl)-2,3-dihydrobenzo[d]isothiazole-6-carboxylic Acid 1,1-dioxide

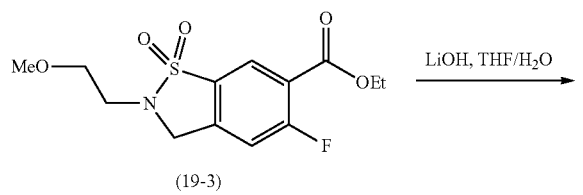

Compound (19-4) was prepared from compound (19-3) according to the general procedure for ester hydrolysis, and was purified by HPLC eluting with CH$_3$CN/H$_2$O (35% CH$_3$CN→95% CH$_3$CN over 20 minutes) to afford compound (19-4) (55.2 mg, 0.19 mmol, 69% yield) as a fluffy white solid: $^1$H NMR (400 MHz, DMSO-d$_6$) δ 13.79 (s, 1H), 8.24 (d, J=6.3 Hz, 1H), 7.65 (d, J=10.4 Hz, 1H), 4.59 (s, 2H), 3.61 (dd, J=5.6, 4.9 Hz, 2H), 3.38 (t, J=5.3 Hz, 2H), 3.30 (s, 3H).

Step 19-5: Synthesis of 5-fluoro-N-(6-(4-isopropyl-4H-1,2,4-triazol-3-yl)pyridin-2-yl)-2-(2-methoxyethyl)-2,3-dihydrobenzo[d]isothiazole-6-carboxamide 1,1-dioxide

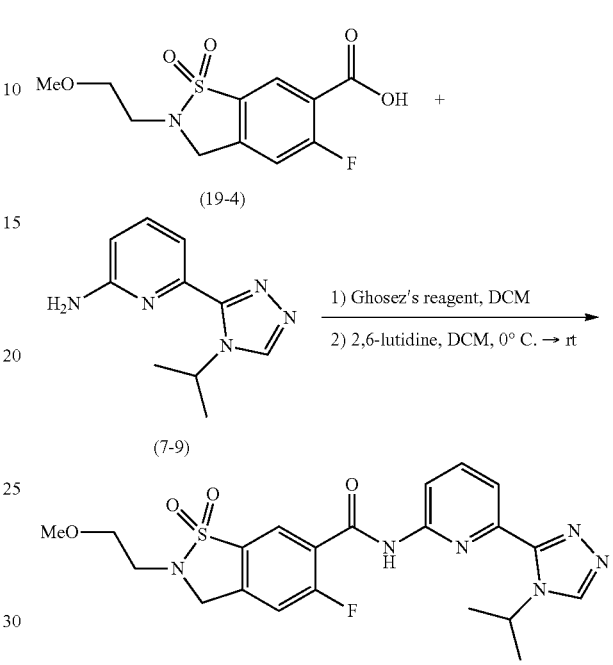

Example 19 was prepared from compounds (19-4) and (7-9) according to the general procedure for amide formation with Ghosez's reagent, using 2,6-luditine as the base instead of pyridine, and was purified by column chromatography eluting with CH$_2$Cl$_2$/MeOH (0% MeOH→8% MeOH) to afford pure compound 19 (18 mg, 0.038 mmol, 45%) as a clear gum: $^1$H NMR (400 MHz, Chloroform-d) δ 8.97 (d, J=13.8 Hz, 1H), 8.66 (d, J=6.7 Hz, 1H), 8.42 (dd, J=8.4, 0.9 Hz, 1H), 8.40 (s, 1H), 8.08 (dd, J=7.7, 0.8 Hz, 1H), 7.95 (t, J=8.0 Hz, 1H), 7.26 (d, J=11.1 Hz, 1H), 5.48 (hept, J=6.7 Hz, 1H), 4.60 (s, 2H), 3.72 (t, J=4.9 Hz, 2H), 3.51 (t, J=4.9 Hz, 2H), 3.40 (s, 3H), 1.59 (d, J=6.7 Hz, 6H); LCMS (ESI) m/z 475.2 (M+1).

Example 20: N-(6-(4-isopropyl-4H-1,2,4-triazol-3-yl)pyridin-2-yl)-5-methoxy-2-(2-methoxyethyl)-2,3-dihydrobenzo[d]isothiazole-6-carboxamide 1,1-dioxide

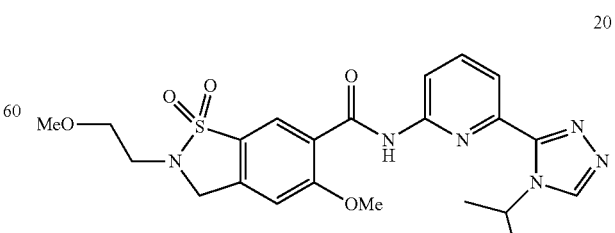

Step 20-1: Synthesis of N-(6-(4-isopropyl-4H-1,2,4-triazol-3-yl)pyridin-2-yl)-5-methoxy-2-(2-methoxyethyl)-2,3-dihydrobenzo[d]isothiazole-6-carboxamide 1,1-dioxide Step 21-1: Synthesis of (R)-5-fluoro-N-(6-(1-(1-hydroxypropan-2-yl)-1H-tetrazol-5-yl)pyridin-2-yl)-2-(2-methoxyethyl)-2,3-dihydrobenzo[d]isothiazole-6-carboxamide 1,1-dioxide

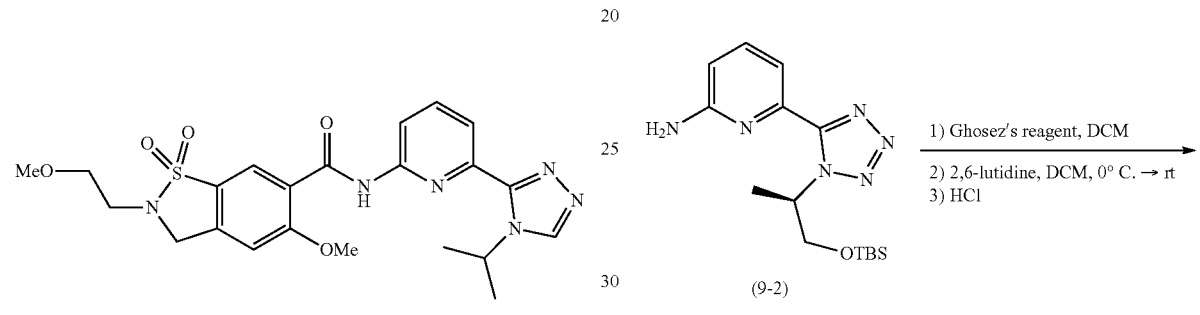

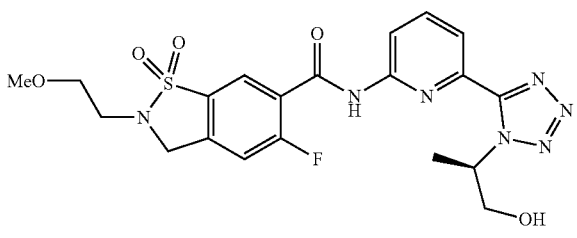

Example 20 was prepared from compound 19 according to the general procedure for fluoride displacement to afford pure compound 20 (8.2 mg, 0.017 mmol, 89% yield) as a colorless solid: ¹H NMR (500 MHz, Chloroform-d) δ 10.11 (s, 1H), 8.76 (s, 1H), 8.45 (dd, J=8.4, 0.9 Hz, 1H), 8.37 (s, 1H), 8.01 (dd, J=7.7, 1.0 Hz, 1H), 7.91 (t, J=8.0 Hz, 1H), 7.02 (s, 1H), 5.49 (hept, J=6.8 Hz, 1H), 4.56 (s, 2H), 4.13 (s, 3H), 3.73 (t, J=5.0 Hz, 2H), 3.50 (t, J=5.0 Hz, 2H), 3.40 (s, 3H), 1.62 (d, J=6.8 Hz, 6H); LCMS (ESI) m/z 487.2 (M+1).

Example 21: (R)-5-fluoro-N-(6-(1-(1-hydroxypropan-2-yl)-1H-tetrazol-5-yl)pyridin-2-yl)-2-(2-methoxyethyl)-2,3-dihydrobenzo[d]isothiazole-6-carboxamide 1,1-dioxide

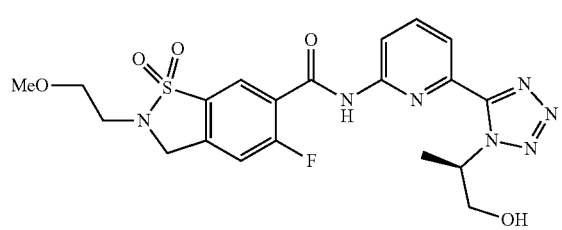

Example 21 was prepared from compounds (19-4) and (9-2) according to the general procedure for amide formation with Ghosez's reagent followed by TBS deprotection, using 2,6-luditine as the base instead of pyridine, and was purified by column chromatography eluting with CH₂Cl₂/MeOH (0% MeOH→8% MeOH) to afford pure compound 21 (17.8 mg, 0.036 mmol, 43%) as a yellow gum: ¹H NMR (400 MHz, Chloroform-d) δ 9.13 (d, J=13.0 Hz, 1H), 8.59 (d, J=6.6 Hz, 1H), 8.44 (dd, J=8.3, 1.0 Hz, 1H), 8.08 (dd, J=7.6, 1.0 Hz, 1H), 8.00 (t, J=8.0 Hz, 1H), 7.26 (d, J=10.9 Hz, 1H), 5.78-5.64 (m, 1H), 4.59 (s, 2H), 4.15 (dd, J=11.8, 7.9 Hz, 1H), 4.07 (dd, J=11.8, 4.2 Hz, 1H), 3.72 (t, J=4.9 Hz, 2H), 3.50 (t, J=4.9 Hz, 2H), 3.40 (s, 3H), 1.67 (d, J=6.8 Hz, 3H); LCMS (ESI) m/z 492.2 (M+1).

Example 22: (R)—N-(6-(1-(1-hydroxypropan-2-yl)-1H-tetrazol-5-yl)pyridin-2-yl)-5-methoxy-2-(2-methoxyethyl)-2,3-dihydrobenzo[d]isothiazole-6-carboxamide 1,1-dioxide

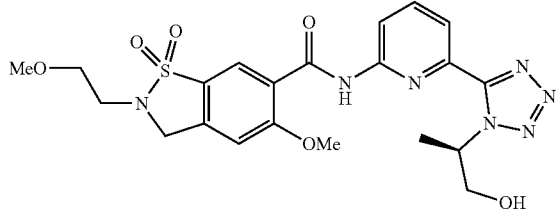

22

Step 22-1: Synthesis of (R)—N-(6-(1-(1-hydroxypropan-2-yl)-1H-tetrazol-5-yl)pyridin-2-yl)-5-methoxy-2-(2-methoxyethyl)-2,3-dihydrobenzo[d]isothiazole-6-carboxamide 1,1-dioxide

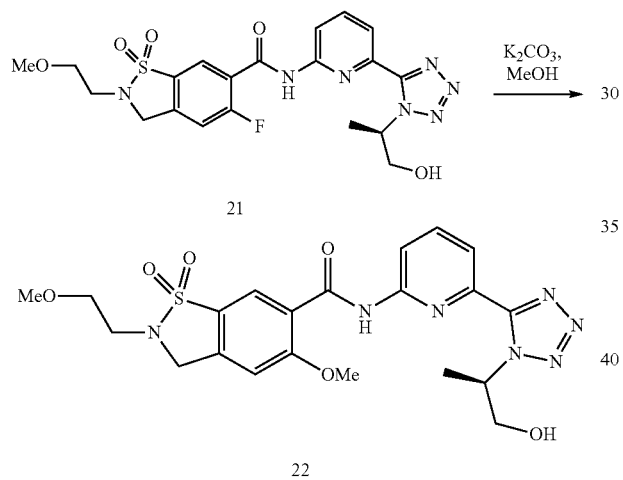

Example 22 was prepared from compound 21 according to the general procedure for fluoride displacement to afford pure compound 22 (8.3 mg, 0.018 mmol, 91% yield) as a colorless solid: $^1$H NMR (500 MHz, Chloroform-d) δ 10.37 (s, 1H), 8.75 (s, 1H), 8.54 (dd, J=7.3, 2.0 Hz, 1H), 8.06-7.95 (m, 2H), 7.03 (s, 1H), 5.66-5.54 (m, 1H), 4.56 (s, 2H), 4.19 (s, 3H), 4.15-4.12 (m, 2H), 3.84-3.80 (m, 1H), 3.72 (t, J=5.0 Hz, 2H), 3.49 (t, J=4.9 Hz, 2H), 3.41 (s, 3H), 1.72 (d, J=6.8 Hz, 3H); LCMS (ESI) m/z 504.2 (M+1).

Assay

HTRF® KinEASE™ Assay

ASK1 was purchased from Thermofisher (Catalogue # PV4011), ATP was purchased from Sigma (Catalogue # A7699), HTRF® KinEASE™ Assay System was obtained from Cisbio (Bedford, Mass.). ½ Area plate was purchased from Perkin Elmer (Catalogue # #6005560). HTRF® KinEASE™-STK is a generic method for measuring serine/threonine kinase activities using a time-resolved fluorescence resonance energy transfer (TR-FRET) immunoassay. The $IC_{50}$ value for each compound was determined in the presence of compound (various concentration from 0 to 10 μM) and a fixed amount of ATP and peptide substrates. The test compound, 1 uM STK3 peptide substrate, and 5 nM of ASK1 kinase are incubated with kinase reaction buffer containing 50 mM HEPES pH 7.5, 0.01% BRIJ-35, 10 mM $MgCl2$, and 1 mM EGTA for 30 minutes. 100 uM ATP is added to start kinase reaction and incubated for 3 hours. The STK3-antibody labeled with $Eu^{3+}$-Cryptate and 125 nM streptavidin-XL665 are mixed in a single addition with stop reagents provided by the Cisbio kit used to stop the kinase reaction. Fluorescence is detected using an Envision Multilabeled 2014 reader from PerkinElmer. The Fluorescence is measured at 615 nm (Cryptate) and 665 nm (XL665) and a ratio of 665 nm/615 nm is calculated for each well. The resulting TR-FRET is proportional to the phosphorylation level. Staurosporine was used as the positive control. $IC_{50}$ was determined by XLfit 5.3. By using above method, the inhibition of ASK1 was evaluated for the compounds of Formula (I). For example (A=$IC_{50}$<1.5 nM; B=1.5 nM<$IC_{50}$<10 nM; C=10 nM<$IC_{50}$<100 nM; D=100 nM<$IC_{50}$<1 μM; E=$IC_{50}$>1 μM):

| Example | $IC_{50}$ range |
| --- | --- |
| Staurosporine | C |
| 1 | D |
| 2 | C |
| 3 | B |
| 4 | C |
| 5 | B |
| 6 | E |
| 7 | C |
| 8 | A |
| 9 | C |
| 10 | A |
| 11 | B |
| 12 | D |
| 13 | C |
| 14 | C |
| 15 | C |
| 16 | A |
| 17 | C |
| 18 | A |
| 19 | C |
| 20 | C |
| 21 | A |
| 22 | A |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by Formula I, or a pharmaceutically acceptable salt thereof:

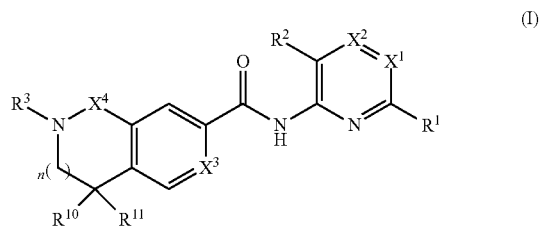

wherein $R^1$ is selected from

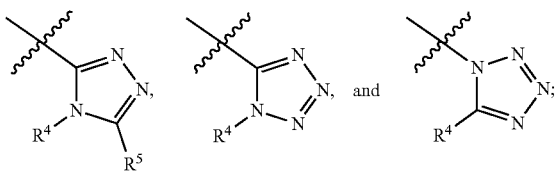

$X^1$ and $X^2$ are each independently $C(R^8)$ or N;
$X^3$ is $C(R^9)$ or N;
$R^9$ is selected from the group consisting of hydrogen, optionally substituted —$C_1$-$C_8$ alkyl, optionally substituted —$C_1$-$C_8$ alkoxy and halogen;
$X^4$ is S, S(O), or $SO_2$;
$R^4$ is selected from the group consisting of:
  1) Hydrogen;
  2) Substituted or unsubstituted —$C_1$-$C_8$ alkyl;
  3) Substituted or unsubstituted —$C_2$-$C_8$ alkenyl;
  4) Substituted or unsubstituted —$C_2$-$C_8$ alkynyl;
  5) Substituted or unsubstituted —$C_3$-$C_8$ cycloalkyl;
  6) Substituted or unsubstituted aryl;
  7) Substituted or unsubstituted arylalkyl;
  8) Substituted or unsubstituted 3- to 8-membered heterocycloalkyl;
  9) Substituted or unsubstituted heteroaryl; and
  10) Substituted or unsubstituted heteroarylalkyl;
$R^2$, $R^5$ and $R^8$ are each independently selected from the group consisting of:
  1) Hydrogen;
  2) Halogen;
  3) —$NO_2$;
  4) Cyano;
  5) Substituted or unsubstituted —$C_1$-$C_8$ alkyl;
  6) Substituted or unsubstituted —$C_2$-$C_8$ alkenyl;
  7) Substituted or unsubstituted —$C_2$-$C_8$ alkynyl;
  8) Substituted or unsubstituted —$C_3$-$C_8$ cycloalkyl;
  9) Substituted or unsubstituted aryl;
  10) Substituted or unsubstituted arylalkyl;
  11) Substituted or unsubstituted 3- to 8-membered heterocycloalkyl;
  12) Substituted or unsubstituted heteroaryl;
  13) Substituted or unsubstituted heteroarylalkyl;
  14) —$N(R^6)(R^7)$;
  15) —$S(O)_2N(R^6)(R^7)$;
  16) —$N(R^6)C(O)R^7$; and
  17) —$N(R^6)S(O)_2R^6$;
    wherein $R^6$ and $R^7$ are independently selected from the group consisting of hydrogen, —$C_1$-$C_8$ alkyl, —$C_1$-$C_8$ alkenyl, —$C_1$-$C_8$ alkynyl, —$C_3$-$C_8$ cycloalkyl, aryl, heterocycloalkyl, heteroaryl, and heteroarylalkyl, all of which are optionally substituted with 1-3 substituents selected from halo, alkyl, alkylamino, dialkylamino, alkylC(O)NH—, arylC(O)NH—, heteroarylC(O)NH—, —CN, alkoxy, —$CF_3$, aryl, and heteroaryl;
alternatively, $R^6$ and $R^7$ are taken together with the nitrogen atom to which they are attached to form an optionally substituted heterocyclic;
$R^3$ is selected from the group consisting of:
  1) Substituted or unsubstituted —$C_1$-$C_8$ alkyl;
  2) Substituted or unsubstituted —$C_2$-$C_8$ alkenyl;
  3) Substituted or unsubstituted —$C_2$-$C_8$ alkynyl;
  4) Substituted or unsubstituted —$C_3$-$C_8$ cycloalkyl;
  5) Substituted or unsubstituted aryl;
  6) Substituted or unsubstituted arylalkyl;
  7) Substituted or unsubstituted 3- to 8-membered heterocycloalkyl;
  8) Substituted or unsubstituted heteroaryl;
  9) Substituted or unsubstituted heteroarylalkyl;
  10) —$C(O)R^6$;
  11) —$C(O)OR^6$;
  12) —$C(O)N(R^6)(R')$;
  13) —$SO_2R^6$; and
  14) hydrogen $R^{10}$ and $R^{11}$ are each independently selected from the group consisting of hydrogen, halogen, optionally substituted —$C_1$-$C_8$ alkyl; alternatively, $R^{10}$ and $R^{11}$ are taken together with the carbon to which they are attached to form an optionally substituted cycloalkyl, cycloalkenyl or heterocyclic; and n is 0, 1 or 2.

2. The compound of claim 1, wherein $R^3$ is one of the following groups,

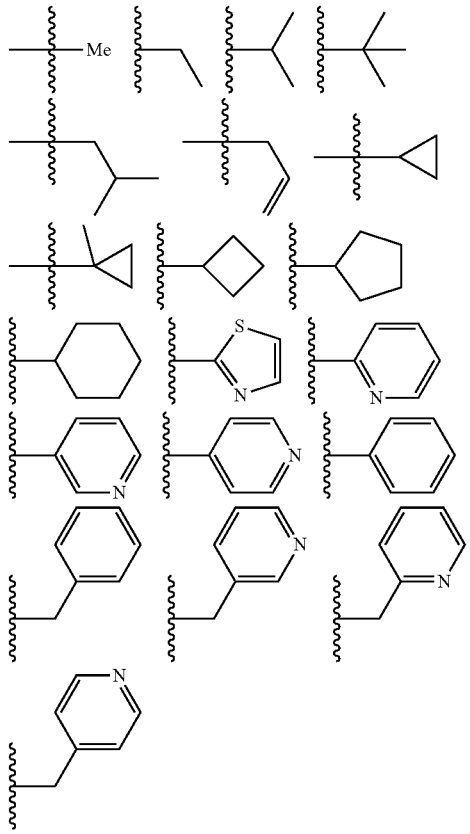

wherein each group is optionally substituted.

3. The compound of claim 1, wherein $R^4$ is one of the following groups,

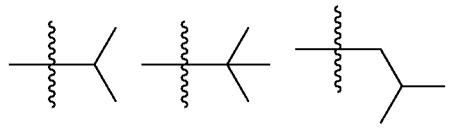

-continued

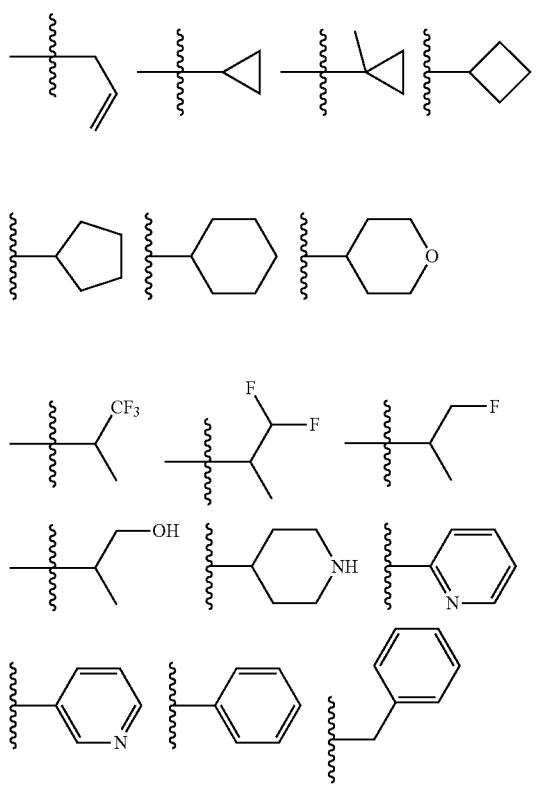

wherein each group is optionally substituted.

4. The compound of claim 1, represented by Formula Ib or a pharmaceutically acceptable salt thereof:

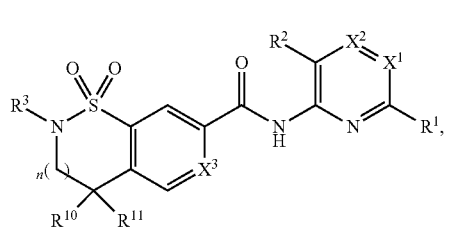

(Ib)

wherein $R^1$, $R^2$, $R^3$, $R^{10}$, $R^{11}$, $X^1$, $X^2$, $X^3$ and n are as defined in claim 1.

5. The compound of claim 1, represented by Formula II or a pharmaceutically acceptable salt thereof:

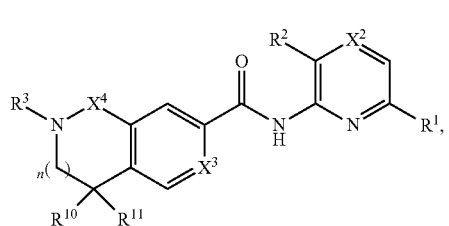

(II)

wherein $R^1$, $R^2$, $R^3$, $R^{10}$, $R^{11}$, $X^2$, $X^3$, $X^4$ and n are as defined in claim 1.

6. The compound of claim 1 represented by Formula III or a pharmaceutically acceptable salt thereof:

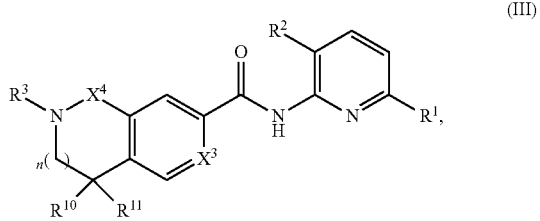

(III)

wherein $R^1$, $R^2$, $R^3$, $R^{10}$, R, $X^3$, $X^4$ and n are as defined in claim 1.

7. The compound of claim 1 represented by Formula IV or a pharmaceutically acceptable salt thereof:

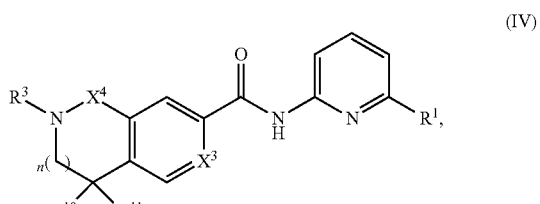

(IV)

wherein $R^1$, $R^3$, $R^{10}$, $R^{11}$, $X^3$, $X^4$ and n are as defined in claim 1.

8. The compound of claim 1 represented by Formula V or Formula XIII, or a pharmaceutically acceptable salt thereof:

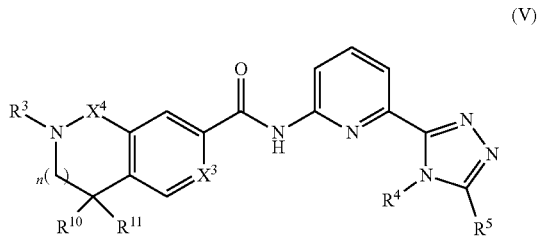

(V)

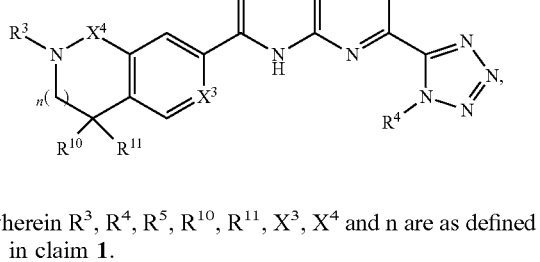

(XIII)

wherein $R^3$, $R^4$, $R^5$, $R^{10}$, $R^{11}$, $X^3$, $X^4$ and n are as defined in claim 1.

9. The compound of claim 1 represented by Formula VII, Formula X, Formula XIV, or Formula XVII, or a pharmaceutically acceptable salt thereof:

(VII)

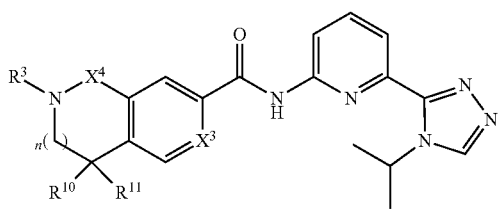

(X)

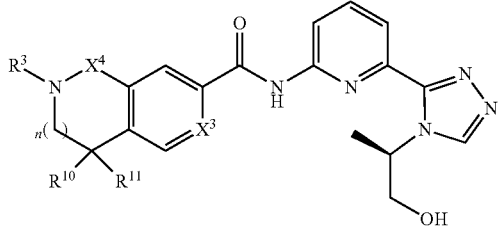

(XIV)

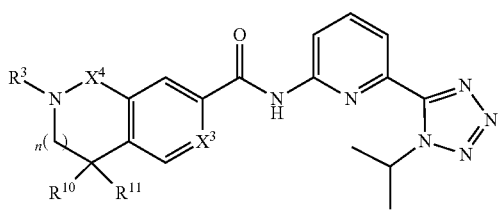

(XVII)

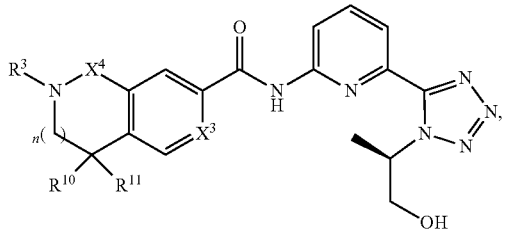

wherein $R^3$, $R^{10}$, $R^{11}$, $X^3$, $X^4$ and n are as defined in claim 1.

10. The compound of claim 1 represented by Formula VIII, or Formula XI, Formula XV, or Formula XVIII, or a pharmaceutically acceptable salt thereof:

(VIII)

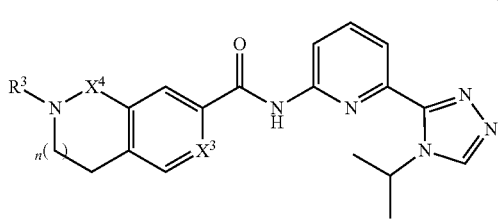

(XI)

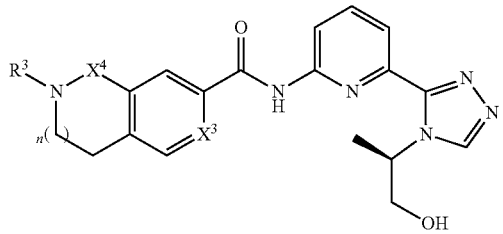

(XV)

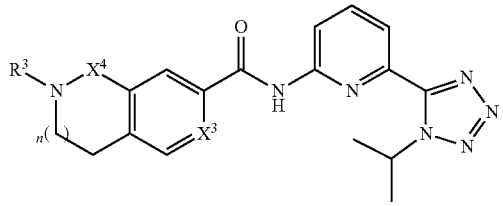

(XVIII)

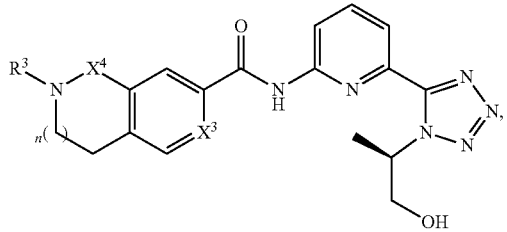

wherein $R^3$, $X^3$, $X^4$ and n are as defined in claim 1.

11. The compound of claim 1, which is selected from compounds of Formula IX, or a pharmaceutically acceptable salt thereof:

(IX)

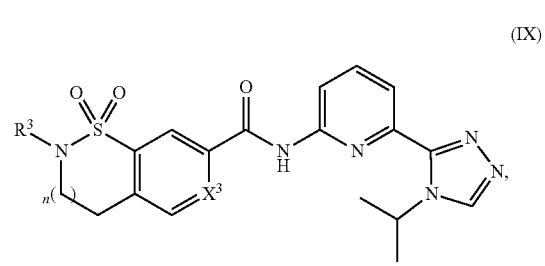

wherein $R^3$, $X^3$, and n are delineated for each compound in Table 1:

TABLE 1

| compound | $R^3$ | $X^3$ | n |
|---|---|---|---|
| 1 | H | C—H | 0 |
| 2 | Methyl | C—H | 0 |
| 3 | Ethyl | C—H | 0 |
| 4 | Propyl | C—H | 0 |
| 5 | Allyl | C—H | 0 |
| 6 | i-Propyl | C—H | 0 |
| 7 | ▽ | C—H | 0 |

TABLE 1-continued

| compound | R³ | X³ | n |
|---|---|---|---|
| 8 | i-Butyl | C—H | 0 |
| 9 | sec-Butyl | C—H | 0 |
| 10 | t-Butyl | C—H | 0 |
| 11 | cyclobutyl | C—H | 0 |
| 12 | -CH₂CH₂OMe | C—H | 0 |
| 13 | -CH₂CH₂OH | C—H | 0 |
| 14 | -CH₂CH₂CF₃ | C—H | 0 |
| 15 | cyclopentyl | C—H | 0 |
| 16 | cyclohexyl | C—H | 0 |
| 17 | Ph | C—H | 0 |
| 18 | H | C—F | 0 |
| 19 | Methyl | C—F | 0 |
| 20 | Ethyl | C—F | 0 |
| 21 | Propyl | C—F | 0 |
| 22 | Allyl | C—F | 0 |
| 23 | i-Propyl | C—F | 0 |
| 24 | cyclopropyl | C—F | 0 |
| 25 | i-Butyl | C—F | 0 |
| 26 | sec-Butyl | C—F | 0 |
| 27 | t-Butyl | C—F | 0 |
| 28 | cyclobutyl | C—F | 0 |
| 29 | -CH₂CH₂OMe | C—F | 0 |
| 30 | -CH₂CH₂OH | C—F | 0 |
| 31 | -CH₂CH₂CF₃ | C—F | 0 |
| 32 | cyclopentyl | C—F | 0 |
| 33 | cyclohexyl | C—F | 0 |
| 34 | Ph | C—F | 0 |
| 35 | H | C—OMe | 0 |
| 36 | Methyl | C—OMe | 0 |
| 37 | Ethyl | C—OMe | 0 |
| 38 | Propyl | C—OMe | 0 |
| 39 | Allyl | C—OMe | 0 |
| 40 | i-Propyl | C—OMe | 0 |
| 41 | cyclopropyl | C—OMe | 0 |
| 42 | i-Butyl | C—OMe | 0 |
| 43 | sec-Butyl | C—OMe | 0 |
| 44 | t-Butyl | C—OMe | 0 |
| 45 | cyclobutyl | C—OMe | 0 |
| 46 | -CH₂CH₂OMe | C—OMe | 0 |
| 47 | -CH₂CH₂OH | C—OMe | 0 |
| 48 | -CH₂CH₂CF₃ | C—OMe | 0 |
| 49 | cyclopentyl | C—OMe | 0 |
| 50 | cyclohexyl | C—OMe | 0 |
| 51 | Ph | C—OMe | 0 |
| 52 | H | N | 0 |
| 53 | Methyl | N | 0 |
| 54 | Ethyl | N | 0 |
| 55 | Propyl | N | 0 |
| 56 | Allyl | N | 0 |
| 57 | i-Propyl | N | 0 |

TABLE 1-continued

| compound | R³ | X³ | n |
|---|---|---|---|
| 58 | cyclopropyl | N | 0 |
| 59 | i-Butyl | N | 0 |
| 60 | sec-Butyl | N | 0 |
| 61 | t-Butyl | N | 0 |
| 62 | cyclobutyl | N | 0 |
| 63 | -CH₂CH₂-OMe | N | 0 |
| 64 | -CH₂CH₂-OH | N | 0 |
| 65 | -CH₂CH₂-CF₃ | N | 0 |
| 66 | cyclopentyl | N | 0 |
| 67 | cyclohexyl | N | 0 |
| 68 | -Ph | N | 0 |
| 69 | H | C—H | 1 |
| 70 | Methyl | C—H | 1 |
| 71 | Ethyl | C—H | 1 |
| 72 | Propyl | C—H | 1 |
| 73 | Allyl | C—H | 1 |
| 74 | i-Propyl | C—H | 1 |
| 75 | cyclopropyl | C—H | 1 |
| 76 | i-Butyl | C—H | 1 |
| 77 | sec-Butyl | C—H | 1 |
| 78 | t-Butyl | C—H | 1 |
| 79 | cyclobutyl | C—H | 1 |
| 80 | -CH₂CH₂-OMe | C—H | 1 |
| 81 | -CH₂CH₂-OH | C—H | 1 |
| 82 | -CH₂CH₂-CF₃ | C—H | 1 |
| 83 | cyclopentyl | C—H | 1 |
| 84 | cyclohexyl | C—H | 1 |
| 85 | -Ph | C—H | 1 |
| 86 | H | C—F | 1 |
| 87 | Methyl | C—F | 1 |
| 88 | Ethyl | C—F | 1 |
| 89 | Propyl | C—F | 1 |
| 90 | Allyl | C—F | 1 |
| 91 | i-Propyl | C—F | 1 |
| 92 | cyclopropyl | C—F | 1 |
| 93 | i-Butyl | C—F | 1 |
| 94 | sec-Butyl | C—F | 1 |
| 95 | t-Butyl | C—F | 1 |
| 96 | cyclobutyl | C—F | 1 |
| 97 | -CH₂CH₂-OMe | C—F | 1 |
| 98 | -CH₂CH₂-OH | C—F | 1 |
| 99 | -CH₂CH₂-CF₃ | C—F | 1 |
| 100 | cyclopentyl | C—F | 1 |
| 101 | cyclohexyl | C—F | 1 |
| 102 | -Ph | C—F | 1 |
| 103 | H | C—OMe | 1 |
| 104 | Methyl | C—OMe | 1 |

TABLE 1-continued

| compound | R³ | X³ | n |
|---|---|---|---|
| 105 | Ethyl | C—OMe | 1 |
| 106 | Propyl | C—OMe | 1 |
| 107 | Allyl | C—OMe | 1 |
| 108 | i-Propyl | C—OMe | 1 |
| 109 | cyclopropyl | C—OMe | 1 |
| 110 | i-Butyl | C—OMe | 1 |
| 111 | sec-Butyl | C—OMe | 1 |
| 112 | t-Butyl | C—OMe | 1 |
| 113 | cyclobutyl | C—OMe | 1 |
| 114 | —CH₂CH₂OMe | C—OMe | 1 |
| 115 | —CH₂CH₂OH | C—OMe | 1 |
| 116 | —CH₂CH₂CF₃ | C—OMe | 1 |
| 117 | cyclopentyl | C—OMe | 1 |
| 118 | cyclohexyl | C—OMe | 1 |
| 119 | —Ph | C—OMe | 1 |
| 120 | H | N | 1 |
| 121 | Methyl | N | 1 |
| 122 | Ethyl | N | 1 |
| 123 | Propyl | N | 1 |
| 124 | Allyl | N | 1 |
| 125 | i-Propyl | N | 1 |
| 126 | cyclopropyl | N | 1 |
| 127 | i-Butyl | N | 1 |
| 128 | sec-Butyl | N | 1 |
| 129 | t-Butyl | N | 1 |
| 130 | cyclobutyl | N | 1 |
| 131 | —CH₂CH₂OMe | N | 1 |
| 132 | —CH₂CH₂OH | N | 1 |
| 133 | —CH₂CH₂CF₃ | N | 1 |
| 134 | cyclopentyl | N | 1 |
| 135 | cyclohexyl | N | 1 |
| 136 | —Ph | N | 1. |

12. The compound of claim 1 which is selected from compounds of Formula XII, or a pharmaceutically acceptable salt thereof,

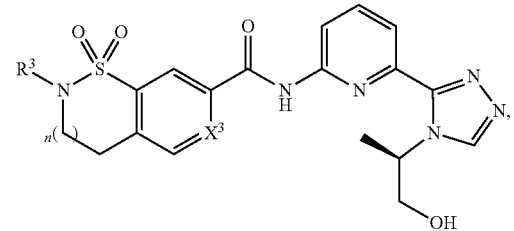

(XII)

wherein R³, X³, and n are delineated for each compound in Table 2:

TABLE 2

| compound | R³ | X³ | n |
|---|---|---|---|
| 137 | H | C—H | 0 |
| 138 | Methyl | C—H | 0 |
| 139 | Ethyl | C—H | 0 |
| 140 | Propyl | C—H | 0 |
| 141 | Allyl | C—H | 0 |
| 142 | i-Propyl | C—H | 0 |
| 143 | cyclopropyl | C—H | 0 |
| 144 | i-Butyl | C—H | 0 |
| 145 | sec-Butyl | C—H | 0 |
| 146 | t-Butyl | C—H | 0 |
| 147 | cyclobutyl | C—H | 0 |

TABLE 2-continued

| compound | R³ | X³ | n |
|---|---|---|---|
| 148 | ~CH2CH2OMe | C—H | 0 |
| 149 | ~CH2CH2OH | C—H | 0 |
| 150 | ~CH2CH2CF3 | C—H | 0 |
| 151 | ~cyclopentyl | C—H | 0 |
| 152 | ~cyclohexyl | C—H | 0 |
| 153 | ~Ph | C—H | 0 |
| 154 | H | C—F | 0 |
| 155 | Methyl | C—F | 0 |
| 156 | Ethyl | C—F | 0 |
| 157 | Propyl | C—F | 0 |
| 158 | Allyl | C—F | 0 |
| 159 | i-Propyl | C—F | 0 |
| 160 | ~cyclopropyl | C—F | 0 |
| 161 | i-Butyl | C—F | 0 |
| 162 | sec-Butyl | C—F | 0 |
| 163 | t-Butyl | C—F | 0 |
| 164 | ~cyclobutyl | C—F | 0 |
| 165 | ~CH2CH2OMe | C—F | 0 |
| 166 | ~CH2CH2OH | C—F | 0 |
| 167 | ~CH2CH2CF3 | C—F | 0 |
| 168 | ~cyclopentyl | C—F | 0 |
| 169 | ~cyclohexyl | C—F | 0 |
| 170 | ~Ph | C—F | 0 |
| 171 | H | C—OMe | 0 |
| 172 | Methyl | C—OMe | 0 |
| 173 | Ethyl | C—OMe | 0 |
| 174 | Propyl | C—OMe | 0 |
| 175 | Allyl | C—OMe | 0 |
| 176 | i-Propyl | C—OMe | 0 |
| 177 | ~cyclopropyl | C—OMe | 0 |
| 178 | i-Butyl | C—OMe | 0 |
| 179 | sec-Butyl | C—OMe | 0 |
| 180 | t-Butyl | C—OMe | 0 |
| 181 | ~cyclobutyl | C—OMe | 0 |
| 182 | ~CH2CH2OMe | C—OMe | 0 |
| 183 | ~CH2CH2OH | C—OMe | 0 |
| 184 | ~CH2CH2CF3 | C—OMe | 0 |
| 185 | ~cyclopentyl | C—OMe | 0 |
| 186 | ~cyclohexyl | C—OMe | 0 |
| 187 | ~Ph | C—OMe | 0 |
| 188 | H | N | 0 |
| 189 | Methyl | N | 0 |
| 190 | Ethyl | N | 0 |
| 191 | Propyl | N | 0 |
| 192 | Allyl | N | 0 |
| 193 | i-Propyl | N | 0 |
| 194 | ~cyclopropyl | N | 0 |

TABLE 2-continued

| compound | R³ | X³ | n |
|---|---|---|---|
| 195 | i-Butyl | N | 0 |
| 196 | sec-Butyl | N | 0 |
| 197 | t-Butyl | N | 0 |
| 198 | cyclobutyl | N | 0 |
| 199 | -CH2CH2-OMe | N | 0 |
| 200 | -CH2CH2-OH | N | 0 |
| 201 | -CH2CH2-CF3 | N | 0 |
| 202 | cyclopentyl | N | 0 |
| 203 | cyclohexyl | N | 0 |
| 204 | Ph | N | 0 |
| 205 | H | C—H | 1 |
| 206 | Methyl | C—H | 1 |
| 207 | Ethyl | C—H | 1 |
| 208 | Propyl | C—H | 1 |
| 209 | Allyl | C—H | 1 |
| 210 | i-Propyl | C—H | 1 |
| 211 | cyclopropyl | C—H | 1 |
| 212 | i-Butyl | C—H | 1 |
| 213 | sec-Butyl | C—H | 1 |
| 214 | t-Butyl | C—H | 1 |
| 215 | cyclobutyl | C—H | 1 |
| 216 | -CH2CH2-OMe | C—H | 1 |
| 217 | -CH2CH2-OH | C—H | 1 |
| 218 | -CH2CH2-CF3 | C—H | 1 |
| 219 | cyclopentyl | C—H | 1 |
| 220 | cyclohexyl | C—H | 1 |
| 221 | Ph | C—H | 1 |
| 222 | H | C—F | 1 |
| 223 | Methyl | C—F | 1 |
| 224 | Ethyl | C—F | 1 |
| 225 | Propyl | C—F | 1 |
| 226 | Allyl | C—F | 1 |
| 227 | i-Propyl | C—F | 1 |
| 228 | cyclopropyl | C—F | 1 |
| 229 | i-Butyl | C—F | 1 |
| 230 | sec-Butyl | C—F | 1 |
| 231 | t-Butyl | C—F | 1 |
| 232 | cyclobutyl | C—F | 1 |
| 233 | -CH2CH2-OMe | C—F | 1 |
| 234 | -CH2CH2-OH | C—F | 1 |
| 235 | -CH2CH2-CF3 | C—F | 1 |
| 236 | cyclopentyl | C—F | 1 |
| 237 | cyclohexyl | C—F | 1 |
| 238 | Ph | C—F | 1 |
| 239 | H | C—OMe | 1 |
| 240 | Methyl | C—OMe | 1 |
| 241 | Ethyl | C—OMe | 1 |
| 242 | Propyl | C—OMe | 1 |
| 243 | Allyl | C—OMe | 1 |
| 244 | i-Propyl | C—OMe | 1 |

TABLE 2-continued

| compound | R³ | X³ | n |
|---|---|---|---|
| 245 | cyclopropyl-CH₂ | C—OMe | 1 |
| 246 | i-Butyl | C—OMe | 1 |
| 247 | sec-Butyl | C—OMe | 1 |
| 248 | t-Butyl | C—OMe | 1 |
| 249 | cyclobutyl-CH₂ | C—OMe | 1 |
| 250 | CH₂CH₂OMe | C—OMe | 1 |
| 251 | CH₂CH₂OH | C—OMe | 1 |
| 252 | CH₂CH₂CF₃ | C—OMe | 1 |
| 253 | cyclopentyl-CH₂ | C—OMe | 1 |
| 254 | cyclohexyl-CH₂ | C—OMe | 1 |
| 255 | CH₂Ph | C—OMe | 1 |
| 256 | H | N | 1 |
| 257 | Methyl | N | 1 |
| 258 | Ethyl | N | 1 |
| 259 | Propyl | N | 1 |
| 260 | Allyl | N | 1 |
| 261 | i-Propyl | N | 1 |
| 262 | cyclopropyl-CH₂ | N | 1 |
| 263 | i-Butyl | N | 1 |
| 264 | sec-Butyl | N | 1 |
| 265 | t-Butyl | N | 1 |
| 266 | cyclobutyl-CH₂ | N | 1 |
| 267 | CH₂CH₂OMe | N | 1 |
| 268 | CH₂CH₂OH | N | 1 |
| 269 | CH₂CH₂CF₃ | N | 1 |
| 270 | cyclopentyl-CH₂ | N | 1 |
| 271 | cyclohexyl-CH₂ | N | 1 |
| 272 | CH₂Ph | N | 1. |

13. The compound of claim 1, which is selected from compounds of Formula XIII, or a pharmaceutically acceptable salt thereof:

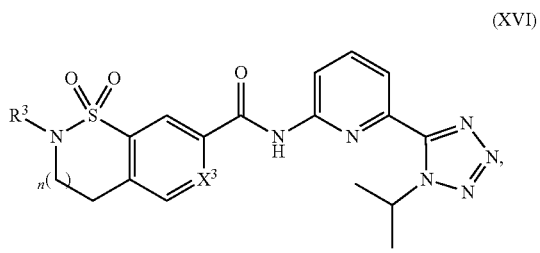

(XVI)

wherein R³, X³, and n are delineated for each compound in Table 3:

TABLE 3

| compound | R³ | X³ | n |
|---|---|---|---|
| 273 | H | C—H | 0 |
| 274 | Methyl | C—H | 0 |
| 275 | Ethyl | C—H | 0 |
| 276 | Propyl | C—H | 0 |
| 277 | Allyl | C—H | 0 |
| 278 | i-Propyl | C—H | 0 |
| 279 | cyclopropyl-CH₂ | C—H | 0 |
| 280 | i-Butyl | C—H | 0 |
| 281 | sec-Butyl | C—H | 0 |
| 282 | t-Butyl | C—H | 0 |
| 283 | cyclobutyl-CH₂ | C—H | 0 |
| 284 | CH₂CH₂OMe | C—H | 0 |

TABLE 3-continued

| compound | R³ | X³ | n |
|---|---|---|---|
| 285 | ~~~CH₂CH₂OH | C—H | 0 |
| 286 | ~~~CH₂CH₂CF₃ | C—H | 0 |
| 287 | cyclopentyl | C—H | 0 |
| 288 | cyclohexyl | C—H | 0 |
| 289 | —Ph | C—H | 0 |
| 290 | H | C—F | 0 |
| 291 | Methyl | C—F | 0 |
| 292 | Ethyl | C—F | 0 |
| 293 | Propyl | C—F | 0 |
| 294 | Allyl | C—F | 0 |
| 295 | i-Propyl | C—F | 0 |
| 296 | cyclopropyl | C—F | 0 |
| 297 | i-Butyl | C—F | 0 |
| 298 | sec-Butyl | C—F | 0 |
| 299 | t-Butyl | C—F | 0 |
| 300 | cyclobutyl | C—F | 0 |
| 301 | ~~~CH₂CH₂OMe | C—F | 0 |
| 302 | ~~~CH₂CH₂OH | C—F | 0 |
| 303 | ~~~CH₂CH₂CF₃ | C—F | 0 |
| 304 | cyclopentyl | C—F | 0 |
| 305 | cyclohexyl | C—F | 0 |

TABLE 3-continued

| compound | R³ | X³ | n |
|---|---|---|---|
| 306 | —Ph | C—F | 0 |
| 307 | H | C—OMe | 0 |
| 308 | Methyl | C—OMe | 0 |
| 309 | Ethyl | C—OMe | 0 |
| 310 | Propyl | C—OMe | 0 |
| 311 | Allyl | C—OMe | 0 |
| 312 | i-Propyl | C—OMe | 0 |
| 313 | cyclopropyl | C—OMe | 0 |
| 314 | i-Butyl | C—OMe | 0 |
| 315 | sec-Butyl | C—OMe | 0 |
| 316 | t-Butyl | C—OMe | 0 |
| 317 | cyclobutyl | C—OMe | 0 |
| 318 | ~~~CH₂CH₂OMe | C—OMe | 0 |
| 319 | ~~~CH₂CH₂OH | C—OMe | 0 |
| 320 | ~~~CH₂CH₂CF₃ | C—OMe | 0 |
| 321 | cyclopentyl | C—OMe | 0 |
| 322 | cyclohexyl | C—OMe | 0 |
| 323 | —Ph | C—OMe | 0 |
| 324 | H | N | 0 |
| 325 | Methyl | N | 0 |
| 326 | Ethyl | N | 0 |
| 327 | Propyl | N | 0 |
| 328 | Allyl | N | 0 |
| 329 | i-Propyl | N | 0 |
| 330 | cyclopropyl | N | 0 |
| 331 | i-Butyl | N | 0 |
| 332 | sec-Butyl | N | 0 |
| 333 | t-Butyl | N | 0 |

TABLE 3-continued

| compound | R³ | X³ | n |
|---|---|---|---|
| 334 | cyclobutyl | N | 0 |
| 335 | -CH₂CH₂-OMe | N | 0 |
| 336 | -CH₂CH₂-OH | N | 0 |
| 337 | -CH₂CH₂-CF₃ | N | 0 |
| 338 | cyclopentyl | N | 0 |
| 339 | cyclohexyl | N | 0 |
| 340 | Ph | N | 0 |
| 341 | H | C—H | 1 |
| 342 | Methyl | C—H | 1 |
| 343 | Ethyl | C—H | 1 |
| 344 | Propyl | C—H | 1 |
| 345 | Allyl | C—H | 1 |
| 346 | i-Propyl | C—H | 1 |
| 347 | cyclopropyl | C—H | 1 |
| 348 | i-Butyl | C—H | 1 |
| 349 | sec-Butyl | C—H | 1 |
| 350 | t-Butyl | C—H | 1 |
| 351 | cyclobutyl | C—H | 1 |
| 352 | -CH₂CH₂-OMe | C—H | 1 |
| 353 | -CH₂CH₂-OH | C—H | 1 |
| 354 | -CH₂CH₂-CF₃ | C—H | 1 |
| 355 | cyclopentyl | C—H | 1 |
| 356 | cyclohexyl | C—H | 1 |
| 357 | Ph | C—H | 1 |
| 358 | H | C—F | 1 |
| 359 | Methyl | C—F | 1 |
| 360 | Ethyl | C—F | 1 |
| 361 | Propyl | C—F | 1 |
| 362 | Allyl | C—F | 1 |
| 363 | i-Propyl | C—F | 1 |
| 364 | cyclopropyl | C—F | 1 |
| 365 | i-Butyl | C—F | 1 |
| 366 | sec-Butyl | C—F | 1 |
| 367 | t-Butyl | C—F | 1 |
| 368 | cyclobutyl | C—F | 1 |
| 369 | -CH₂CH₂-OMe | C—F | 1 |
| 370 | -CH₂CH₂-OH | C—F | 1 |
| 371 | -CH₂CH₂-CF₃ | C—F | 1 |
| 372 | cyclopentyl | C—F | 1 |
| 373 | cyclohexyl | C—F | 1 |
| 374 | Ph | C—F | 1 |
| 375 | H | C—OMe | 1 |
| 376 | Methyl | C—OMe | 1 |
| 377 | Ethyl | C—OMe | 1 |
| 378 | Propyl | C—OMe | 1 |
| 379 | Allyl | C—OMe | 1 |
| 380 | i-Propyl | C—OMe | 1 |

TABLE 3-continued

| compound | R³ | X³ | n |
|---|---|---|---|
| 381 | (cyclopropyl) | C—OMe | 1 |
| 382 | i-Butyl | C—OMe | 1 |
| 383 | sec-Butyl | C—OMe | 1 |
| 384 | t-Butyl | C—OMe | 1 |
| 385 | (cyclobutyl) | C—OMe | 1 |
| 386 | —CH₂CH₂OMe | C—OMe | 1 |
| 387 | —CH₂CH₂OH | C—OMe | 1 |
| 388 | —CH₂CH₂CF₃ | C—OMe | 1 |
| 389 | (cyclopentyl) | C—OMe | 1 |
| 390 | (cyclohexyl) | C—OMe | 1 |
| 391 | —Ph | C—OMe | 1 |
| 392 | H | N | 1 |
| 393 | Methyl | N | 1 |
| 394 | Ethyl | N | 1 |
| 395 | Propyl | N | 1 |
| 396 | Allyl | N | 1 |
| 397 | i-Propyl | N | 1 |
| 398 | (cyclopropyl) | N | 1 |
| 399 | i-Butyl | N | 1 |
| 400 | sec-Butyl | N | 1 |
| 401 | t-Butyl | N | 1 |
| 402 | (cyclobutyl) | N | 1 |
| 403 | —CH₂CH₂OMe | N | 1 |
| 404 | —CH₂CH₂OH | N | 1 |
| 405 | —CH₂CH₂CF₃ | N | 1 |
| 406 | (cyclopentyl) | N | 1 |
| 407 | (cyclohexyl) | N | 1 |
| 408 | —Ph | N | 1. |

14. The compound of claim 1, which is selected from compounds of Formula XIX, or a pharmaceutically acceptable salt thereof:

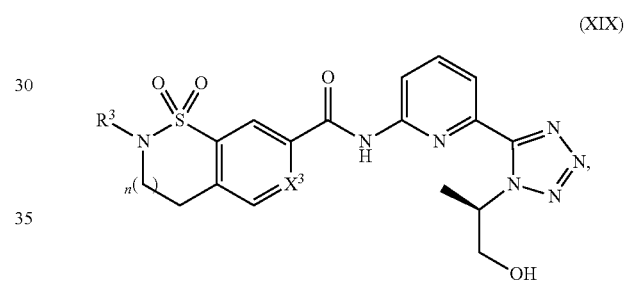

(XIX)

wherein R³, X³, and n are delineated for each compound in Table 4:

TABLE 4

| compound | R³ | X³ | n |
|---|---|---|---|
| 409 | H | C—H | 0 |
| 410 | Methyl | C—H | 0 |
| 411 | Ethyl | C—H | 0 |
| 412 | Propyl | C—H | 0 |
| 413 | Allyl | C—H | 0 |
| 414 | i-Propyl | C—H | 0 |
| 415 | (cyclopropyl) | C—H | 0 |
| 416 | i-Butyl | C—H | 0 |
| 417 | sec-Butyl | C—H | 0 |
| 418 | t-Butyl | C—H | 0 |
| 419 | (cyclobutyl) | C—H | 0 |
| 420 | —CH₂CH₂OMe | C—H | 0 |

TABLE 4-continued

| compound | R³ | X³ | n |
|---|---|---|---|
| 421 | -CH₂CH₂OH | C—H | 0 |
| 422 | -CH₂CH₂CF₃ | C—H | 0 |
| 423 | -cyclopentyl | C—H | 0 |
| 424 | -cyclohexyl | C—H | 0 |
| 425 | -Ph | C—H | 0 |
| 426 | H | C—F | 0 |
| 427 | Methyl | C—F | 0 |
| 428 | Ethyl | C—F | 0 |
| 429 | Propyl | C—F | 0 |
| 430 | Allyl | C—F | 0 |
| 431 | i-Propyl | C—F | 0 |
| 432 | -cyclopropyl | C—F | 0 |
| 433 | i-Butyl | C—F | 0 |
| 434 | sec-Butyl | C—F | 0 |
| 435 | t-Butyl | C—F | 0 |
| 436 | -cyclobutyl | C—F | 0 |
| 437 | -CH₂CH₂OMe | C—F | 0 |
| 438 | -CH₂CH₂OH | C—F | 0 |
| 439 | -CH₂CH₂CF₃ | C—F | 0 |
| 440 | -cyclopentyl | C—F | 0 |
| 441 | -cyclohexyl | C—F | 0 |
| 442 | -Ph | C—F | 0 |
| 443 | H | C—OMe | 0 |
| 444 | Methyl | C—OMe | 0 |
| 445 | Ethyl | C—OMe | 0 |
| 446 | Propyl | C—OMe | 0 |
| 447 | Allyl | C—OMe | 0 |
| 448 | i-Propyl | C—OMe | 0 |
| 449 | -cyclopropyl | C—OMe | 0 |
| 450 | i-Butyl | C—OMe | 0 |
| 451 | sec-Butyl | C—OMe | 0 |
| 452 | t-Butyl | C—OMe | 0 |
| 453 | -cyclobutyl | C—OMe | 0 |
| 454 | -CH₂CH₂OMe | C—OMe | 0 |
| 455 | -CH₂CH₂OH | C—OMe | 0 |
| 456 | -CH₂CH₂CF₃ | C—OMe | 0 |
| 457 | -cyclopentyl | C—OMe | 0 |
| 458 | -cyclohexyl | C—OMe | 0 |
| 459 | -Ph | C—OMe | 0 |
| 460 | H | N | 0 |
| 461 | Methyl | N | 0 |
| 462 | Ethyl | N | 0 |
| 463 | Propyl | N | 0 |
| 464 | Allyl | N | 0 |
| 465 | i-Propyl | N | 0 |
| 466 | -cyclopropyl | N | 0 |
| 467 | i-Butyl | N | 0 |
| 468 | sec-Butyl | N | 0 |
| 469 | t-Butyl | N | 0 |

TABLE 4-continued

| compound | R³ | X³ | n |
|---|---|---|---|
| 470 | cyclobutyl | N | 0 |
| 471 | -CH₂CH₂-OMe | N | 0 |
| 472 | -CH₂CH₂-OH | N | 0 |
| 473 | -CH₂CH₂-CF₃ | N | 0 |
| 474 | cyclopentyl | N | 0 |
| 475 | cyclohexyl | N | 0 |
| 476 | -Ph | N | 0 |
| 477 | H | C—H | 1 |
| 478 | Methyl | C—H | 1 |
| 479 | Ethyl | C—H | 1 |
| 480 | Propyl | C—H | 1 |
| 481 | Allyl | C—H | 1 |
| 482 | i-Propyl | C—H | 1 |
| 483 | cyclopropyl | C—H | 1 |
| 484 | i-Butyl | C—H | 1 |
| 485 | sec-Butyl | C—H | 1 |
| 486 | t-Butyl | C—H | 1 |
| 487 | cyclobutyl | C—H | 1 |
| 488 | -CH₂CH₂-OMe | C—H | 1 |
| 489 | -CH₂CH₂-OH | C—H | 1 |
| 490 | -CH₂CH₂-CF₃ | C—H | 1 |
| 491 | cyclopentyl | C—H | 1 |
| 492 | cyclohexyl | C—H | 1 |
| 493 | -Ph | C—H | 1 |
| 494 | H | C—F | 1 |
| 495 | Methyl | C—F | 1 |
| 496 | Ethyl | C—F | 1 |
| 497 | Propyl | C—F | 1 |
| 498 | Allyl | C—F | 1 |
| 499 | i-Propyl | C—F | 1 |
| 500 | cyclopropyl | C—F | 1 |
| 501 | i-Butyl | C—F | 1 |
| 502 | sec-Butyl | C—F | 1 |
| 503 | t-Butyl | C—F | 1 |
| 504 | cyclobutyl | C—F | 1 |
| 505 | -CH₂CH₂-OMe | C—F | 1 |
| 506 | -CH₂CH₂-OH | C—F | 1 |
| 507 | -CH₂CH₂-CF₃ | C—F | 1 |
| 508 | cyclopentyl | C—F | 1 |
| 509 | cyclohexyl | C—F | 1 |
| 510 | -Ph | C—F | 1 |
| 511 | H | C—OMe | 1 |
| 512 | Methyl | C—OMe | 1 |
| 513 | Ethyl | C—OMe | 1 |
| 514 | Propyl | C—OMe | 1 |
| 515 | Allyl | C—OMe | 1 |
| 516 | i-Propyl | C—OMe | 1 |

TABLE 4-continued

| compound | R³ | X³ | n |
|---|---|---|---|
| 517 | cyclopropyl | C—OMe | 1 |
| 518 | i-Butyl | C—OMe | 1 |
| 519 | sec-Butyl | C—OMe | 1 |
| 520 | t-Butyl | C—OMe | 1 |
| 521 | cyclobutyl | C—OMe | 1 |
| 522 | -CH₂CH₂-OMe | C—OMe | 1 |
| 523 | -CH₂CH₂-OH | C—OMe | 1 |
| 524 | -CH₂CH₂-CF₃ | C—OMe | 1 |
| 525 | cyclopentyl | C—OMe | 1 |
| 526 | cyclohexyl | C—OMe | 1 |
| 527 | -Ph | C—OMe | 1 |

TABLE 4-continued

| compound | R³ | X³ | n |
|---|---|---|---|
| 528 | H | N | 1 |
| 529 | Methyl | N | 1 |
| 530 | Ethyl | N | 1 |
| 531 | Propyl | N | 1 |
| 532 | Allyl | N | 1 |
| 533 | i-Propyl | N | 1 |
| 534 | cyclopropyl | N | 1 |
| 535 | i-Butyl | N | 1 |
| 536 | sec-Butyl | N | 1 |
| 537 | t-Butyl | N | 1 |
| 538 | cyclobutyl | N | 1 |
| 539 | -CH₂CH₂-OMe | N | 1 |
| 540 | -CH₂CH₂-OH | N | 1 |
| 541 | -CH₂CH₂-CF₃ | N | 1 |
| 542 | cyclopentyl | N | 1 |
| 543 | cyclohexyl | N | 1 |
| 544 | -Ph | N | 1. |

15. The compound of claim 1, selected from the compounds set forth below or a pharmaceutically acceptable salt thereof:

| Compound | Structure |
|---|---|
| 1 | (structure shown) |

| Compound | Structure |
|---|---|
| 2 | (structure) |
| 3 | (structure) |
| 4 | (structure) |
| 5 | (structure) |
| 6 | (structure) |
| 7 | (structure) |
| 8 | (structure) |

| Compound | Structure |
|---|---|
| 9 | (structure: isopropyl-benzisothiazole-1,1-dioxide with 5-F substituent, carboxamide linked to pyridine-tetrazole with (S)-1-hydroxypropan-2-yl) |
| 10 | (structure: isopropyl-benzisothiazole-1,1-dioxide with 5-OMe substituent, carboxamide linked to pyridine-tetrazole with (S)-1-hydroxypropan-2-yl) |
| 11 | (structure: isopropyl-benzisothiazole-1,1-dioxide with 5-OEt substituent, carboxamide linked to pyridine-tetrazole with (S)-1-hydroxypropan-2-yl) |
| 12 | (structure: isopropyl-benzisothiazole-1,1-dioxide with 5-OCH$_2$CF$_3$ substituent, carboxamide linked to pyridine-tetrazole with (S)-1-hydroxypropan-2-yl) |
| 13 | (structure: isopropyl-benzisothiazole-1,1-dioxide with 5-OiPr substituent, carboxamide linked to pyridine-tetrazole with (S)-1-hydroxypropan-2-yl) |
| 14 | (structure: isopropyl-benzisothiazole-1,1-dioxide with 5-N(Me)$_2$ substituent, carboxamide linked to pyridine-tetrazole with (S)-1-hydroxypropan-2-yl) |

-continued

| Compound | Structure |
|---|---|
| 15 | 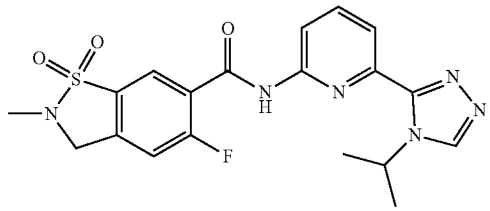 [SMILES: CC(C)n1cnnc1-c1cccc(NC(=O)c2cc3c(cc2F)CN(C)S3(=O)=O)n1] |
| 16 | 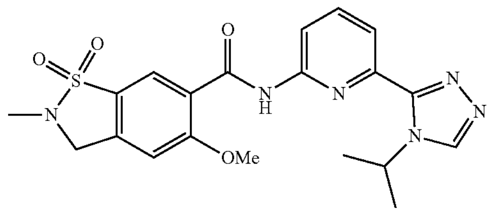 [SMILES: COc1cc2c(cc1C(=O)Nc1cccc(-c3nncn3C(C)C)n1)S(=O)(=O)N(C)C2] |
| 17 | 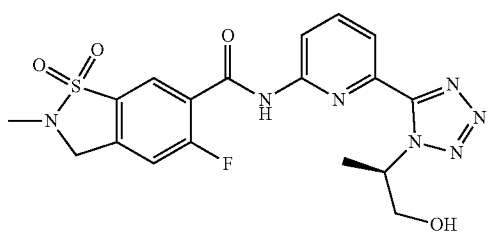 [SMILES: C[C@H](CO)n1nnnc1-c1cccc(NC(=O)c2cc3c(cc2F)CN(C)S3(=O)=O)n1] |
| 18 | 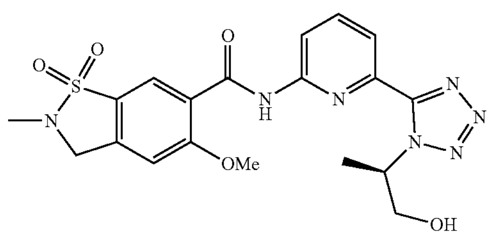 [SMILES: COc1cc2c(cc1C(=O)Nc1cccc(-c3nnnn3[C@H](C)CO)n1)S(=O)(=O)N(C)C2] |
| 19 | 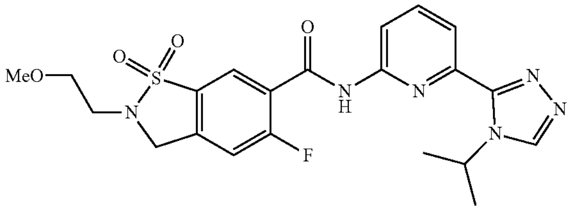 [SMILES: COCCN1Cc2cc(F)c(C(=O)Nc3cccc(-c4nncn4C(C)C)n3)cc2S1(=O)=O] |
| 20 | 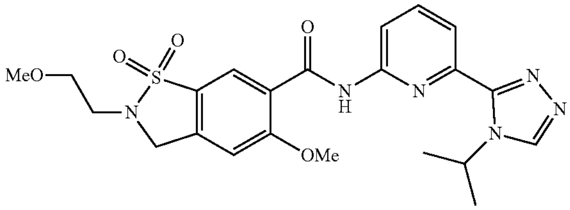 [SMILES: COCCN1Cc2cc(OC)c(C(=O)Nc3cccc(-c4nncn4C(C)C)n3)cc2S1(=O)=O] |
| 21 | 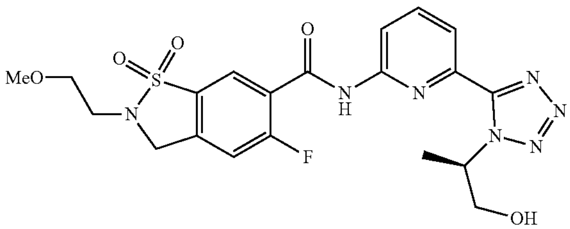 [SMILES: COCCN1Cc2cc(F)c(C(=O)Nc3cccc(-c4nnnn4[C@H](C)CO)n3)cc2S1(=O)=O] |

-continued

| Compound | Structure |
|---|---|
| 22 | 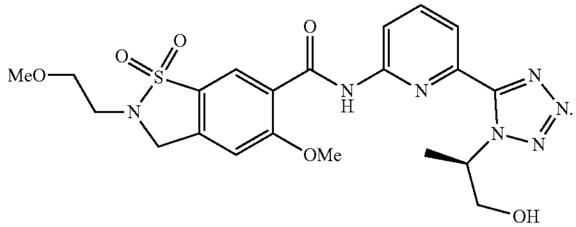 [SMILES: COCCN1Cc2cc(OC)c(C(=O)Nc3cccc(-c4nnnn4[C@H](C)CO)n3)cc2S1(=O)=O] |

16. A pharmaceutical composition comprising a compound of claim 1 and a pharmaceutically acceptable excipient.

17. A method for treating an ASK-1 mediated disease or condition in a subject in need thereof, wherein the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease, comprising administering to the subject a therapeutically effective amount of a compound according to claim 1.

18. The method according to claim 17 wherein the ASK-1 mediated disease or condition is (a) a chronic liver disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency; (b) a renal disease selected from the group consisting of diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease; (c) a cardiovascular disease selected from the group consisting of atherosclerosis, arteriosclerosis, reperfusion/ischemia in stroke, cardiac hypertrophy, respiratory diseases, heart attacks, and myocardial ischemia; or (d) a metabolic disease selected from the group consisting of insulin resistance, Type I and Type II diabetes, and obesity.

19. A method for treating a disease selected from the group consisting of glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, Sjoegren's syndrome, ischemia/reperfusion in stroke, heart attacks, myocardial ischemia, organ hypoxia, vascular hyperplasia, cardiac hypertrophy, hepatic ischemia, congestive heart failure, pathologic immune responses thrombin-induced platelet aggregation, osteoporosis, osteoarthritis, multiple myeloma-related bone disorder, Alzheimer's disease, Parkinson's disease, amyotrophic lateral sclerosis (ALS), epilepsy, seizures, Huntington's disease, polyglutamine diseases, traumatic brain injury, ischemic and hemorrhaging stroke, cerebral ischemias and neurodegenerative disease caused by traumatic injury, acute hypoxia, ischemia or glutamate neurotoxicity, in a subject in need thereof, comprising administering to the subject a therapeutically effective amount of the compound according to claim 1.

* * * * *

UNITED STATES PATENT AND TRADEMARK OFFICE
CERTIFICATE OF CORRECTION

PATENT NO. : 10,683,289 B2
APPLICATION NO. : 16/400498
DATED : June 16, 2020
INVENTOR(S) : Brett Granger et al.

Page 1 of 1

It is certified that error appears in the above-identified patent and that said Letters Patent is hereby corrected as shown below:

In the Claims

<u>At Column 100</u>
In Claim 1, at Line 10, delete "12) –C(O)N($R^6$)(R');" and insert -- 12) –C(O)N($R^6$)($R^7$); --.

<u>At Column 102</u>
In Claim 6, at Line 16, after $R^{10}$, delete "R" and insert -- $R^{11}$ --.

Signed and Sealed this
Twentieth Day of October, 2020

Andrei Iancu
*Director of the United States Patent and Trademark Office*